US011357835B2

(12) United States Patent
Fallon et al.

(10) Patent No.: US 11,357,835 B2
(45) Date of Patent: Jun. 14, 2022

(54) **COMPOSITIONS AND METHODS FOR THE TREATMENT OR THE PREVENTION OF *E. COLI* INFECTIONS AND FOR THE ERADICATION OR REDUCTION OF *E. COLI* SURFACES**

(71) Applicant: Galenagen, LLC, Rye Brook, NY (US)

(72) Inventors: Joan M. Fallon, White Plains, NY (US); Matthew Heil, Sherman, CT (US); James J. Fallon, Armonk, NY (US)

(73) Assignee: GALENAGEN, LLC, Rye Brook, NY (US)

( * ) Notice: Subject to any disclaimer, the term of this patent is extended or adjusted under 35 U.S.C. 154(b) by 0 days.

(21) Appl. No.: 15/840,883

(22) Filed: Dec. 13, 2017

(65) Prior Publication Data

US 2018/0104315 A1  Apr. 19, 2018

Related U.S. Application Data

(63) Continuation of application No. 14/713,221, filed on May 15, 2015, now Pat. No. 9,895,427, which is a continuation of application No. 13/144,290, filed as application No. PCT/US2010/020259 on Jan. 6, 2010, now Pat. No. 9,084,784.

(60) Provisional application No. 61/170,856, filed on Apr. 20, 2009, provisional application No. 61/153,279, filed on Feb. 17, 2009, provisional application No. 61/142,718, filed on Jan. 6, 2009.

(51) Int. Cl.
| | |
|---|---|
| *A61K 38/48* | (2006.01) |
| *A61K 38/47* | (2006.01) |
| *A61K 45/06* | (2006.01) |
| *A01N 63/50* | (2020.01) |
| *A61K 38/46* | (2006.01) |

(52) U.S. Cl.
CPC .......... *A61K 38/4826* (2013.01); *A01N 63/50* (2020.01); *A61K 38/465* (2013.01); *A61K 38/47* (2013.01); *A61K 45/06* (2013.01); *Y02A 50/30* (2018.01)

(58) Field of Classification Search
CPC .. A61K 38/4826; A61K 38/465; A61K 38/47; A61K 45/06; A01N 63/50; Y02A 50/30
USPC ........................................................ 424/94.2
See application file for complete search history.

(56) References Cited

U.S. PATENT DOCUMENTS

| | | |
|---|---|---|
| 3,002,883 A | 10/1961 | Butt et al. |
| 3,223,594 A | 12/1965 | Hoek |
| 3,322,626 A | 5/1967 | D'Argento |
| 3,357,894 A | 12/1967 | Uriel et al. |
| 3,515,642 A | 6/1970 | Hiroyuki et al. |
| 3,536,809 A | 10/1970 | Applezweig et al. |
| 3,574,819 A | 4/1971 | Franz et al. |
| 3,598,123 A | 8/1971 | Zaffaroni |
| 3,710,795 A | 1/1973 | Higuchi et al. |
| 3,786,615 A | 1/1974 | Bauer |
| 3,845,770 A | 11/1974 | Theeuwes et al. |
| 3,860,708 A | 1/1975 | Prout |
| 3,916,899 A | 11/1975 | Theeuwes et al. |
| 3,940,478 A | 2/1976 | Kurtz |
| RE28,819 E | 5/1976 | Thompson |
| 4,008,719 A | 2/1977 | Theeuwes et al. |
| 4,044,126 A | 8/1977 | Cook et al. |
| 4,079,125 A | 3/1978 | Sipos |
| 4,145,410 A | 3/1979 | Sears |
| 4,199,322 A | 4/1980 | Danna et al. |
| 4,241,046 A | 12/1980 | Papahadjopoulos et al. |
| 4,280,971 A | 7/1981 | Wischniewski et al. |
| 4,328,245 A | 5/1982 | Yu et al. |
| 4,358,603 A | 11/1982 | Yu |
| 4,364,923 A | 12/1982 | Cook et al. |
| 4,395,454 A | 7/1983 | Baldwin |
| 4,409,239 A | 10/1983 | Yu |
| 4,410,545 A | 10/1983 | Yu et al. |
| 4,414,209 A | 11/1983 | Cook et al. |
| 4,447,412 A | 5/1984 | Bilton |
| 4,456,544 A | 6/1984 | Lupova et al. |
| 4,500,515 A | 2/1985 | Libby |
| 4,623,624 A | 11/1986 | Schultze |

(Continued)

FOREIGN PATENT DOCUMENTS

| | | |
|---|---|---|
| CA | 2198317 A1 | 8/1998 |
| CA | 2263703 A1 | 8/1999 |

(Continued)

OTHER PUBLICATIONS

Bhattacharjee et al., Treatment of Pancreatic Exocrine Insufficiency with Enteric Coated Pancreatin Formulations: An overview, International Journal of Pharmaceutical Sciences and Nanotechnology, vol. 6, Iss. 3, (2013), p. 2125-2130.*

(Continued)

*Primary Examiner* — Jennifer M. H. Tichy

(74) *Attorney, Agent, or Firm* — Wilson Sonsini Goodrich & Rosati

(57) ABSTRACT

Compositions and methods for treating or preventing *E. coli* infections are provided. The compositions can be formulated as pharmaceutical compositions or as disinfectants, sanitizers, detergents or antiseptics, and can be used to eradicate or reduce *E. coli* populations and thereby treat or prevent infection by *E. coli*. The compositions include one or more digestive enzymes, e.g., one or more protease, lipases, and amylases. Methods of use of the compositions are also provided.

23 Claims, No Drawings

(56) References Cited

U.S. PATENT DOCUMENTS

| | | |
|---|---|---|
| 4,710,384 A | 12/1987 | Rotman |
| 4,826,679 A | 5/1989 | Roy |
| 4,965,012 A | 10/1990 | Olson |
| 5,023,108 A | 6/1991 | Bagaria et al. |
| 5,059,595 A | 10/1991 | Le Grazie |
| 5,073,543 A | 12/1991 | Marshall et al. |
| 5,120,548 A | 6/1992 | McClelland et al. |
| 5,190,775 A | 3/1993 | Klose |
| 5,227,166 A | 7/1993 | Ueda et al. |
| 5,250,418 A | 10/1993 | Moeller et al. |
| 5,324,514 A | 6/1994 | Sipos |
| 5,354,556 A | 10/1994 | Sparks et al. |
| 5,378,462 A | 1/1995 | Boedecker et al. |
| 5,436,319 A | 7/1995 | Kung et al. |
| 5,437,319 A | 8/1995 | Garuglieri |
| 5,439,935 A | 8/1995 | Rawlings et al. |
| 5,460,812 A | 10/1995 | Sipos |
| 5,476,661 A | 12/1995 | Pillai et al. |
| 5,527,678 A | 6/1996 | Blaser et al. |
| 5,585,115 A | 12/1996 | Sherwood et al. |
| 5,591,767 A | 1/1997 | Mohr et al. |
| 5,607,863 A | 3/1997 | Chandler |
| 5,639,476 A | 6/1997 | Oshlack et al. |
| 5,648,335 A | 7/1997 | Lewis et al. |
| 5,674,532 A | 10/1997 | Atzl et al. |
| 5,674,533 A | 10/1997 | Santus et al. |
| 5,686,255 A | 11/1997 | Deth |
| 5,686,311 A | 11/1997 | Shaw |
| 5,750,104 A | 5/1998 | Sipos |
| 5,753,223 A | 5/1998 | Shibahara et al. |
| 5,776,917 A | 7/1998 | Blank et al. |
| 5,858,758 A | 1/1999 | Hillman et al. |
| 5,860,957 A | 1/1999 | Jacobsen et al. |
| 5,948,433 A | 9/1999 | Burton et al. |
| 5,952,178 A | 9/1999 | Lapidus et al. |
| 5,958,875 A | 9/1999 | Longo et al. |
| 5,977,175 A | 11/1999 | Lin |
| 5,983,134 A | 11/1999 | Ostrow |
| 5,985,317 A | 11/1999 | Venkateshwaran et al. |
| 5,985,891 A | 11/1999 | Rowe |
| 6,010,715 A | 1/2000 | Wick et al. |
| 6,011,001 A | 1/2000 | Navia et al. |
| 6,013,286 A | 1/2000 | Klose |
| 6,020,310 A | 2/2000 | Beck et al. |
| 6,020,314 A | 2/2000 | McMichael |
| 6,024,975 A | 2/2000 | D'Angelo et al. |
| 6,096,338 A | 8/2000 | Lacy et al. |
| 6,100,080 A | 8/2000 | Johansen |
| 6,149,585 A | 11/2000 | Gray |
| 6,153,236 A | 11/2000 | Wu et al. |
| 6,167,301 A | 12/2000 | Flower et al. |
| 6,168,569 B1 | 1/2001 | McEwen et al. |
| 6,187,309 B1 | 2/2001 | McMichael et al. |
| 6,197,746 B1 | 3/2001 | Beck et al. |
| 6,210,950 B1 | 4/2001 | Johnson et al. |
| 6,238,727 B1 | 5/2001 | Takemoto et al. |
| 6,251,478 B1 | 6/2001 | Pacifico et al. |
| 6,256,533 B1 | 7/2001 | Yuzhakov et al. |
| 6,261,595 B1 | 7/2001 | Stanley et al. |
| 6,261,602 B1 | 7/2001 | Calanchi et al. |
| 6,261,613 B1 | 7/2001 | Narayanaswamy et al. |
| 6,267,983 B1 | 7/2001 | Fujii et al. |
| 6,280,726 B1 | 8/2001 | Weinrauch et al. |
| 6,287,585 B1 | 9/2001 | Johansen |
| 6,309,669 B1 | 10/2001 | Setterstrom et al. |
| 6,312,741 B1 | 11/2001 | Navarro |
| 6,399,101 B1 | 6/2002 | Frontanes et al. |
| 6,482,839 B1 | 11/2002 | Thornfeldt |
| 6,498,143 B1 | 12/2002 | Beck et al. |
| 6,534,063 B1 | 3/2003 | Fallon |
| 6,534,259 B1 | 3/2003 | Wakefield |
| 6,558,708 B1 | 5/2003 | Lin |
| 6,562,629 B1 | 5/2003 | Lin et al. |
| 6,569,463 B2 | 5/2003 | Patel et al. |
| 6,616,954 B1 | 9/2003 | Dally et al. |
| 6,632,429 B1 | 10/2003 | Fallon |
| 6,660,831 B2 | 12/2003 | Fallon |
| 6,699,885 B2 | 3/2004 | Phillips |
| 6,727,073 B1 | 4/2004 | Moore et al. |
| 6,743,447 B2 | 6/2004 | Labergerie et al. |
| 6,764,447 B2 | 7/2004 | Iliff |
| 6,783,757 B2 | 8/2004 | Brudnak |
| 6,790,825 B2 | 9/2004 | Beck et al. |
| 6,797,291 B2 | 9/2004 | Richardson |
| 6,808,708 B2 | 10/2004 | Houston |
| 6,821,514 B2 | 11/2004 | Houston |
| 6,827,688 B2 | 12/2004 | Goto et al. |
| 6,835,397 B2 | 12/2004 | Lee et al. |
| 6,852,487 B1 | 2/2005 | Barany et al. |
| 6,861,053 B1 | 3/2005 | Lin et al. |
| 6,890,561 B1 | 5/2005 | Blatt et al. |
| 6,899,876 B2 | 5/2005 | Houston |
| 6,923,988 B2 | 8/2005 | Patel et al. |
| 6,980,958 B1 | 12/2005 | Surwit et al. |
| 7,048,906 B2 | 5/2006 | Lin et al. |
| 7,081,239 B2 | 7/2006 | Lin |
| 7,091,182 B2 | 8/2006 | Beck et al. |
| 7,101,573 B2 | 9/2006 | Szymczak et al. |
| 7,122,357 B2 | 10/2006 | Sander-Struckmeier et al. |
| 7,129,053 B1 | 10/2006 | Reiter et al. |
| 7,138,123 B2 | 11/2006 | Fallon |
| 7,232,670 B2 | 6/2007 | D'Azzo et al. |
| 7,244,412 B2 | 7/2007 | Lin |
| 7,285,633 B2 | 10/2007 | Wu et al. |
| RE40,059 E | 2/2008 | Pacifico et al. |
| 7,381,698 B2 | 6/2008 | Fein et al. |
| 7,395,216 B2 | 7/2008 | Rosenfeld et al. |
| 7,479,378 B2 | 1/2009 | Potthoff et al. |
| 7,483,747 B2 | 1/2009 | Gliner et al. |
| 7,588,757 B2 | 9/2009 | Ozawa et al. |
| 7,608,245 B2 | 10/2009 | Lin |
| 7,630,913 B2 | 12/2009 | Kay |
| 7,658,918 B1 | 2/2010 | Ortenzi et al. |
| 7,718,169 B2 | 5/2010 | Margolin et al. |
| 7,736,622 B2 | 6/2010 | Lin et al. |
| 7,935,799 B2 | 5/2011 | Lin et al. |
| 7,945,451 B2 | 5/2011 | Cosentino et al. |
| 8,008,036 B2 | 8/2011 | Fallon |
| 8,012,710 B2 | 9/2011 | Fallon |
| 8,012,930 B2 | 9/2011 | Fallon |
| 8,030,002 B2 | 10/2011 | Fallon |
| 8,055,516 B2 | 11/2011 | Iliff |
| 8,066,636 B2 | 11/2011 | Iliff |
| 8,084,025 B2 | 12/2011 | Fallon |
| 8,105,584 B2 | 1/2012 | Fallon |
| 8,163,278 B2 | 4/2012 | Fallon |
| 8,211,661 B2 | 7/2012 | Fallon |
| 8,221,747 B2 | 7/2012 | Ortenzi et al. |
| 8,318,158 B2 | 11/2012 | Fallon |
| 8,437,689 B2 | 5/2013 | Mazar |
| 8,486,390 B2 | 7/2013 | Fallon |
| 8,580,522 B2 | 11/2013 | Fallon |
| 8,613,918 B2 | 12/2013 | Fallon |
| 8,658,163 B2 | 2/2014 | Fallon |
| 8,673,877 B2 | 3/2014 | Fallon et al. |
| 8,778,335 B2 | 7/2014 | Fallon |
| 8,815,233 B2 | 8/2014 | Fallon |
| 8,921,054 B2 | 12/2014 | Fallon |
| 8,980,252 B2 | 3/2015 | Fallon et al. |
| 9,017,665 B2 | 4/2015 | Fallon |
| 9,023,344 B2 | 5/2015 | Fallon |
| 9,056,050 B2 | 6/2015 | Fallon et al. |
| 9,061,033 B2 | 6/2015 | Fallon |
| 9,084,784 B2 | 7/2015 | Fallon et al. |
| 9,107,419 B2 | 8/2015 | Fallon et al. |
| 9,233,146 B2 | 1/2016 | Fallon |
| 9,320,780 B2 | 4/2016 | Fallon |
| 9,345,721 B2 | 5/2016 | Fallon et al. |
| 9,377,459 B2 | 6/2016 | Fallon |
| 9,408,895 B2 | 8/2016 | Fallon et al. |
| 9,492,515 B2 | 11/2016 | Fallon et al. |
| 9,511,125 B2 | 12/2016 | Fallon et al. |
| 9,624,525 B2 | 4/2017 | Fallon |
| 9,624,526 B2 | 4/2017 | Fallon |

(56) References Cited

U.S. PATENT DOCUMENTS

| | | |
|---|---|---|
| 10,098,844 B2 | 10/2018 | Fallon |
| 2001/0006644 A1 | 7/2001 | Bova et al. |
| 2001/0023360 A1 | 9/2001 | Nelson et al. |
| 2001/0024660 A1 | 9/2001 | Ullah et al. |
| 2002/0001575 A1 | 1/2002 | Foreman |
| 2002/0037284 A1 | 3/2002 | Fallon |
| 2002/0061302 A1 | 5/2002 | Sander-Struckmeier et al. |
| 2002/0081628 A1 | 6/2002 | Fallon |
| 2002/0090653 A1 | 7/2002 | Fallon |
| 2002/0094367 A1 | 7/2002 | Fuglsang et al. |
| 2002/0103675 A1 | 8/2002 | Vanelli |
| 2002/0119914 A1 | 8/2002 | Zhu et al. |
| 2002/0141987 A1 | 10/2002 | Bjarnason |
| 2002/0183229 A1 | 12/2002 | Simpson |
| 2003/0097122 A1 | 5/2003 | Ganz et al. |
| 2004/0005304 A1 | 1/2004 | Brudnak |
| 2004/0028689 A1 | 2/2004 | Borody |
| 2004/0029752 A1 | 2/2004 | Sava et al. |
| 2004/0057944 A1 | 3/2004 | Galle et al. |
| 2004/0057962 A1 | 3/2004 | Timmerman |
| 2004/0071683 A1 | 4/2004 | Fallon |
| 2004/0076590 A1 | 4/2004 | Wilkins |
| 2004/0101562 A1 | 5/2004 | Maio |
| 2004/0121002 A1 | 6/2004 | Lee et al. |
| 2004/0209790 A1 | 10/2004 | Sava et al. |
| 2005/0026892 A1* | 2/2005 | Bodor ............... A61K 31/56 514/179 |
| 2005/0036950 A1 | 2/2005 | Jones et al. |
| 2005/0079594 A1 | 4/2005 | Marion |
| 2005/0137134 A1 | 6/2005 | Gill et al. |
| 2005/0170479 A1 | 8/2005 | Weaver et al. |
| 2005/0187130 A1 | 8/2005 | Brooker et al. |
| 2005/0232894 A1 | 10/2005 | Weiner et al. |
| 2006/0105379 A1 | 5/2006 | Wu et al. |
| 2006/0115467 A1 | 6/2006 | Pangborn et al. |
| 2006/0121017 A1 | 6/2006 | Margolin et al. |
| 2006/0182728 A1 | 8/2006 | Fallon |
| 2006/0183180 A1 | 8/2006 | Fallon |
| 2006/0198838 A1 | 9/2006 | Fallon |
| 2006/0253045 A1 | 11/2006 | Coifman |
| 2006/0258599 A1 | 11/2006 | Childers |
| 2006/0258708 A1 | 11/2006 | Andrulis, Jr. |
| 2006/0259995 A1 | 11/2006 | Cayouette et al. |
| 2006/0294108 A1 | 12/2006 | Adelson et al. |
| 2007/0031399 A1 | 2/2007 | Edens et al. |
| 2007/0053895 A1 | 3/2007 | Fallon |
| 2007/0092501 A1 | 4/2007 | Houston |
| 2007/0116695 A1 | 5/2007 | Fallon |
| 2007/0148151 A1 | 6/2007 | Frink et al. |
| 2007/0148152 A1 | 6/2007 | Shlieout et al. |
| 2007/0148153 A1 | 6/2007 | Shlieout et al. |
| 2007/0203426 A1 | 8/2007 | Kover et al. |
| 2008/0019959 A1 | 1/2008 | Becher et al. |
| 2008/0020036 A1 | 1/2008 | Jolly |
| 2008/0057086 A1 | 3/2008 | Etter |
| 2008/0058282 A1 | 3/2008 | Fallon et al. |
| 2008/0112900 A1 | 5/2008 | Du-Thumm et al. |
| 2008/0112944 A1 | 5/2008 | Pangborn et al. |
| 2008/0152637 A1 | 6/2008 | Fallon |
| 2008/0161265 A1 | 7/2008 | Fallon et al. |
| 2008/0166334 A1 | 7/2008 | Fallon |
| 2008/0177578 A1 | 7/2008 | Zakim |
| 2008/0187525 A1 | 8/2008 | Porubcan |
| 2008/0193436 A1 | 8/2008 | Shan et al. |
| 2008/0199448 A1 | 8/2008 | Ross et al. |
| 2008/0219966 A1 | 9/2008 | Fallon |
| 2008/0248558 A1 | 10/2008 | Deinhammer et al. |
| 2008/0254009 A1 | 10/2008 | Finegold |
| 2008/0274174 A1 | 11/2008 | Ortenzi et al. |
| 2008/0279839 A1 | 11/2008 | Schuler et al. |
| 2008/0279953 A1 | 11/2008 | Ortenzi et al. |
| 2008/0311554 A1 | 12/2008 | Slotman |
| 2008/0317731 A1 | 12/2008 | Gramatikova et al. |
| 2009/0004285 A1 | 1/2009 | Yu et al. |
| 2009/0063402 A1 | 3/2009 | Hayter |
| 2009/0110674 A1 | 4/2009 | Loizou |
| 2009/0117180 A1 | 5/2009 | Ortenzi et al. |
| 2009/0130081 A1 | 5/2009 | Fallon |
| 2009/0171696 A1 | 7/2009 | Allard et al. |
| 2009/0197289 A1 | 8/2009 | Fallon |
| 2009/0226414 A1 | 9/2009 | Tijssen et al. |
| 2009/0232789 A1 | 9/2009 | Fallon |
| 2009/0233344 A1 | 9/2009 | Kurfurst et al. |
| 2009/0263372 A1 | 10/2009 | Fallon |
| 2009/0285790 A1 | 11/2009 | Fallon |
| 2009/0286270 A1 | 11/2009 | Fallon |
| 2009/0304670 A1 | 12/2009 | Edens et al. |
| 2009/0324572 A1 | 12/2009 | Fallon |
| 2009/0324730 A1 | 12/2009 | Fallon |
| 2010/0092447 A1 | 4/2010 | Fallon |
| 2010/0169409 A1 | 7/2010 | Fallon et al. |
| 2010/0196344 A1 | 8/2010 | Margolin et al. |
| 2010/0209507 A1 | 8/2010 | Lin et al. |
| 2010/0233218 A1 | 9/2010 | Fallon |
| 2010/0239559 A1 | 9/2010 | Freedman et al. |
| 2010/0260857 A1 | 10/2010 | Fallon et al. |
| 2010/0270183 A1 | 10/2010 | Ortenzi et al. |
| 2010/0285116 A1 | 11/2010 | Joshi |
| 2011/0029922 A1 | 2/2011 | Hoffberg et al. |
| 2011/0052706 A1 | 3/2011 | Moest et al. |
| 2011/0065628 A1 | 3/2011 | Johnson et al. |
| 2011/0081320 A1 | 4/2011 | Westall et al. |
| 2011/0112005 A1 | 5/2011 | Brooker et al. |
| 2011/0182818 A1 | 7/2011 | Fallon |
| 2011/0200574 A1 | 8/2011 | Jolly et al. |
| 2011/0280853 A1 | 11/2011 | Fallon et al. |
| 2011/0280854 A1 | 11/2011 | Fallon et al. |
| 2012/0003628 A1 | 1/2012 | Fallon |
| 2012/0004192 A1 | 1/2012 | Fallon et al. |
| 2012/0027848 A1 | 2/2012 | Fallon et al. |
| 2012/0070504 A1 | 3/2012 | Fallon |
| 2012/0128764 A1 | 5/2012 | Venkatesh et al. |
| 2012/0189703 A1 | 7/2012 | Fallon et al. |
| 2012/0201875 A1 | 8/2012 | Ortenzi et al. |
| 2012/0207740 A1 | 8/2012 | Fallon |
| 2012/0230970 A1 | 9/2012 | Fallon |
| 2013/0059001 A1 | 3/2013 | Fallon |
| 2013/0095152 A1 | 4/2013 | Fallon |
| 2013/0171121 A1 | 7/2013 | Pierzynowski et al. |
| 2013/0195833 A1 | 8/2013 | Fallon |
| 2013/0202581 A1 | 8/2013 | Fallon et al. |
| 2013/0224172 A1 | 8/2013 | Fallon et al. |
| 2013/0323223 A1 | 12/2013 | Fallon et al. |
| 2014/0030333 A1 | 1/2014 | Fallon |
| 2014/0127184 A1 | 5/2014 | Fallon et al. |
| 2014/0147500 A1 | 5/2014 | Fallon et al. |
| 2014/0161787 A1 | 6/2014 | Fallon |
| 2014/0170637 A1 | 6/2014 | Fallon |
| 2014/0348881 A1 | 11/2014 | Fallon |
| 2015/0023944 A1 | 1/2015 | Fallon |
| 2015/0147308 A1 | 5/2015 | Fallon et al. |
| 2015/0150955 A1 | 6/2015 | Fallon et al. |
| 2015/0151198 A1 | 6/2015 | Dugan et al. |
| 2015/0174219 A1 | 6/2015 | Fallon |
| 2015/0182607 A1 | 7/2015 | Jolly et al. |
| 2015/0246104 A1 | 9/2015 | Fallon et al. |
| 2015/0246105 A1 | 9/2015 | Fallon et al. |
| 2015/0273030 A1 | 10/2015 | Fallon |
| 2015/0335589 A1 | 11/2015 | Fallon et al. |
| 2016/0045576 A1 | 2/2016 | Fallon et al. |
| 2016/0206708 A1 | 7/2016 | Fallon et al. |
| 2016/0213697 A1 | 7/2016 | Fallon |
| 2016/0266113 A1 | 9/2016 | Fallon |
| 2016/0287683 A1 | 10/2016 | Fallon |
| 2017/0157221 A1 | 6/2017 | Fallon |
| 2017/0189501 A1 | 7/2017 | Fallon |
| 2017/0202934 A1 | 7/2017 | Fallon |
| 2017/0246265 A1 | 8/2017 | Fallon |
| 2018/0161409 A1 | 6/2018 | Fallon |
| 2018/0243282 A1 | 8/2018 | Fallon |
| 2019/0175704 A1 | 6/2019 | Fallon |
| 2019/0183990 A1 | 6/2019 | Fallon et al. |
| 2019/0201507 A1 | 7/2019 | Fallon |
| 2019/0209667 A1 | 7/2019 | Fallon |

(56) References Cited

U.S. PATENT DOCUMENTS

| | | |
|---|---|---|
| 2019/0275066 A1 | 9/2019 | Fallon et al. |
| 2019/0275128 A1 | 9/2019 | Gleiberman et al. |
| 2020/0101145 A1 | 4/2020 | Fallon et al. |
| 2020/0282030 A1 | 9/2020 | Fallon et al. |
| 2020/0286620 A1 | 9/2020 | Fallon et al. |
| 2021/0162024 A1 | 6/2021 | Fallon et al. |
| 2021/0270846 A1 | 9/2021 | Fallon |

FOREIGN PATENT DOCUMENTS

| | | |
|---|---|---|
| CA | 2667976 A1 | 5/2008 |
| CA | 2719102 A1 | 9/2009 |
| CN | 1031562 A | 3/1989 |
| CN | 1275897 A | 12/2000 |
| CN | 1329923 A | 1/2002 |
| CN | 1552836 A | 12/2004 |
| CN | 1791430 A | 6/2006 |
| CN | 101039667 A | 9/2007 |
| CN | 101208092 A | 6/2008 |
| CN | 102300989 A | 12/2011 |
| CN | 102984941 A | 3/2013 |
| DE | 3738599 A1 | 5/1989 |
| DE | 4332985 A1 | 3/1995 |
| DE | 202010004926 U1 | 7/2010 |
| EP | 0425214 A2 | 5/1991 |
| EP | 0436110 A1 | 7/1991 |
| EP | 0451484 A1 | 10/1991 |
| EP | 0564739 A2 | 10/1993 |
| EP | 0564739 A3 | 4/1995 |
| EP | 1162995 B1 | 6/2003 |
| EP | 1413202 A1 | 4/2004 |
| EP | 1335706 B1 | 4/2005 |
| EP | 1019072 B1 | 5/2005 |
| EP | 1604677 A1 | 12/2005 |
| EP | 1931317 B1 | 12/2008 |
| EP | 2258837 A1 | 12/2010 |
| EP | 2318035 A1 | 5/2011 |
| EP | 2373791 A1 | 10/2011 |
| GB | 669782 A | 4/1952 |
| GB | 2347742 A | 9/2000 |
| GB | 2480772 A | 11/2011 |
| GB | 2506537 A | 4/2014 |
| JP | S523819 A | 1/1977 |
| JP | S62230714 A | 10/1987 |
| JP | H04364119 A | 12/1992 |
| JP | 2003517831 A | 6/2003 |
| JP | 2004500591 A | 1/2004 |
| JP | 2005515223 A | 5/2005 |
| JP | 2006512091 A | 4/2006 |
| JP | 2007523664 A | 8/2007 |
| JP | 2007530503 A | 11/2007 |
| JP | 2008521906 A | 6/2008 |
| JP | 2008283895 A | 11/2008 |
| JP | 2013517251 A | 5/2013 |
| KR | 20050084485 A | 8/2005 |
| RU | 2356244 C1 | 5/2009 |
| TW | 310277 B | 7/1997 |
| WO | WO-8402846 A1 | 8/1984 |
| WO | WO-8908694 A1 | 9/1989 |
| WO | WO-9002562 A1 | 3/1990 |
| WO | WO-9219708 A1 | 11/1992 |
| WO | WO-9219709 A1 | 11/1992 |
| WO | WO-9419005 A1 | 9/1994 |
| WO | WO-9522344 A1 | 8/1995 |
| WO | WO-9732480 A1 | 9/1997 |
| WO | WO-9822499 A2 | 5/1998 |
| WO | WO-9826807 A1 | 6/1998 |
| WO | WO-9822499 A3 | 7/1998 |
| WO | WO-9832336 A2 | 7/1998 |
| WO | WO-9852593 A1 | 11/1998 |
| WO | WO-9964059 A2 | 12/1999 |
| WO | WO-0009142 A1 | 2/2000 |
| WO | WO-9964059 A3 | 3/2000 |
| WO | WO-0021504 A1 | 4/2000 |
| WO | WO-0127612 A2 | 4/2001 |
| WO | WO-0143764 A2 | 6/2001 |
| WO | WO-0145835 A1 | 6/2001 |
| WO | WO-0127612 A3 | 10/2001 |
| WO | WO-0143764 A3 | 11/2001 |
| WO | WO-0214537 A2 | 2/2002 |
| WO | WO-0219828 A1 | 3/2002 |
| WO | WO-0214537 A3 | 5/2002 |
| WO | WO-02051352 A2 | 7/2002 |
| WO | WO-02051436 A2 | 7/2002 |
| WO | WO-03051345 A2 | 6/2003 |
| WO | WO-03059088 A1 | 7/2003 |
| WO | WO 2003051345 * | 7/2003 |
| WO | WO-2004060074 A1 | 7/2004 |
| WO | WO-2004093883 A2 | 11/2004 |
| WO | WO-2005092370 A1 | 10/2005 |
| WO | WO-2005115445 A1 | 12/2005 |
| WO | WO-2006031554 A2 | 3/2006 |
| WO | WO-2006044529 A1 | 4/2006 |
| WO | WO-2006060414 A2 | 6/2006 |
| WO | WO-2006031554 A3 | 9/2006 |
| WO | WO-2007002572 A2 | 1/2007 |
| WO | WO-2007074454 A2 | 7/2007 |
| WO | WO-2007147714 A1 | 12/2007 |
| WO | WO-2008013747 A2 | 1/2008 |
| WO | WO-2008021987 A2 | 2/2008 |
| WO | WO-2008102264 A2 | 8/2008 |
| WO | WO-2009114757 A2 | 9/2009 |
| WO | WO-2009155689 A1 | 12/2009 |
| WO | WO-2010002972 A1 | 1/2010 |
| WO | WO-2010025126 A1 | 3/2010 |
| WO | WO-2010080830 A1 | 7/2010 |
| WO | WO-2010080835 A1 | 7/2010 |
| WO | WO-2010120781 A1 | 10/2010 |
| WO | WO-2011000924 A1 | 1/2011 |
| WO | WO-2011050135 A1 | 4/2011 |
| WO | WO-2011114225 A1 | 9/2011 |
| WO | WO-2012067621 A1 | 5/2012 |
| WO | WO-2012145651 A2 | 10/2012 |
| WO | WO-2013103746 A1 | 7/2013 |
| WO | WO-2013116732 A1 | 8/2013 |
| WO | WO-2013181447 A1 | 12/2013 |

OTHER PUBLICATIONS

Alexrod FB et al. Hereditary sensory an autonomic neuropathies: types II, III and IV. Orphanet Journal of Rare Diseases, 2:39 (2007).
Anderson, George M., et al. Determination of serotonin in whole blood, platelet-rich plasma, platelet-poor plasma and plasma ultrafiltrate. Life Sciences 40(11):1063-1070 (Mar. 16, 1987) [Abstract Only].
Arnold, GL et al. Plasma amino acids profiles in children with autism: potential risk of nutritional deficiencies. J. Autism Dev. Disord. 33(4):449-454 (Aug. 2003) [Abstract Only].
Balasubramanian, Mukundh N. et al. Asparagine synthetase: regulation by cell stress and involvement in tumor biology, Am. J. Physiol. Endocrinol. Metab. 304(8):E789-E799 (Apr. 15, 2013).
Beliaev, O.A. The therapeutic efficacy of the triase preparation in experimental pancreatic exocrine insufficiency. Eksp Lin Farmakiol. 57:38-40 (1994) (Abstract Only—English Translation).
Chen, Li et al. Antibiotic effect of lysostaphin on granulation wound. Acta Academiae Medicinae Militaris Tertiae, 8(14) p. 1 Abstract (2006).
Co-pending U.S. Appl. No. 16/010,850, filed Jun. 18, 2018.
Co-pending U.S. Appl. No. 16/103,192, filed Aug. 14, 2018.
Coutinho, AM et al. Variants of the serotonin transporter gene (SLC6A4) significantly contribute to hyperserotonemia in autism. Mol Psychiatry. Mar. 2004;9(3):264-71.
Fafournoux, P. et al. Amino acid regulation of gene expression. Biochemical Journal, 351:1-12(2000).
Girella, E. et al. The assay of chymotrypsin in stool as a simple and effective test of exocrine pancreatic activity in cystic fibrosis. Pancreas, 3(3):254-262 (1988).
Hamel, E. et al. Effects of Cocaine on Rat Pancreatic Enzyme Secretion and Protein Synthesis, Digestive Diseases, 23(3):264-268 (Mar. 1978).
International Application No. PCT/US18/26841 International Search Report and Written Opinion dated Jul. 3, 2018.

(56) References Cited

OTHER PUBLICATIONS

Nestler, et al. Delta-FosB: A sustained molecular switch for addiction. PNAS 98(20): 11042-11046 (Sep. 25, 2001).
No Author. RSDSA, 2015: Telltale signs and symptoms of CRPS/RSD on the web at rsds.org/telltale-signs-and-symptoms-of-crpsrsd. [Accessed: Sep. 5, 2018].
O'Keefe, Stephen J.D. et al. The Exacerbation of Pancreatic Endocrine Dysfunction by Potent Pancreatic Exocrine Supplements in Patients with Chronic Pancreatitis. J. Clin. Gastroenterol. 32(4):319-323 (2001).
Felig, P. Amino acid metabolism in man. Annual Review of Biochemistry, 44(1):933-955 (1975). [Abstract Only].
Chez, M. et al. Secretin and autism: A two-part clinical investigation. Journal of Autism and Developmental Disorders, 30(2), 87-94 (Apr. 2000) [Abstract Only].
Evans, C. et al. Altered amino acid excretion in children with autism. Nutritional Neuroscience, 11(1):9-17 (Feb. 2008).
First, M.Structured clinical interview for DSM-IV-TR axis I disorders, research version, patient edition. (SCID-I/P) New York: Biometrics Research, New York State Psychiatric Institute. (2002).
Guesnet, P. et al. Docosahexaenoic acid (DHA) and the developing central nervous system (CNS)—Implications for dietary recommendations. Biochimie, 93(1):7-12(2011). [Abstract Only].
Heil, M., et al. Low endogenous fecal chymotrypsin: a possible biomarker for autism. Poster presented at the annual IMFAR Conference on Autism, Atlanta, GA.(May 2014) p. 1.
Matthews, D. Intestinal absorption of amino acids and peptides. Proceedings of the Nutrition Society, 31 (2):171-177(1972).
McClung, C.A. et al. DeltaFosB: A molecular switch for long-term adaptation in the brain. Molecular Brain Research, 132(2):146-154 (Dec. 20, 2004).
Morimoto, R. The heat shock response: Systems biology of proteotoxic stress in aging and disease. Cold Spring Harbor Symposia on Quantitative Biology, 76:91-99 (2011) (Epub: Feb. 27, 2012).
Munasinghe, S.A. et al. Digestive enzyme supplementation for autism spectrum disorders: A double-blind randomized controlled trial. Journal of Autism and Developmental Disorders, 40(9):1131-1138 (Sep. 2010) [Abstract Only].
Naushad, Shaik Mohammad et al. Autistic children exhibit distinct plasma amino acid profile. Indian Journal of Biochemistry and Biophysics, 50(5):474-478 (Oct. 2013).
Patton, J. et al. Factor structure of the barratt impulsiveness scale. Journal of Clinical Psychology, 51(6): 768-774 (Nov. 1995).
Robinson, T. et al. Incentive-sensitization and addiction. Addiction, 96(1):103-114 (Jan. 2001).
Schedl, H. et al. Absorption of l-methionine from the human small intestine. Journal of Clinical Investigation, 47(2): 417-425 (1968).
Rivest, J. et al. A dynamic model of protein digestion in the small intestine of pigs. Journal of Animal Science, 78(2):328-240 (Feb. 2000).
Singh, Manjit. Alcoholic pancreatitis in rats fed ethanol in a nutritionally adequate liquid diet. International Journal of Pancreatology, 2:311-324 (1987).
Avruch, J., et al. Amino acid regulation of TOR complex 1. AJP: Endocrinology and Metabolism, Am. J. Physiol. Endocrinol. Metab. 296(4):E592-E602 (Apr. 2009).
Daly, E., et al. Response inhibition and serotonin in autism: A functional MRI study using acute tryptophan depletion. Brain, 137(9), 2600-2610 (Sep. 2014).
Drabkin, H., et al. Initiation of protein synthesis in mammalian cells with codons other than AUG and amino acids other than methionine. Molecular and Cellular Biology, 18(9): 5140-5147 (Sep. 1998).
Fairclough, P. et al. Comparison of the absorption of two protein hydrolysates and their effects on water and electrolyte movements in the human jejunum. Gut, 21(10):829-834 (1980).
McClung, C., et al. Regulation of gene expression and cocaine reward by CREB and DeltaFosB. Nature Neuroscience, 6(11):1208-1215 (2003). [Abstract Only].
Nestler, E.J. Molecular basis of long-term plasticity underlying addiction. Nature Reviews Neuroscience, 2(2):119-128 (Feb. 2001).
Norton, L. et al. Leucine regulates translation initiation of protein synthesis in skeletal muscle after exercise. The Journal of Nutrition, 136(2):533S-537S (Feb. 2006).
Schain, RJ et al. Studies on 5-hydroxyindole metabolism in autistic and other mentally retarded children. J. Pediatr. 58:315-320 (1961) [Summary Only].
Tang, G. et al. Loss of mTOR-dependent macroautophagy causes autistic-like synaptic pruning deficits. Neuron, 83(5):1131-1143 (Sep. 3, 2014).
Williams, K. et al. Cochrane Review: Selective serotonin reuptake inhibitors (SSRIs) for autism spectrum disorders (ASD). Evidence-Based Child Health: A Cochrane Review Journal, 6(4):1044-1078 (Jul. 2011). [Abstract Only].
U.S. Appl. No. 12/054,343 Non-Final Office Action dated Dec. 26, 2017.
U.S. Appl. No. 12/535,676 Non-Final Office Action dated Sep. 6, 2018.
U.S. Appl. No. 12/786,739 Final Office Action dated Sep. 25, 2018.
U.S. Appl. No. 12/786,739 Non-Final Office Action dated Jan. 4, 2018.
U.S. Appl. No. 13/002,136 Advisory Office Action dated Jul. 9, 2018.
U.S. Appl. No. 13/002,136 Final Office Action dated Jan. 8, 2018.
U.S. Appl. No. 13/733,873 Final Office Action dated Feb. 21, 2018.
U.S. Appl. No. 13/836,135 Non-Final Office Action dated Mar. 15, 2018.
U.S. Appl. No. 14/296,091 Final Office Action dated Oct. 1, 2018.
U.S. Appl. No. 14/296,091 Non-Final Office Action dated Mar. 22, 2018.
U.S. Appl. No. 14/612,580 Notice of Allowability dated Mar. 1, 2018.
U.S. Appl. No. 14/612,580 Notice of Allowance dated Jan. 12, 2018.
U.S. Appl. No. 14/713,242 Non-Final Office Action dated Mar. 29, 2018.
U.S. Appl. No. 14/921,896 Final Office Action dated Jan. 25, 2018.
U.S. Appl. No. 14/921,896 Notice of Allowability dated Sep. 12, 2018.
U.S. Appl. No. 14/921,896 Notice of Allowance dated Jul. 18, 2018.
U.S. Appl. No. 15/089,842 Non-Final Office Action dated Jun. 26, 2018.
U.S. Appl. No. 15/164,493 Non-Final Office Action dated Feb. 27, 2018.
U.S. Appl. No. 15/265,415 Non-Final Office Action dated Apr. 11, 2018.
U.S. Appl. No. 15/265,620 Non-Final Office Action dated Jun. 20, 2018.
U.S. Appl. No. 15/593,121 Non-Final Office Action dated Mar. 8, 2018.
Yang, Xinyi et al. Advances in anti-staphylococcal agent lysostaphin. Chinese Journal of New Drugs 14(9):1113-1117 (2005).
American Family Physician. Cuts, Scrapes, and Stitches. Am Fam Physician 69(11):2647-2648 (Jun. 1, 2004).
Carroccio et al. Effectiveness of Enteric-coated Preparations on Nutritional Parameters in Cystic Fibrosis. Digestion 41:201-206 (1988).
Carroccio et al. Role of pancreatic impairment in growth recovery during gluten-free diet in childhood celiac disease. Gastroenterology 112:1839-1844 (1997).
Cermak, Sharon A. et al. Food selectivity and sensory sensitivity in children with autism spectrum disorders. J. Am. Diet Assoc. 110(2):238-246 (Feb. 2010).
Cichoke. Influenza. In: The Complete Book of Enzyme Therapy. Anthony J. Cichoke. Avery, a member of Penguin Putnam, Inc., publisher. Ed.: Dara Stewart, pp. 37, 40-45 (1999).
Cornish. A balanced approach towards healthy eating in autism, Journal of Human Nutrition and Dietetics 11:501-509 (1998).
Dudzinska. Dissertation. Development of lipid-based enteric coatings. Oct. 18, 1988. Martin Luther University, Halle-Wittenberg, pp. 1-125.

(56) References Cited

OTHER PUBLICATIONS

Durie et al. Uses and abuses of enzyme therapy in cystic fibrosis. Journal of the Royal Society of Medicine. 91 :(Suppl. 34):2-13 (1998).
Flament, M.P. et al. Development of 400 μm Pellets by Extrusion-Spheronization Application with Gelucire 50/02 to Produce a "Sprinkle" Form, Drug Development and industrial Pharmacy, 30:1, 43-51, DOI: 10.1081/DDC-120027510 (2004).
Ijuin, H. Evaluation of pancreatic exocrine function and zinc absorption in alcoholism. The Kurume Medical Journal 45.1 (1998): 1-5.
Johnson et al. Eating Habits and Dietary Status in Young Children with Autism. J Dev Phys Disabil 20:437-448 (2008).
Keller, et al. Pancreatic enzyme supplementation therapy. Current Treatment Options in Gastroenterology 6.5 (2003): 369-374.
Klopfleisch et al. Encephalitis in a stone marten (Martes foina) after natural infection with highly pathogenic avian influenza virus subtype H5N1. Journal of Comparative Pathology 137:155-159 (2007).
Koh et al. Inflammation and wound healing: The role of the macrophage. Expert Rev Mol Med. 13:e23 (Author manuscript).
Koivu et al. Determination of Phylloquinone in Vegetables, Fruits, and Berries by High-Performance Liquid Chromatography with Electrochemical Detection. J. Agric. Food Chem. 45(12):4644-4649 (1997).
Medori et al. Fatal Familial Insomnia, A Prion Disease With A Mutation At Condon 178 of The Prion Protein Case. N Engl J Med 326:444-449 (1992).
Munesue, et al. High prevalence of bipolar disorder comorbidity in adolescents and young adults with high-functioning autism spectrum disorder: a preliminary study of 44 outpatients. Journal of Affective Disorders 111.2-3 (2008): 170-175.
Qi, et al. Solubility and emulsifying properties of soy protein isolates modified by pancreatin. Journal of Food Science 62.6 (1997): 1110-1115.
Salpekar, et al. Bipolar Spectrum Disorder Comorbid With Autism Spectrum Disorder; Nadd Bulletin, vol. X, 2007. No. 6, Article 1, pp. 1-5, downloaded from http://www.thenadd.org/nadd-bulletin/archive/volunne-x/on Dec. 11, 2018.
Diagnostic and Statistical Manual of Mental Disorders, Fourth Edition, Primary Care Version, Chapter 6, American Psychiatric Association (2000).
U.S. Appl. No. 13/002,136 Non-Final Office Action dated Dec. 18, 2018.
U.S. Appl. No. 13/757,412 Office Action dated Apr. 16, 2019.
U.S. Appl. No. 13/836,135 Notice of Allowance dated Apr. 25, 2019.
U.S. Appl. No. 15/265,620 Non-Final Office Action dated Jan. 22, 2019.
U.S. Appl. No. 15/593,129 Office Action dated Jan. 3, 2019.
U.S. Appl. No. 12/535,676 Office Action dated Jun. 26, 2019.
U.S. Appl. No. 13/002,136 Office Action dated Jun. 21, 2019.
U.S. Appl. No. 12/786,739 Office Action dated May 8, 2019.
U.S. Appl. No. 13/733,873 Office Action dated May 16, 2019.
U.S. Appl. No. 15/074,115 Office Action dated Mar. 6, 2019.
U.S. Appl. No. 15/089,842 Notice of Allowance dated Mar. 29, 2019.
U.S. Appl. No. 15/265,415 Notice of Allowance dated Dec. 26, 2018.
U.S. Appl. No. 15/593,121 Notice of Allowance dated Dec. 26, 2018.
Cox, RJ et al. Influenza Virus: Immunity and Vaccination Strategies. Comparison of the Immune Response to Inactivated and Live, Attenuated Influenza Vaccines. Scandinavian Journal of Immunology 59, 1-15 (2004).
U.S. Appl. No. 13/836,135 Final Office Action dated Dec. 14, 2018.
U.S. Appl. No. 14/713,242 Final Office Action dated Jan. 9, 2019.
U.S. Appl. No. 15/089,842 Final Office Action dated Dec. 4, 2018.
U.S. Appl. No. 15/164,493 Notice of Allowance dated Nov. 15, 2018.
U.S. Appl. No. 15/354,940 Non-Final Office Action dated Nov. 2, 2018.
ABCNEWS. Changing Face of Autism: Numbers Rise as More Behaviors Included. ABCnews. Nov. 1, 2007.
Adams. "Summary of Defeat Autism Now! (DNN!) Oct. 2001 Conference," retrieved from the internet Dec. 18, 2008. http://puterakembara.org/rm/DAN2001.htm.
Advisory Action dated Jun. 3, 2008 for U.S. Appl. No. 10/681,018.
Aman, et al. Outcome measures for clinical drug trials in autism. CNS Spectr. Jan. 2004;9(1):36-47.
Amendment and Response dated Apr. 7, 2010 in Reply to Restriction Requirement dated Oct. 7, 2009 for U.S. Appl. No. 12/283,090.
Amendment and Response dated Jun. 30, 2010 to Restriction Requirement dated Jan. 13, 2010 for U.S. Appl. No. 12/487,868.
Amendment dated Oct. 20, 2008 in Reply to Notice Non-responsive Amendment dated Sep. 22, 2008 for U.S. Appl. No. 11/232,180.
Amendment dated Oct. 24, 2008 in Reply to Notice of Non-Responsive Amendment dated Sep. 25, 2008 for U.S. Appl. No. 11/555,697.
Amendment dated Oct. 28, 2009 in Reply to Final Office Action dated Apr. 28, 2009 for U.S. Appl. No. 10/681,018.
Amendment dated Nov. 13, 2009 in Reply to Final Office Action dated Jul. 27, 2004 for U.S. Appl. No. 09/990,909.
Amendment dated Nov. 17, 2007 in Reply to Restriction Requirement dated Oct. 17, 2007 for U.S. Appl. No. 11/555,697.
Amendment dated Dec. 12, 2007 in Reply to Office Action dated Aug. 8, 2007 for U.S. Appl. No. 11/213,382.
Amendment dated Dec. 7, 2007 in Reply to Office Action dated Aug. 7, 2007 for U.S. Appl. No. 10/681,018.
Amendment dated Feb. 2, 2004 in Reply to Office Action dated Jul. 29, 2003 for U.S. Appl. No. 09/990,909.
Amendment dated Feb. 29, 2008 in Reply to Notice of Non-Responsive Amendment dated Feb. 11, 2008 for U.S. Appl. No. 11/555,697.
Amendment dated Feb. 7, 2003 in Reply to Office Action dated Jul. 30, 2002 for U.S. Appl. No. 09/990,909.
Amendment dated Feb. 7, 2009 in Reply to Office Action dated Aug. 18, 2008 for U.S. Appl. No. 10/681,018.
Amendment dated Mar. 1, 2004 in Reply to Office Action dated Aug. 26, 2003 for U.S. Appl. No. 10/041,073.
Amendment dated Mar. 24, 2010 in Reply to Final Office Action dated Sep. 24, 2009 for U.S. Appl. No. 12/046,252.
Amendment dated Mar. 3, 2008 to Restriction Requirement dated Jan. 10, 2008 for U.S. Appl. No. 11/232,180.
Amendment dated Mar. 4, 2008 in Reply to Office Action dated Nov. 14, 2007 for U.S. Appl. No. 11/213,255.
Amendment dated May 18, 2007 in Reply to Office Action dated Dec. 22, 2006 for U.S. Appl. No. 10/681,018.
Amendment dated May 19, 2008 in Reply to Final Office Action dated Mar. 17, 2008 for U.S. Appl. No. 10/681,018.
Amendment dated May 27, 2009 in Reply to Final Office Action dated Feb. 27, 2009 for U.S. Appl. No. 11/555,697.
Amendment dated Jun. 15, 2009 in Reply to Final Office Action dated Mar. 13, 2009 for U.S. Appl. No. 11/232,180.
Amendment dated Jun. 8, 2007 in Reply to Restriction Requirement dated May 9, 2007 for U.S. Appl. No. 11/213,382.
Amendment dated Jun. 8, 2010 in Reply to Office Action dated Jan. 8, 2010 for U.S. Appl. No. 10/681,018.
Amendment dated Jul. 2, 2008 in Reply to Notice of Non-Compliant Amendment dated Jun. 2, 2008 for U.S. Appl. No. 12/046,252.
Amendment dated Aug. 19, 2009 in Reply to Notice Non-Compliant Amendment dated Jun. 19, 2009 for U.S. Appl. No. 11/232,180.
Amendment dated Aug. 21, 2008 in Reply to Office Action dated Apr. 21, 2008 for U.S. Appl. No. 11/232,180.
Amendment dated Aug. 28, 2008 in Reply to Office Action dated Mar. 28, 2008 for U.S. Appl. No. 11/555,697.
Amendment dated Sep. 24, 2007 in Reply to Restriction Requirement dated Jun. 22, 2007 for U.S. Appl. No. 11/213,255.
Amendment dated Sep. 25, 2008 in Reply to Final Office Action dated Jun. 25, 2008 for U.S. Appl. No. 11/213,255.
Amendment in Response dated May 23, 2003 to Restriction Requirement dated Apr. 23, 2003 for U.S. Appl. No. 09/990,909.

(56) References Cited

OTHER PUBLICATIONS

Ang, et al. Biological role and regulation of the universally conserved heat shock proteins. J Biol Chem. Dec. 25, 1991;266(36):24233-6.
Anonymous: Emulsifiers for the preparation of active dry yeast, Research Disclosure, Mason Publications, Hampshire, GB, 236(6), Dec. 1983 (attached).
APDA. Basic Information About Parkinson's Disease. Jul. 14, 2008.
Arribas, et al. A comparative study of the chymotrypsin-like activity of the rat liver multicatalytic proteinase and the ClpP from *Escherichia coli*. J Biol Chem. Oct. 5, 1993;268(28):21165-71.
Arrigo, et al. Expression of heat shock proteins during development in *Drosophila*. Results Probl Cell Differ. 1991;17:106-19.
ASH. Patient Information Guide—Understanding Hypertension. American Society of Hypertension. 2004. 1-7.
Ashwood, et al. Immune activation of peripheral blood and mucosal CD3+ lymphocyte cytokine profiles in children with autism and gastrointestinal symptoms. J Neuroimmunol. Dec. 19, 2005; 1-9.
Ashwood, et al. Intestinal lymphocyte populations in children with regressive autism: evidence for extensive mucosal immunopathology. J Clin Immunol. Nov. 2003;23(6):504-17.
Ashwood, et al. Spontaneous mucosal lymphocyte cytokine profiles in children with autism and gastrointestinal symptoms: mucosal immune activation and reduced counter regulatory interleukin-10. J Clin Immunol. Nov. 2004;24(6):664-73.
Austic. Development and adaptation of protein digestion. J Nutr. May 1985;115(5):686-97.
Autism Diagnosis. Autism Statistics. Www.autism-diagnosis.com/autism_statistics/autism_statistics.html. 2007.
Autism Society of America. Incidence Numbers from Other Countries, www.autism-society.org. Accessed: Jul. 14, 2008.
Awazuhara, et al. Antigenicity of the proteins in soy lecithin and soy oil in soybean allergy. Clin Exp Allergy. Dec. 1998;28(12):1559-64.
Axcan Pharma Inc. Cdn Prescribing Information on VIOKASE Pancrelipase, USP tablets, powder. 2000: 1-3.
Axelrod. Secretin Treatment for Gastrointestinal Dysmobility in Patients with Familial Dysautonomia. New York University School of Medicine, Grant Recipient awards, Mar.-May 2000. www.med.nyu.edu/ogars/awards/awards2000/page2.html.
Azilect et al. "Correlation between protein intake and daily levodopa dosage," Obtained from the internet May 2, 2007, http://www.azilect.eu/media/cnsnews/showitem.aspx?i=d1c603e4-3c61-4aa1-a376-6e519a5a0f80.
Bailey, et al. Co-occurring conditions associated with FMR1 gene variations: findings from a national parent survey. Am J Med Genet A. Aug. 15, 2008;146A(16):2060-9.
Bakkaloglu, et al. Atopic features in early childhood autism. Eur J Paediatr Neurol. Nov. 2008;12(6):476-9.
Barlow. A comparison of the blood pressure, kidney volume and the pancreatic secretory response following the vein administration of various secretin preparations. Am J Phys. 1927;81:182-188.
Barnhart, et al. Symptomatic granular cell tumor involving the pituitary gland in a dog: a case report and review of the literature. Vet Pathol. May 2001;38(3):332-6.
Beilmann, et al. Neoexpression of the c-met/hepatocyte growth factor-scatter factor receptor gene in activated monocytes. Blood. Dec. 1, 1997;90(11):4450-8.
Bellanti, et al. Abnormalities of Th1 function in non-IgE food allergy, celiac disease, and ileal lymphonodular hyperplasia: a new relationship? Ann Allergy Asthma Immunol. Jun. 2003;90(6 Suppl 3):84-9.
Belmonte et al. Fragile X syndrome and autism at the intersection of genetic and neural networks. Nat Neurosci. Oct. 2006; 9(10): 1221-5 (abstract only).
Berg, et al. Section 10.5 Many Enzymes Are Actived by Specific Proteolytic Cleavage. 2002.
Berg, et al. Section 9.1 Proteases: Facilitating a Difficult Reaction. 2002.
Berg, et al. Table of Contents. Biochemistry, 5th edition. 2002.

Birnbaum, et al. Heat shock or stress proteins and their role as autoantigens in multiple sclerosis. Ann N Y Acad Sci. Dec. 19, 1997;835:157-67. Abstract only.
Blackmer. Parkinson disease: treatment and medication. Mar. 10, 2009., retrieved from the internet on Sep. 15, 2009, http://emedicine.medscape.com/article/312519-treatment.
Block, et al. A rapid food screenerto assess fat and fruit and vegetable intake. Am J Prev Med. May 2000;18(4):284-8.
Blog. Acid Phosphatase Research (blog). Acid-phosphatase.blogspot.com. 2008.
Bode et al. Usefulness of a simple photometric determination of chymotrypsin activity in stools-results of a multicentre study. Clin Biochem. 1986; 19:333-37.
Boorom. Is this recently characterized gastrointestinal pathogen responsible for rising rates of inflammatory bowel disease (IBD) and IBD associated autism in Europe and the United States in the 1990s? Med Hypotheses. 2007;69(3):652-9.
Borlongan. Recent preclinical evidence advancing cell therapy for Alzheimer's disease. Exp Neurol. Sep. 2012;237(1):142-6. doi: 10.1016/j.expneurol.2012.06.024. Epub Jun. 27, 2012.
Borowitz et al., Study of a novel pancreatic enzyme replacement therapy in pancreatic insufficient subjects with cystic fibrosis J.Pediatr., 149:658-662 (2006).
Borowitz, et al. Use of pancreatic enzyme supplements for patients with cystic fibrosis in the context of fibrosing colonopathy. Consensus Committee. J Pediatr. Nov. 1995;127(5):681-4.
Bowen. Exocrine secretions of the pancreas. Jul. 5, 2006. Accessed online at www.vivo.colostate.edu/hbooks/pathphys/digestion/pancreas/exocrine.html.
Boyd, et al. Positively charged amino acid residues can act as topogenic determinants in membrane proteins. Proc Natl Acad Sci U S A. Dec. 1989;86(23):9446-50.
Bradstreet, et al. Detection of Measles Virus Genomic RNA in Cerebrospinal Fluid of Children with Regressive Autism: a Report of Three Cases. J. Am Phys Surg. 2004; 9(2):38-45.
Bray, et al. Effect of dietary protein content on weight gain, energy expenditure, and body composition during overeating. A randomized controlled trial. JAMA. Jan. 4, 2012; 307(1):47-55.
Brinkley, et al. Factor analysis of the aberrant behavior checklist in individuals with autism spectrum disorders. J Autism Dev Disord. Nov. 2007;37(10):1949-59. Epub Dec. 21, 2006.
Brown. Background to Parkinson's Disease, biomed.brown.edu. Jul. 14, 2008.
Brudnak et al. Enzyme-based therapy for autism spectrum disorders—is it worth another look? Med Hypoth. 2002; 58:422-428.
"Brudnak, Mark et al., Guide to intestinal health in autism spectrum disorder, Kirkman Laboratories, (Oct. 2001)".
Bruhat, et al. Amino acid limitation induces expression of CHOP, a CCAAT/enhancer binding protein-related gene, at both transcriptional and post-transcriptional levels. J Biol Chem. Jul. 11, 1997;272(28):17588-93.
Button, KS et al. Power failure: why small sample size undermines the reliability of neuroscience. Nat. Rev. Neurosci. 14:365376 (2013).
Calderon-Garciduenas, et al. Immunotoxicity and environment: immunodysregulation and systemic inflammation in children. Toxicol Pathol. 2009;37(2):161-9.
Caldwell, et al. Crystalline Pancreatic Amylase. II. Improved Method for its Preparation from Hog Pancreas Glands and Additional Studies of its Properties. J. Am. Chem. Soc. 1952; 74(16):4033-4035.
Campbell et al. A genetic variant that disrupts MET transcription is associated with autism. Proc Natl Acad Sci USA. 2006; 103(45):16834-16839.
Campbell, et al. Distinct genetic risk based on association of MET in families with cooccurring autism and gastrointestinal conditions. Pediatrics. Mar. 2009;123(3):1018-24.
Carlton. Autism and malnutrition: the milk connection. Retrieved from the internet on Feb. 18, 2008, http://www.mercola.com/2004/autism_malnutrition.htm.
Caronna, et al. Autism spectrum disorders: clinical and research frontiers. Arch Dis Child. Jun. 2008;93(6):518-23.

(56) References Cited

OTHER PUBLICATIONS

Carroccio, et al. Pancreatic enzyme therapy in childhood celiac disease. A double-blind prospective randomized study. Dig Dis Sci. Dec. 1995;40(12):2555-60.
Carroccio, et al. Secondary impairment of pancreatic function as a cause of severe malabsorption in intestinal giardiasis: a case report. Am J Trap Med Hyg. Jun. 1997;56(6):599-602.
Carroccio, et al. Secretin-cerulein test and fecal chymotrypsin concentration in children with intestinal giardiasis. Int J Pancreatol. Oct. 1993;14(2):175-80.
Cassidy, et al. A new concept for the mechanism of action of chymotrypsin: the role of the low-barrier hydrogen bond. Biochemistry. Apr. 15, 1997;36(15):4576-84.
CDC. Attention-Deficit/Hyperactivity Disorder (ADHD). Www.cdc. org. 2005.
CDC. Autism Information Center/FAQs. Dept of Health and Human Services/CDC. Jan. 30, 2008.
CDC, *Escherichia coli*, Travelers Health, Chapter 3: Infectious Diseases Related to Travel, Jul. 10, 2015, Available Online at: wwwnc.cdc.gov/travel/yellowbook/2016/infectious-diseases-related-to-travel/escherichia-coli.
CDC. High Blood Pressure. Division for Heart Disease Stroke Prevention. Jul. 15, 2003.
Chaignon et al. Susceptibility of staphylococcal biofilms to enzymatic treatments depends on their chemical compositions. Appl. Microbiol. Appl. Microbiol. 75:125-132 (2007).
Chazalette, J.P. et al., A double-bind placebo-controlled trial of a pancreatic enzyme formulation (Panzytrat 25000) in the treatment of impaired lipid digestion in patients with cystic fibrosis. Drug Invest., 5(5):274-280 (1993).
Chen, et al. Identification of two lysosomal membrane glycoproteins. J Cell Biol. Jul. 1985;101(1):85-95.
Chen, et al. Lysine 43 is trimethylated in subunit C from bovine mitochondrial ATP synthase and in storage bodies associated with batten disease. J Biol Chem. May 21, 2004;279(21):21883-7.
Chen, et al. Medicinal Functions of Bromelain and Its Application Prospect in Animal Husbandry, China Animal Husbandry & Veterinary Medicine. 2005; vol. 32, No. 1, p. 14-16. (in Chinese with English translation).
Childhood Autism Rating Scale (CARS), Wikipedia, downloaded May 5, 2014.
Cichoke, AJ The Complete Book of Enzyme Therapy, Penguin (1999) pp. 206-208 and 38.
Cichoke. Celiac disease. The complete book of enzyme therapy. Penguin. New York, NY. 1999; 174-177.
Cichoke, et al. The complete book of enzyme therapy. Penguin. 1998: 39, 42, 47, 50, and 53.
Cichoke. Influenza. In: The Complete Book of Enzyme Therapy. D. Stewart, ed. Copyright 1999. Anthony J. Cichoke. Penquin Putnam, Inc., New York, New York. pp. "Contents", 50, 273-275 and 455.
Claud, et a. Hypothesis: inappropriate colonization of the premature intestine can cause neonatal necrotizing enterocolitis. FASEB J. Jun. 2001;15(8):1398-403.
Cohn. Optimizing the Effectiveness of Pancreatic Enzyme Replacement Therapy (PERT). Clinical Impressions. Sep. 1, 2009; 1-4.
Commentary on the Japanese Pharmacopoeia, 14th ed., D929-D931, 2001.
Concerta. ADHD Myths and Facts. ADHD Myths and Facts about medication, girls, and symptoms and causes. Concerta.net. Jul. 15, 2008.
Co-pending U.S. Appl. No. 15/593,121, filed May 11, 2017.
Co-pending U.S. Appl. No. 15/593,124, filed May 11, 2017.
Co-pending U.S. Appl. No. 15/593,129, filed May 11, 2017.
Corring, et al. Development of digestive enzymes in the piglet from birth to 8 weeks. I. Pancreas and pancreatic enzymes. Nutr Metab. 1978;22(4):231-43.
Couet, et al. Identification of peptide and protein ligands for the caveolin-scaffolding domain. Implications for the interaction of caveolin with caveolae-associated proteins. J Biol Chem. Mar. 7, 1997;272(10):6525-33.

Coyle. Treating the Negative Symptoms of Schizophrenia: An Expert Interview with Joseph Coyle, MD. www.narsad.org/?q=node/438/latest-research. 2006.
Craig, et al. Heat shock proteins: molecular chaperones of protein biogenesis. Microbiol Rev. Jun. 1993;57(2):402-14.
Creon—FDA Prescribing information side effects and uses. Revised Apr. 2015.
Creon digestive enzymes. Celic.com/Jun. 2009. http://www.celiac.com/gluten-free/topic/59195-creon-digestive-enzymes.
Creon. Full prescribing information. Last edited Mar. 2013. Abbvie Inc 2012. www.rxabbvie.com/pdf/creon_PI.pdf.
Croonenberghs, et al. Peripheral markers of serotonergic and noradrenergic function in post-pubertal, caucasian males with autistic disorder. Neuropsychopharmacology. Mar. 2000;22(3):275-83.
Cruse et al. Illustrated dictionary of immunology. CRC Press, New York. 1995.
Cuervo, et al. Cathepsin A regulates chaperone-mediated autophagy through cleavage of the lysosomal receptor. EMBO J. Jan. 2, 2003;22(1):47-59.
Curemark press release. Curemark Receives Investigational New Drug Clearance For CM-AT For Autism. Mar. 26, 2009. http://www.medicalnewstoday.com/releases/143723.php.
Dajcs, et al. Lysostaphin is effective in treating methicillin-resistant *Staphylococcus aureus* endophthalmitis in the rabbit. Curr Eye Res. Jun. 2001;22(6):451-7.
Darman. An introduction to alternative medicine for psychiactric conditions. Oct. 22, 2007, retrieved on Sep. 18, 2009, http://web.archive.org/web/20071022104238/http://altp[therapies4bipolar.info/ortho/html.
Dawe, et al. Antipsychotic drugs dose-dependently suppress the spontaneous hyperactivity of the chakragati mouse. Neuroscience. Nov. 24, 2010;171(1):162-72. Epub Sep. 17, 2010.
Dawe, et al. The chakragati mouse: a mouse model for rapid in vivo screening of antipsychotic drug candidates. Biotechnol J. Nov. 2007;2(11):1344-52.
Dawn. Autism: the Latest Prevalence Rates in USA—Now 1 in 175. Disabled Women's Network Ontario. Dawn.thot.net/autism2.html. 2006.
Dawson lab. Research Projects in Synthetic Protein Chemistry. 2005; 1-2.
Delong. News on Parkinson's. The Dana Foundation. Jul. 14, 2008.
DeMasi, Carl B. The Role of Enzymatic Detergents in Washing Medical Devices and Removing Contaminants from Them, National Diet 73:28-35 (May 2002).
Derwent. English abstract for RU 2286785 Nov. 10, 2006. Downloaded from the Derwent file Jul. 13, 2011.
Diaz-Hernandez, et al. Neuronal induction of the immunoproteasome in Huntington's disease. J Neurosci. Dec. 17, 2003;23(37):11653-61.
Digestive Enzyme Preparation: Pancreatin listed in Japanese Pharmacopoeia, Aug. 2008,< URL:http:>(in Japanese with English translation)</URL:http:>.
Digestive Enzyme Wikipedia. Retrieved from the internet Sep. 10, 2009, http://en.wikipedia.org/wiki/Digestive_enzyme.
Ding, et al. Proteasome inhibition in oxidative stress neurotoxicity: implications for heat shock proteins. J Neurochem. May 2001;77(4):1010-7.
Dobbs et al. Link between helicobacter pylori infection and idiopathic parkinsonism. Medical Hypothsis. 2000; 55(2):93-98.
Dockter et al. Determination of chymotrypsin in the feces by a new photometric method. Padiatr Padol. 1985; 20(3):257-265.
Dominquez-Munoz, et al. Optimising the therapy of exocrine pancreatic insufficiency by the association of a proton pump inhibitor to enteric coated pancreatic extracts. Gut. Jul. 2006;55(7):1056-7.
Dupiereux, et al. Creutzfeldt-jakob, Parkinson, lewy body dementia and Alzheimer diseases: from diagnosis to therapy. Cent Nerv Syst Agents Med Chem. Mar. 2009;9(1):2-11.
Eaves, et al. The criterion-related validity of the Childhood Autism Rating Scale and the Autism Behavior Checklist. J Abnorm Child Psychol. Oct. 1993;21(5):481-91. abstract only.
Edelson, et al. 3-Cyclohexene-1-glycine, an Isoleucine Antagonist. J. Am. Chem. Soc. 1958; 80(11):2698-2700.

(56) References Cited

OTHER PUBLICATIONS

Elkashef, et al. Biological markers of cocaine addiction: implications for medications development. Addict Biol. Jun. 2003;8(2):123-39.
Elphick, et al. Impaired luminal processing of human defensin-5 in Crohn's disease: persistence in a complex with chymotrypsinogen and trypsin. Am J Pathol. Mar. 2008;172(3):702-13.
Emc, Creon 10000 Capsules, May 18, 2015, Available Online at: www.medicines.org.uk/emc/medicine/2068.
EMedExpert, Antibiotics:Cephalosporins, Available online at: www.emedexpert.com/compare/cephalosporins.shtml, available as early as Jun. 2, 2007 per Internet Archive Wayback Machine.
Ethridge, et al. Acute pancreatitis results in induction of heat shock proteins 70 and 27 and heat shock factor-1. Pancreas. Oct. 2000;21(3):248-56.
Evans, et al. Pancreatic insufficiency in adult celiac disease: do patients require long-term enzyme supplementation? Dig Dis Sci. Oct. 2010;55(10):2999-3004. doi: 10.1007/s10620-010-1261-y. Epub May 11, 2010.
Exocrine Pancreatic Insufficiency (Enzymes) Document downloaded online on Jan. 8, 2016 at: http://www.epi4dogs.com/enzyme.htm< http:></http:>.
Fafournoux, et al. Amino acid regulation of gene expression. Biochem J. Oct. 1, 2000 ;351(Pt 1):1-12.
Fallingborg, et al. Measurement of gastrointestinal pH and regional transit times in normal children. J Pediatr Gastroenterol Nutr. Aug. 1990;11(2):211-4.
Fallon. Could one of the most widely prescribed antibiotics amoxicillin/clavulanate "augmentin" be a risk factor for autism? Med Hypotheses. 2005;64(2):312-5.
Family Caregiver Alliance. Fact Sheet: Parkinson's Disease. Caregiver.org. Jul. 14, 2008.
Fernell, et al. No evidence for a clear link between active intestinal inflammation and autism based on analyses of faecal calprotectin and rectal nitric oxide. Acta Paediatr. Jul. 2007;96(7):1076-9.
Ferrone, et al. Pancreatic enzyme pharmacotherapy. Pharmacotherapy. 2007; 27:910-920.
Fido, et al. Olanzapine in the treatment of behavioral problems associated with autism: an open-label trial in Kuwait. Med Prine Pract. 2008;17(5):415-8. doi: 10.1159/000141508. Epub Aug. 6, 2008.
Filipek et al. The screening and diagnosis of autistic spectrum disorders. J. of Autism and Dev Disorders. 1999; 29(6).
Final Office Action dated Jan. 3, 2012 for U.S. Appl. No. 10/681,018.
Final Office Action dated Jan. 26, 2012 for U.S. Appl. No. 12/487,864.
Final Office Action dated Nov. 8, 2011 for U.S. Appl. No. 12/054,343.
Final Office Action dated Nov. 8, 2011 for U.S. Appl. No. 12/786,739.
Final Office Action dated Nov. 9, 2010 for U.S. Appl. No. 09/990,909.
Final Office Action dated Feb. 14, 2011 for U.S. Appl. No. 12/049,613.
Final Office Action dated Feb. 27, 2009 for U.S. Appl. No. 11/555,697.
Final Office Action dated Mar. 13, 2009 for U.S. Appl. No. 11/232,180.
Final Office Action dated Mar. 17, 2008 for U.S. Appl. No. 10/681,018.
Final Office Action dated Apr. 28, 2009 for U.S. Appl. No. 10/681,018.
Final Office Action dated May 11, 2010 for U.S. Appl. No. 11/555,697.
Final Office Action dated Jun. 25, 2008 for U.S. Appl. No. 11/213,255.
Final Office Action dated Jul. 2, 2010 for U.S. Appl. No. 12/046,252.
Final Office Action dated Jul. 27, 2004 for U.S. Appl. No. 09/990,909.
Finegold et al. Gastrointestinal microflora studies in late-onset autism. Clinical Infectious Diseases. 2002; 35(1):S6-S15.
Fitzsimmons, et al. High-dose pancreatic-enzyme supplements and fibrosing colonopathy in children with cystic fibrosis. N Engl J Med. May 1, 1997;336(18):1283-9.
Fliri, et al. Drug effects viewed from a signal transduction network perspective. J Med Chem. Dec. 24, 2009;52(24):8038-46. doi: 10.1021/jm901001p.
Frossard, et al. Both thermal and non-thermal stress protect against caerulein induced pancreatitis and prevent trypsinogen activation in the pancreas. Gut. Jan. 2002;50(1):78-83.
Frossard. Trypsin activation peptide (TAP) in acute pancreatitis: from pathophysiology to clinical usefulness. JOP. Mar. 2001;2(2):69-77.
Furlano, et al. Colonic CD8 and gamma delta T-cell infiltration with epithelial damage in children with autism. J Pediatr. Mar. 2001;138(3):366-72.
Garcia et al. Detection of giardia lamblia, entamoeba histolytica/entamoeba dispar, and cryptosporidium parvum antigens in human fecal specimens using the triage parasite panel enzyme immunoassay. Am Soc for Microbiology. 2000; 38(9):3337-3340.
Gardner. Absorption of intact peptides: studies on transport of protein digests and dipeptides across rat small intestine in vitro. Q J Exp Physiol. Oct. 1982;67(4):629-37.
Garner Jr, et al. Porcine Pancreatic Lipase—A Glycoprotein. J Biol Chem. Jan. 25, 1972;247(2):561-5.
Gass, et al. Enhancement of dietary protein digestion by conjugated bile acids. Gastroenterology. Jul. 2007;133(1):16-23.
Generation Rescue. Autism and Vaccines Around the World: Vaccine Schedules, Autism Rates, and Under 5 Mortality. Apr. 1, 2009.
Giglio, et al. Failure to thrive: the earliest feature of cystic fibrosis in infants diagnosed by neonatal screening. Acta Paediatr. Nov. 1997;86(11):1162-5.
GM Chemie 2010 "Products: Hypromellose Phthalate" accessed from www.gmchemie.com on Sep. 22, 2014.
Goff, et al. Production of abnormal proteins in *E. coli* stimulates transcription of Ion and other heat shock genes. Cell. Jun. 1985;41(2):587-95.
Gonzalez, et al. Endoscopical, histological and immunological characteristics of the digestive mucosa in autistic children with gastrointestinal symptoms. 2005; 1-7.
Green, et al. Amino-terminal polymorphisms of the human beta 2-adrenergic receptor impart distinct agonist-promoted regulatory properties. Biochemistry. Aug. 16, 1994;33(32):9414-9.
Gupta, et al. Th1- and Th2-like cytokines in CD4+ and CD8+ T cells in autism. J Neuroimmunol. May 1, 1998;85(1):106-9.
Hadjivassiliou, et al. Does cryptic gluten sensitivity play a part in neurological illness? Lancet. Feb. 10, 1996;347(8998):369-71.
Happe et al. The neuropsychology of autism. Brain. 1996; 119:1377-1400.
Happe et al. Time to give up on a simple explanation for autism. Nat Neurosci. Oct. 2006; 9(10):1218-20.
HEALTH.com. Who is affected by Parkinson's disease, www.health.com. Jul. 14, 2008.
Heijerman, et al. Omeprazole enhances the efficacy of pancreatin (pancrease) in cystic fibrosis. Ann Intern Med. Feb. 1, 1991;114(3):200-1.
Hendren et al. Mechanistic biomarkers for autism treatment. Medical Hypotheses. 2009; 73:950-954.
Hitti. Allergy, celiac disease, and ileal lymphonodular. WebMD. 2005. 1-2.
Holquist et al. FDA safety page: Delayed-release vs. extended release Rxs. Drug Topics [online] Jul. 23, 2007 [Retrieved on Jul. 30, 2012] Retrieved from the internet: http://drugtopics.modernmedicine. com/drugtopics/Top+News/FDA-safety-page-Delayed-release-vs-extended-release/ArticleStandard/Article/detail/442606.
Holten, et al. Appropriate prescribing of oral beta-lactam antibiotics. Am Fam Physician. Aug. 1, 2000;62(3):611-20.
Horvath, et al. Autism and gastrointestinal symptoms. Curr Gastroenterol Rep. Jun. 2002;4(3):251-8.
Horvath, et al. Autistic disorder and gastrointestinal disease. Curr Opin Pediatr. Oct. 2002;14(5):583-7.
Horvath, et al. Gastrointestinal abnormalities in children with autistic disorder. J Pediatr. Nov. 1999;135(5):559-63.
Horvath et al. Improved social and language skills after secretin administration in patients with autistic spectrum disorders. Journal of the Association for Academic Minority Physicians. Jan. 1998; 9(1):9-15.
Hoshiko et al. The effect of the gastrointestinal hormones on colonic muscosal blood flow. Acta Medica Nagasakiensia. 1994; 39(4):125-130.
Houston. Autism—One Conference. May 2006. 1-83.

(56) References Cited

OTHER PUBLICATIONS

Hsiao, et al. The microbes of the intestine: an introduction to their metabolic and signaling capabilities. Endocrinol Metab Clin North Am. Dec. 2008;37(4):857-71.
Huang, et al. Apoptotic cell death in mouse models of GM2 gangliosidosis and observations on human Tay-Sachs and Sandhoff diseases. Hum Mol Genet. Oct. 1997;6(11):1879-85.
Huang, et al. Mapping of the human APOB gene to chromosome 2p and demonstration of a two-allele restriction fragment length polymorphism. Proc Natl Acad Sci U S A. Feb. 1986;83(3):644-8.
Information of Papain from Worthington Enzymes webpage http://www.worthington-biochem.com/pap/default.html Downloaded Jan. 17, 2013.
International preliminary report on patentability dated Jul. 17, 2014 for PCT/US2013/020183.
International search report and written opinion dated Feb. 21, 2013 for PCT/US2013/020183.
International search report and written opinion dated May 9, 2013 for PCT/US2013/024453.
International search report and written opinion dated Aug. 27, 2013 for PCT/US2013/043444.
International search report and written opinion dated Nov. 12, 2012 for PCT/US2012/034489.
International search report and written opinion dated Jan. 18, 2011 for PCT/US2010/057341.
International search report and written opinion dated Feb. 15, 2011 for PCT/US2010/053484.
International search report and written opinion dated Mar. 2, 2010 for PCT/US2010/020253.
International search report and written opinion dated Jun. 9, 2010 for PCT/US2010/030895.
International search report and written opinion dated Sep. 25, 2009 for PCT/US2009/049374.
International search report and written opnion dated Mar. 5, 2010 for PCT/US2010/020259.
International search report dated Mar. 11, 2002 for PCT/US2001/25343.
International search report dated Jun. 29, 2001 for PCT/US2000/34000.
Isaksson, et al. Pain reduction by an oral pancreatic enzyme preparation in chronic pancreatitis. Digestive Dis. Sci. 1983; 28(2):97-102.
James, et al. Thimerosal neurotoxicity is associated with glutathione depletion: protection with glutathione precursors. Neurotoxicology. 2004; 26(1):1-8.
Jeffrey. Global burden of hypertension may reach 1.5 billion by 2025. Medscape Medical News. Jul. 14, 2008.
Jenkins, et al. Management of gastroenteritis. Archives of Disease in Childhood. 1990; 65:939-941.
Juhl. Fibromyalgia and the serotonin pathway. Altern Med Rev. 1998; 3(5):367-375.
Jyonouchi, et al. Dysregulated innate immune responses in young children with autism spectrum disorders: their relationship to gastrointestinal symptoms and dietary intervention. Neuropsychobiology. 2005;51 (2):77-85.
Jyonouchi, et al. Evaluation of an association between gastrointestinal symptoms and cytokine production against common dietary proteins in children with autism spectrum disorders. J Pediatr. May 2005;146(5):605-10.
Jyonouchi, et al. Proinflammatory and regulatory cytokine production associated with innate and adaptive immune responses in children with autism spectrum disorders and developmental regression. J Neuroimmunol. Nov. 1, 2001;120(1-2):170-9.
Kachrimanis, et al. Tensile strength and disintegration of tableted silicified microcrystalline cellulose: influences of interparticle bonding. J Pharm Sci. Jul. 2003;92(7):1489-501.
Kaemmerer, et al. Effects of lipid peroxidation-related protein modifications on RPE lysosomal functions and POS phagocytosis. Invest Ophthalmol Vis Sci. Mar. 2007;48(3):1342-7.

Kaminski, et al. Polymorphism of bovine beta-casein and its potential effect on human health. J Appl Genet. 2007;48(3):189-98.
Kaspar et al. New photometric assay for chymotrypsin in stool. Clinical Chemistry. 1984; 30(11):1753-1757.
Katritos. New finding may have implications for schizophrenia, autism. Autism/Schizophrenia findings relating to protein, etc. Feb. 10, 2011. e-mail.
Kearney, et al. Global burden of hypertension: analysis of worldwide data. Lancet. Jan. 15-21, 2005 ;365(9455):217-23. Abstract only.
Kidd, P.M., Autism, an extreme challenge to integrative medicine. Part 2: medical management. Altern. Med. Rev., 7(6):172-499 (Dec. 2002).
King, et al. Effects of bacterial microflora of the lower digestive tract of free-range waterfowl on influenza virus activation. Appl Environ Microbiol. Jun. 2011;77(12):4119-25. doi: 10.1128/AEM.02578-10. Epub Apr. 29, 2011.
Knivsberg, et al. A randomised, controlled study of dietary intervention in autistic syndromes. Nutr Neurosci. Sep. 2002;5(4):251-61.
Kokai-Kun, et al. Lysostaphin as a treatment for systemic *Staphylococcus aureus* infection in a mouse model. J Antimicrob Chemother. Nov. 2007;60(5):1051-9. Epub Sep. 10, 2007.
Koller, et al. Falls and Parkinson's Disease (Abstract). Clin Neuropharmacol. 1989; 12(2):98-105.
Koplin, et al. Soy consumption is not a risk factor for peanut sensitization. J Allergy Clin Immunol. Jun. 2008;121(6):1455-9.
Koster et al. Evidence based medicine and extradigestive manifestations of helocobacter pylori. Acta Gastro-Enterologica Belgica. 2000; 63(4):388-392.
Krishnaswami, et al. A systematic review of secretin for children with autism spectrum disorders. Pediatrics. May 2011;127(5):e1322-5. doi: 10.1542/peds.2011-0428. Epub Apr. 4, 2011.
Kronenberg, et al. Folate deficiency induces neurodegeneration and brain dysfunction in mice lacking uracil DNA glycosylase. J Neurosci. Jul. 9, 2008;28(28):7219-30.
Kujoth, et al. Mitochondrial DNA mutations, oxidative stress, and apoptosis in mammalian aging. Science. Jul. 15, 2005;309(5733):481-4.
Kumar. Neurologic presentations of nutritional deficiencies. Neurol Clin. Feb. 2010;28(1):107-70.
Larimore. How Common Is ADHD? Facts About ADHD. Jul. 15, 2008.
Lashkari, et al. Williams-Beuren syndrome: An update and review for the primary physician. Clinical Pediatrics. 1999; 38(4):189-208.
Layer et al. Pancreatic enzyme replacement therapy. Current Gastroenterology Reports. 2001;3:101-108.
Lebenthal, et al. Enzyme therapy for pancreatic insufficiency: present status and future needs. Pancreas. Jan. 1994;9(1):1-12.
Leeds, et al. Is exocrine pancreatic insufficiency in adult coeliac disease a cause of persisting symptoms? Aliment Pharmacol Ther. Feb. 1, 2007 ;25(3):265-71.
Levy, et al. Relationship of dietary intake to gastrointestinal symptoms in children with autistic spectrum disorders. Biol Psychiatry. Feb. 15, 2007;61 (4):492-7.
Leyfer, et al. Comorbid psychiatric disorders in children with autism: interview development and rates of disorders. J Autism Dev Disord. Oct. 2006;36(7):849-61.
Lieberman. Pharmaceutical Dosage Forms. vol. 2: Disperse Systems. New York Marcel Dekker, Inc. 1996; 243-258.
Life Plus Somazyne accessed Jun. 10, 2016, Online at www.lifeplus.com/media/pdf/piSheets/US/6141-PI_EN.pdf.
Lipase 30, Technical Data sheet, 1 page, Scientific Protein Laboratories LLC Jun. 13, 2005.
Liyanage, et al. Bioavailability of iron from micro-encapsulated iron sprinkle supplement. Food and Nutrition bulletin. 2002; 23(3):133-137.
Lloyd. Lysosome membrane permeability: implications for drug delivery. Adv Drug Deliv Rev. Mar. 30, 2000;41(2):189-200.
Loh, et al. Highly tolerated amino acid substitutions increase the fidelity of *Escherichia coli* DNA polymerase I. J Biol Chem. Apr. 20, 2007;282(16):12201-9.

(56) References Cited

OTHER PUBLICATIONS

Lord, et al. Diagnostic Instruments in Autistic Spectrum Disorders, info.med.yale.edu. 2005; 11:730-771.
Luedtke, et al. Cathepsin A is expressed in a cell- and region-specific manner in the testis and epididymis and is not regulated by testicular or pituitary factors. J Histochem Cytochem. Aug. 2000;48(8):1131-46.
MacDonald. Thyrotoxicosis treated with pancreatic extract and iodine. Lancet. 1943; 244(6251)788.
Macfabe, et al. Neurobiological effects of intraventricular propionic acid in rats: possible role of short chain fatty acids on the pathogenesis and characteristics of autism spectrum disorders. Behav Brain Res. 2006;176(1):149-69.
Macready. Parkinson's Diseasne Treatment: what you should know. Retrieved from the internet on Sep. 15, 2009, http://www.everydayhealth.com/parkinsons-disease-treatment-overview.aspx.
Mannino, et al. Surveillance for asthma—United States, 1960-1995. MMWR CDC Surveill Summ. Apr. 24, 1998;47(1):1-27.
Marcus, et al. A placebo-controlled, fixed-dose study of aripiprazole in children and adolescents with irritability associated with autistic disorder. J Am Acad Child Adolesc Psychiatry. Nov. 2009;48(11):1110-19.
Marczewska et al. Protein intake in parkinsonian using the EPIC food frequency questionnaire. Mov Diord. Aug. 2006; 21(8):1229-1231.
Marion et al., A New Procedure Allowing the Complete Removal and Prevention of Hemodialysis. Blood Purification, 23:339-348 (2005).
Marlicz et al. Determination of chymotrypsin in the stool in the diagnosis of chronic pancreatitis. Wiadomosci lekarskie. 1988; 41(11)704-707. (in Polish with English abstract/summary).
Marsh. Neuropsychiatric aspects of parkinson's disease. Psychosomatics. 2000; 41(1):15-23.
Martin, et al. A rapid and sensitive spectrophotometric method for the assay of chymotrypsin. Biol Chem. Feb. 1959;234(2):294-8.
Matikainen, et al. Autonomic dysfunction in long-standing alcoholism. Alcohol Alcohol. 1986;21(1):69-73. Abstract only.
Maurin, et al. Cellular adaptation to amino acid availability: mechanisms involved in the regulation of gene expression. 2006; 319-326.
Mayo Clinic Staff. Autism. Retrieved from internet Mar. 10, 2008, http://www.mayoclinic.com/health/autism/DS00348DSECTION=2.
Mayo Clinic Staff. Bipolar disorder. Jan. 4, 2008, http://www.mayoclinic.com/health/bipolardisorder/DS00356/DSECTION=symptoms.
Mayo Clinic Staff. Obsessive-compulsive disorder. Dec. 21, 2006. http://www.preferredalternatives.org/lat/WellnessLibrary/anxiety&PanicDisorders/Obsessive-CompulsiveDisorder/Obsessive-CompulsiveDisorder-Mayoclinic.pdf.
Mayo Clinic Staff. Oppositional defiant disorder. Dec. 19, 2007, http://www.mayoclinic.com/health/oppositional-defiant-disorder/DS00630/DSECTION=symptoms.
McAlonan, et al. Brain anatomy and sensorimotor gating in Asperger's syndrome, ain. Jul. 2002;125(Pt 7):1594-606.
McCormack, et al. Localization of the disulfide bond involved in post-translational processing of glycosylasparaginase and disrupted by a mutation in the Finnish-type aspartylglycosaminuria. J Biol Chem. Feb. 17, 1995;270(7):3212-5.
McCracken, et al. Risperidone in children with autism and serious behavioral problems. N Engl J Med. Aug. 1, 2002;347(5):314-21.
Medsafe. Data sheet for alpha-lactose, Jul. 21, 2008, http://www.medsafe.govt.nz/Profs/Datasheet/a/Alphalactulosesyrup.htm.
Medscape. Burden of Hypertension in the United States Greater Than Ever. www.medscape.com. Jul. 14, 2004.
Merck. Autism, Merck manual online medical library home addition, retrieved from the internet Mar. 10, 2008, http://www.mercl.com/mmhge/sec23/ch286/ch286b.html.
Merriam-Webster 2014 "Definition: Precipitate" accessed from www.mirriam-webster.com on Sep. 22, 2014.

MeSH browser. "Child Development Disorders, Pervasive," and "Attention Deficit and Disruptive Behavior Disorders," National Library of medicine. 2001, http://www.nlm.nih.gov/mesh/2002/Mbrowser.html.
Meyer-Lindenberg, et al. Neural mechanisms in Williams syndrome: a unique window to genetic influences on cognition and behavior. Nat. Rev. Neurosci. 2006; 7(5):380-93.
Michael's Naturopathic Programs, Digestive Enzymes, Product #011161, Accessed on Jun. 10, 2016, online at: www.michaelshealth.com/retail/digestive-enzymes-659.html.
Michell et al. Biomarkers and parkinson's disease. Brain. 2004; 127(8):1693-1705.
Millipore EMD catalog (online). Papain, unit definition, EMD Millipore Corp, 2013. Downloaded May 13, 2013.
Minamino, et al. Vascular cell senescence: contribution to atherosclerosis. Circ Res. Jan. 5, 2007;100(1):15-26.
Ming, et al. Autism spectrum disorders: concurrent clinical disorders. J Child Neurol. Jan. 2008;23(1):6-13.
Mitchell, et al. Comparative trial of viokase, pancreatin and Pancrease pancrelipase (enteric coated beads) in the treatment of malabsorption in cystic fibrosis. Aust Paediatr J. Jun. 1982;18(2):114-7.
Mitsui, et al. Role of aminopepridases in the blood pressure regulation. Biological and Pharmaceutical Bulletin of Japan, Pharmaceutical Sociey of Japan. 2004; 27(6):768-771.
Mononen, et al. Aspartylglycosaminuria in the Finnish population: identification of two point mutations in the heavy chain of glycoasparaginase. Proc Natl Acad Sci U S A. Apr. 1, 1991;88(7):2941-5.
Moretti, et al. Acute pancreatitis: hypertonic saline increases heat shock proteins 70 and 90 and reduces neutrophil infiltration in lung injury. Pancreas. Jul. 2009;38(5):507-14. Abstract only.
Munasinghe et al. Digestive enzyme supplementation for autism spectrum disorders: a double-blind randomized controlled trial. J Autism Dev Disord. Sep. 2010;40(9):1131-8.
Munasinghe et al. Digestive enzyme supplementation for autism spectrum disorders: a double-blind randomized controlled trial. J Autism Dev Disord. Sep. 2010;40(9):1131-8. Abstract only.
Nachaegari et al. Coprocessed excipients for solid dosage forms. Pharmaceutical Technology. 2004; p. 52, 54, 56 ,58, 60, 64.
Nagamoto. Jacobson: Psychiatric Secrets, 2nd ed. 2001. Ch 28 Antipsychotic meds.
Neuer, et al. The role of heat shock proteins in reproduction. Hum Reprod Update. Mar.-Apr. 2000;6(2):149-59.
Nevo et al. Acute immune polyneuropathies: correlations of serum antibodies to Campylobacter jejuni and helicobacter pylori with anti-gm antibodies and clinical patterns of disease. J of Inf diseases. 1997; 175(S2):S154-6.
Newhorizons. ADD/ADHD: New Perspectives on Attentional Priority Disorders. New Horizons for Learning. Jul. 15, 2008.
NIH, "Celiac Disease", National Digestive Diseases Information Clearinghouse: Bethesda, MD, 2008;12 pages.
NIH. National Institutes of Health. National Diabetes Statistics 2007. diabetes.niddk.nih.gov. Jun. 1, 2008.
NINDS Dysautonimia Information Page, retrieved from the internet Sep. 10, 2009, http://www.ninds.nih.gov/disorders/dysautonomia/dysautonomia.htm.
NINDS Guillain-Barre Syndrome Information Page, retrieved from the internet Sep. 15, 2009, http://www.ninds.nih.gov/disorders/gbs/gbs.htm.
Notice Non-Compliant Amendment dated Jun. 19, 2009 for U.S. Appl. No. 11/232,180.
Notice Non-responsive Amendment dated Sep. 22, 2008 for U.S. Appl. No. 11/232,180.
Notice of allowance dated Jan. 2, 2014 for U.S. Appl. No. 13/204,881.
Notice of allowance dated Feb. 2, 2015 for U.S. Appl. No. 13/926,822.
Notice of Allowance dated Feb. 17, 2012 for U.S. Appl. No. 10/681,018.
Notice of allowance dated Feb. 20, 2015 for U.S. Appl. No. 12/386,051.
Notice of allowance dated Feb. 27, 2015 for U.S. Appl. No. 14/037,696.
Notice of allowance dated Mar. 1, 2016 for U.S. Appl. No. 14/087,930.

(56) References Cited

OTHER PUBLICATIONS

Notice of Allowance dated Mar. 21, 2012 for U.S. Appl. No. 12/487,864.
Notice of allowance dated Apr. 3, 2015 for U.S. Appl. No. 13/737,225.
Notice of allowance dated Apr. 10, 2015 for U.S. Appl. No. 13/144,290.
Notice of allowance dated Apr. 14, 2015 for U.S. Appl. No. 13/144,286.
Notice of Allowance dated Apr. 15, 2011 for U.S. Appl. No. 12/487,868.
Notice of allowance dated Apr. 22, 2016 for U.S. Appl. No. 14/528,715.
Notice of Allowance dated Apr. 29, 2011 for U.S. Appl. No. 12/046,402.
Notice of Allowance dated May 23, 2011 for U.S. Appl. No. 09/990,909.
Notice of Allowance dated May 29, 2013 for U.S. Appl. No. 13/481,087.
Notice of allowance dated Jun. 12, 2014 for U.S. Appl. No. 13/448,061.
Notice of Allowance dated Jun. 27, 2011 for U.S. Appl. No. 12/238,415.
Notice of Allowance dated Jun. 28, 2011 for U.S. Appl. No. 12/487,868.
Notice of Allowance dated Jun. 30, 2011 for U.S. Appl. No. 09/990,909.
Notice of allowance dated Jul. 3, 2012 for U.S. Appl. No. 13/271,783.
Notice of Allowance dated Jul. 8, 2011 for U.S. Appl. No. 12/046,402.
Notice of Allowance dated Aug. 8, 2011 for U.S. Appl. No. 12/426,794.
Notice of allowance dated Aug. 11, 2014 for U.S. Appl. No. 13/193,346.
Notice of allowance dated Aug. 19, 2013 for U.S. Appl. No. 13/208,963.
Notice of allowance dated Aug. 30, 2013 for U.S. Appl. No. 12/047,818.
Notice of allowance dated Sep. 9, 2015 for U.S. Appl. No. 13/193,346.
Notice of allowance dated Sep. 15, 2014 for U.S. Appl. No. 14/037,652.
Notice of Allowance dated Sep. 20, 2011 for U.S. Appl. No. 12/283,090.
Notice of allowance dated Oct. 29, 2013 for U.S. Appl. No. 13/204,881.
Notice of allowance dated Nov. 16, 2015 for U.S. Appl. No. 14/493,734.
Notice of allowance dated Dec. 23, 2014 for U.S. Appl. No. 14/007,793.
Notice of allowance dated Dec. 23, 2015 for U.S. Appl. No. 12/493,122.
Notice of Non-Complaint Amendment dated Jun. 2, 2008 for U.S. Appl. No. 12/046,252.
Notice of Non-Compliant Amendment dated Apr. 27, 2010 for U.S. Appl. No. 12/283,090.
Notice of Non-Compliant Amendment dated May 7, 2007 for U.S. Appl. No. 11/213,255.
Notice of Non-Responsive Amendment dated Feb. 11, 2008 for U.S. Appl. No. 11/555,697.
Notice of Non-Responsive Amendment dated Sep. 25, 2008 for U.S. Appl. No. 11/555,697.
O'Connell. Hypertension Guide, cmbi.bjmu.edu. Jul. 14, 2008.
Office action dated Jan. 12, 2012 for U.S. Appl. No. 12/047,818.
Office action dated Jan. 15, 2014 for U.S. Appl. No. 13/836,135.
Office action dated Jan. 15, 2016 for U.S. Appl. No. 13/502,989.
Office action dated Jan. 16, 2014 for U.S. Appl. No. 12/046,252.
Office action dated Jan. 16, 2015 for U.S. Appl. No. 12/535,676.
Office action dated Jan. 22, 2013 for U.S. Appl. No. 13/562,999.
Office action dated Jan. 24, 2014 for U.S. Appl. No. 12/054,343.
Office action dated Jan. 24, 2014 for U.S. Appl. No. 12/786,739.
Office action dated Jan. 25, 2013 for U.S. Appl. No. 13/208,963.
Office action dated Jan. 26, 2016 for U.S. Appl. No. 12/054,343.
Office action dated Jan. 29, 2016 for U.S. Appl. No. 12/786,739.
Office Action dated Feb. 1, 2012 for U.S. Appl. No. 12/493,122.
Office action dated Feb. 1, 2016 for U.S. Appl. No. 13/503,844.
Office action dated Feb. 14, 2013 for U.S. Appl. No. 13/193,346.
Office action dated Feb. 14, 2013 for U.S. Appl. No. 13/407,408.
Office action dated Feb. 17, 2016 for U.S. Appl. No. 14/713,178.
Office action dated Feb. 21, 2013 for U.S. Appl. No. 12/047,818.
Office action dated Feb. 26, 2016 for U.S. Appl. No. 12/535,676.
Office action dated Mar. 2, 2016 for U.S. Appl. No. 14/693,711.
Office Action dated Mar. 5, 2012 for U.S. Appl. No. 12/535,676.
Office action dated Mar. 5, 2013 for U.S. Appl. No. 12/493,122.
Office action dated Mar. 6, 2015 for U.S. Appl. No. 13/757,412.
Office action dated Mar. 11, 2014 for U.S. Appl. No. 11/533,818.
Office Action dated Mar. 19, 2012 for U.S. Appl. No. 13/204,881.
Office action dated Mar. 22, 2016 for U.S. Appl. No. 13/733,873.
Office Action dated Mar. 23, 2012 for U.S. Appl. No. 13/271,783.
Office Action dated Mar. 29, 2011 for U.S. Appl. No. 12/054,343.
Office Action dated Mar. 30, 2011 for U.S. Appl. No. 12/786,739.
Office action dated Mar. 30, 2016 for U.S. Appl. No. 14/296,091.
Office action dated Apr. 4, 2016 for U.S. Appl. No. 13/313,629.
Office Action dated Apr. 5, 2012 for U.S. Appl. No. 11/555,697.
Office action dated Apr. 5, 2016 for U.S. Appl. No. 14/713,242.
Office action dated Apr. 6, 2015 for U.S. Appl. No. 14/493,734.
Office action dated Apr. 6, 2016 for U.S. Appl. No. 13/313,708.
Office Action dated Apr. 9, 2012 for U.S. Appl. No. 13/208,963.
Office action dated Apr. 10, 2014 for U.S. Appl. No. 13/502,989.
Office action dated Apr. 13, 2016 for U.S. Appl. No. 14/612,604.
Office action dated Apr. 16, 2014 for U.S. Appl. No. 13/705,763.
Office action dated Apr. 21, 2015 for U.S. Appl. No. 13/660,642.
Office action dated Apr. 21, 2015 for U.S. Appl. No. 14/087,930.
Office action dated Apr. 22, 2015 for U.S. Appl. No. 13/836,135.
Office action dated Apr. 24, 2015 for U.S. Appl. No. 12/786,739.
Office Action dated Apr. 27, 2011 for U.S. Appl. No. 10/681,018.
Office action dated Apr. 27, 2015 for U.S. Appl. No. 12/054,343.
Office Action dated Apr. 28, 2011 for U.S. Appl. No. 12/283,090.
Office action dated May 6, 2015 for U.S. Appl. No. 12/493,122.
Office action dated May 7, 2015 for U.S. Appl. No. 13/705,763.
Office action dated May 9, 2013 for U.S. Appl. No. 13/204,881.
Office action dated May 12, 2014 for U.S. Appl. No. 13/733,873.
Office action dated May 13, 2014 for U.S. Appl. No. 13/313,629.
Office action dated May 15, 2013 for U.S. Appl. No. 13/502,989.
Office action dated May 15, 2014 for U.S. Appl. No. 13/448,061.
Office action dated May 16, 2014 for U.S. Appl. No. 13/313,708.
Office Action dated May 24, 2011 for U.S. Appl. No. 12/487,864.
Office action dated May 27, 2015 for U.S. Appl. No. 13/502,989.
Office action dated Jun. 3, 2015 for U.S. Appl. No. 13/002,136.
Office action dated Jun. 13, 2012 for U.S. Appl. No. 12/493,122.
Office action dated Jun. 17, 2014 for U.S. Appl. No. 13/737,225.
Office action dated Jun. 17, 2014 for U.S. Appl. No. 13/757,412.
Office action dated Jun. 19, 2014 for U.S. Appl. No. 12/386,051.
Office action dated Jun. 25, 2013 for U.S. Appl. No. 13/144,286.
Office action dated Jun. 25, 2013 for U.S. Appl. No. 13/144,290.
Office action dated Jun. 27, 2012 for U.S. Appl. No. 12/493,147.
Office action dated Jun. 27, 2014 for U.S. Appl. No. 14/007,793.
Office action dated Jun. 29, 2011 for U.S. Appl. No. 11/555,697.
Office action dated Jul. 7, 2014 for U.S. Appl. No. 12/535,676.
Office action dated Jul. 11, 2012 for U.S. Appl. No. 12/573,353.
Office action dated Jul. 15, 2013 for U.S. Appl. No. 13/002,136.
Office action dated Jul. 17, 2015 for U.S. Appl. No. 13/733,873.
Office action dated Jul. 18, 2012 for U.S. Appl. No. 12/047,818.
Office action dated Jul. 31, 2013 for U.S. Appl. No. 13/757,412.
Office action dated Aug. 2, 2013 for U.S. Appl. No. 12/535,676.
Office action dated Aug. 7, 2014 for U.S. Appl. No. 13/836,135.
Office action dated Aug. 13, 2012 for U.S. Appl. No. 13/208,963.
Office action dated Aug. 14, 2013 for U.S. Appl. No. 13/448,061.
Office action dated Aug. 28, 2013 for U.S. Appl. No. 13/313,629.
Office action dated Aug. 29, 2014 for U.S. Appl. No. 13/144,286.
Office action dated Aug. 31, 2015 for U.S. Appl. No. 12/535,676.
Office action dated Sep. 8, 2015 for U.S. Appl. No. 11/533,818.
Office action dated Sep. 9, 2013 for U.S. Appl. No. 13/502,989.
Office action dated Sep. 10, 2015 for U.S. Appl. No. 13/313,629.
Office action dated Sep. 11, 2015 for U.S. Appl. No. 13/313,708.
Office action dated Sep. 13, 2012 for U.S. Appl. No. 13/481,087.

(56) References Cited

OTHER PUBLICATIONS

Office action dated Sep. 18, 2014 for U.S. Appl. No. 13/502,989.
Office action dated Sep. 19, 2014 for U.S. Appl. No. 11/533,818.
Office action dated Sep. 19, 2014 for U.S. Appl. No. 13/737,225.
Office action dated Sep. 30, 2014 for U.S. Appl. No. 13/144,290.
Office action dated Sep. 30, 2014 for U.S. Appl. No. 13/660,642.
Office action dated Oct. 2, 2014 for U.S. Appl. No. 12/054,343.
Office action dated Oct. 6, 2014 for U.S. Appl. No. 12/493,122.
Office action dated Oct. 9, 2014 for U.S. Appl. No. 12/786,739.
Office Action dated Oct. 1, 2001 for U.S. Appl. No. 09/466,559.
Office action dated Oct. 10, 2012 for U.S. Appl. No. 13/204,881.
Office action dated Oct. 19, 2011 for U.S. Appl. No. 12/386,051.
Office action dated Oct. 24, 2013 for U.S. Appl. No. 13/313,708.
Office action dated Oct. 25, 2012 for U.S. Appl. No. 13/144,286.
Office action dated Oct. 25, 2012 for U.S. Appl. No. 13/144,290.
Office action dated Oct. 30, 2015 for U.S. Appl. No. 14/528,715.
Office Action dated Oct. 5, 2010 for U.S. Appl. No. 12/046,402.
Office action dated Nov. 7, 2014 for U.S. Appl. No. 13/705,763.
Office Action dated Nov. 14, 2007 for U.S. Appl. No. 11/213,255.
Office action dated Nov. 15, 2010 for U.S. Appl. No. 12/238,415.
Office action dated Nov. 16, 2015 for U.S. Appl. No. 13/705,763.
Office action dated Nov. 19, 2015 for U.S. Appl. No. 14/713,242.
Office action dated Nov. 20, 2015 for U.S. Appl. No. 14/296,091.
Office action dated Nov. 20, 2015 for U.S. Appl. No. 14/612,604.
Office action dated Nov. 21, 2014 for U.S. Appl. No. 13/926,822.
Office Action dated Nov. 25, 2009 for U.S. Appl. No. 11/232,180.
Office Action dated Nov. 26, 2001 for U.S. Appl. No. 09/466,559.
Office action dated Nov. 29, 2013 for U.S. Appl. No. 13/193,346.
Office action dated Dec. 6, 2012 for U.S. Appl. No. 13/002,136.
Office action dated Dec. 10, 2013 for U.S. Appl. No. 13/407,408.
Office action dated Dec. 10, 2015 for U.S. Appl. No. 13/836,135.
Office Action dated Jan. 21, 2011 for U.S. Appl. No. 12/386,051.
Office action dated Dec. 12, 2013 for U.S. Appl. No. 13/144,286.
Office action dated Dec. 13, 2013 for U.S. Appl. No. 12/493,122.
Office action dated Dec. 13, 2013 for U.S. Appl. No. 13/144,290.
Office action dated Dec. 15, 2011 for U.S. Appl. No. 12/493,147.
Office action dated Dec. 15, 2015 for U.S. Appl. No. 14/087,930.
Office action dated Dec. 16, 2013 for U.S. Appl. No. 12/535,676.
Office action dated Dec. 18, 2014 for U.S. Appl. No. 14/037,696.
Office action dated Dec. 18, 2015 for U.S. Appl. No. 14/640,385.
Office Action dated Dec. 19, 2005 for U.S. Appl. No. 10/730,567.
Office action dated Dec. 19, 2014 for U.S. Appl. No. 13/733,873.
Office Action dated Dec. 22, 2006 for U.S. Appl. No. 10/681,018.
Office action dated Dec. 24, 2015 for U.S. Appl. No. 13/757,412.
Office Action dated Jan. 29, 2002 for U.S. Appl. No. 09/707,395.
Office Action dated Jan. 8, 2010 for U.S. Appl. No. 10/681,018.
Office Action dated Mar. 18, 2008 for U.S. Appl. No. 11/468,379.
Office Action dated Mar. 25, 2008 for U.S. Appl. No. 11/213,382.
Office Action dated Mar. 28, 2008 for U.S. Appl. No. 11/555,697.
Office Action dated Apr. 12, 2010 for U.S. Appl. No. 09/990,909.
Office Action dated Apr. 21, 2008 for U.S. Appl. No. 11/232,180.
Office Action dated Apr. 22, 2003 for U.S. Appl. No. 09/929,592.
Office Action dated May 22, 2002 for U.S. Appl. No. 09/466,559.
Office Action dated Jun. 30, 2004 for U.S. Appl. No. 10/730,567.
Office Action dated Jul. 22, 2010 for U.S. Appl. No. 12/049,613.
Office Action dated Jul. 29, 2003 for U.S. Appl. No. 09/990,909.
Office Action dated Jul. 30, 2002 for U.S. Appl. No. 09/707,395.
Office Action dated Jul. 30, 2002 for U.S. Appl. No. 09/990,909.
Office Action dated Jul. 6, 2010 for U.S. Appl. No. 11/533,818.
Office Action dated Aug. 13, 2002 for U.S. Appl. No. 09/929,592.
Office Action dated Aug. 18, 2008 for U.S. Appl. No. 10/681,018.
Office Action dated Aug. 18, 2010 for U.S. Appl. No. 10/681,018.
Office Action dated Aug. 20, 2010 for U.S. Appl. No. 12/283,090.
Office Action dated Aug. 25, 2010 for U.S. Appl. No. 12/487,868.
Office Action dated Aug. 26, 2003 for U.S. Appl. No. 10/041,073.
Office Action dated Aug. 3, 2009 for U.S. Appl. No. 11/555,697.
Office Action dated Aug. 7, 2007 for U.S. Appl. No. 10/681,018.
Office Action dated Aug. 8, 2007 for U.S. Appl. No. 11/213,382.
Office Action dated Sep. 22, 2004 for U.S. Appl. No. 10/730,567.
Office Action dated Sep. 24, 2009 for U.S. Appl. No. 12/046,252.

Office Action dated May 11, 2016 U.S. Appl. No. 14/713,242.
Okahata, et al. Lipid-coated enzymes as efficient catalysts in organic media. Trends in Biotechnology. 1997; 15(2):50-54.
Olivar-Parra, et al. Training referential communicative skills to individuals with autism spectrum disorder: a pilot study. Psychological Reports. 2011; 109:921-939.
Owley, et al. Multisite, double-blind, placebo-controlled trial of porcine secretin in autism. J Am Acad Child Adolesc Psychiatry. Nov. 2001;40(11):1293-9.
Pancrease. Patient information leaflet. Pancrease HL Capsules. Last updated Apr. 30, 2013. Janssen-cilag LTD. www.medicines.org.uk/EMC/medicine/7326.
Pancreatic Enzyme Concentrate (PEC) Undiluted, Technical Data Sheet. 1 page, Scientific Protein Laboratories LLC Jun. 13, 2005.
Pancreatin 4X USP, Technical Data Sheet, 1 page, Scientific Protein laboratories LLC Jun. 13, 2005.
Pancreatin 8X USP Powder. Product Specification. Jul. 2000. In: Product Manual. American Laboratories Incorporated. Omaha, NE. p. 1.
Parisi et al. Evaluation of new rapid commercial enzyme immunoassay for detection of crytosporidium oocysts in untreated stool specimens. J Clin Microbiol. 1995; 33(7):1963-1965.
Park, et al. Increased apoptosis in cystinotic fibroblasts and renal proximal tubule epithelial cells results from cysteinylation of protein kinase Cdelta. J Am Soc Nephrol. Nov. 2006;17(11):3167-75.
Parkinsons Disease Foundation. Parkinson's Disease Q&A. 2007. 1-44.
Parkinsons Disease Foundation. Ten Frequently-Asked Questions about Parkinson's Disease. 2006.
Parracho, et al. Differences between the gut microflora of children with autistic spectrum disorders and that of healthy children. J Med Microbiol. Oct. 2005;54(Pt 10):987-91.
Patel, et al. Formulation and evaluation of mucoadhesive glipizide microspheres. AAPS PharmSciTech. 2005; 6(1):E49-E55.
PDTALKS. Motivational & Inspirational Speaking From a Parkinson's Patient Perspective. pdtalks.com/Parkinson_s_Disease.html. Jul. 14, 2008.
Perman et al. Role of ph in production of hydrogen from carbohydrates by colonic bacterial flora. J Clin Invest. 1981; 24(4):684-685.
Persico, et al. Searching for ways out of the autism maze: genetic, epigenetic and environmental clues. Trends Neurosci. Jul. 2006;29(7):349-58.
Peters et al. Prevalence of enteric parasites in homosexual patients attending an outpatient clinic. J of Clin Micro. 1986; 24(4):684-685.
Peters, et al. Treatment of alcoholic polyneuropathy with vitamin B complex: a randomised controlled trial. Alcohol Alcohol. Nov.-Dec. 2006;41(6):636-42. Epub Aug. 21, 2006.
Petrolatum: Pharmaceutical Excipients. London: Pharmaceutical Press. 2006. 1-6.
Pisani, et al. Levodopa-induced dyskinesia and striatal signaling pathways. Proc Natl Acad Sci U S A. Mar. 3, 2009;106(9):2973-4. Epub Feb. 26, 2009.
Polanczyk, et al. The worldwide prevalence of ADHD: a systematic review and metaregression analysis. Am J Psychiatry. Jun. 2007;164(6):942-8.
Ponsky, et al. Alterations in gastrointestinal physiology after Roux-en-Y gastric bypass. J Am Coll Surg. Jul. 2005;201(1):125-31.
Preliminary Amendment dated May 18, 2009 for U.S. Appl. No. 12/046,252.
Proesmans, Marijke et al. Omeprazole, a proton pump inhibitor, improves residual steatorrhoea in cystic fibrosis patients treated with high dose pancreatic enzymes. European Journal of Pediatrics 162(11): 760-763 (Nov. 2003).
Puri, et al. Isolated segmental duodenal ganglionosis. Indian Journal of Radiology and Imaging. 2000; 153-154.
Raimondo, et al. Rapid endoscopic secretin simulation test and discrimination of chronic pancreatisis and pancreatic cancer from disease controls. Clin Gastroenterol Hepatol. Sep. 2003;1(5):397-403.
Rajakumar, et al. Proteasomal activity in placentas from women with preeclampsia and intrauterine growth restriction: implications forexpression of HIF-alpha proteins. Placenta. Mar. 2008;29(3):290-9. Epub Jan. 28, 2008.

(56) References Cited

OTHER PUBLICATIONS

Rakonczay, et al. A new severe acute necrotizing pancreatitis model induced by L-ornithine in rats. Crit Care Med. Jul. 2008;36(7):2117-27.
Ray, et al. Growth factor regulation of enterocyte nutrient transport during intestinal adaptation. Am J Surg. Apr. 2002;183(4):361-71.
Reeves, G. et al. Pharmacological Management of Attention-deficit hyperactivity disorder, Expert Opinion on Pharmacotherapy, 5:6; 1313-1320. (Feb. 25, 2005)DOI: 10.1517/14656566.5.6.1313 http://dx.doi.org/10.1517/14656566.5.6.1313.
Regan, et al. Comparative effects of antacids, cimetidine and enteric coating on the therapeutic response to oral enzymes in severe pancreatic insufficiency. N Engl J Med. Oct. 20, 1977;297(16):854-8.
Remtulla et al. Stool chymotrypsin activity measured by a spectrophotometric procedure to identify pancreat disease in infants. Clinical Biochemistry. Dec. 1986; 19:341-342.
Response dated Oct. 3, 2006 to Restriction Requirement dated Sep. 12, 2006 for U.S. Appl. No. 10/681,018.
Response dated Apr. 29, 2010 to Notice of Non-Compliant Amendment dated Apr. 27, 2010 for U.S. Appl. No. 12/283,090.
Response dated Jun. 17, 2008 to Advisory Action dated Jun. 3, 2008 for U.S. Appl. No. 10/681,018.
Response dated Jun. 24, 2002 to Restriction Requirement dated May 22, 2002 for U.S. Appl. No. 09/990,909.
Response dated Jun. 7, 2007 to Notice of Non-Compliant Amendment dated May 7, 2007 for U.S. Appl. No. 11/213,255.
Restriction Requirement dated Oct. 17, 2007 for U.S. Appl. No. 11/555,697.
Restriction Requirement dated Oct. 7, 2009 for U.S. Appl. No. 12/283,090.
Restriction Requirement dated Jan. 10, 2008 for U.S. Appl. No. 11/232,180.
Restriction Requirement dated Jan. 13, 2010 for U.S. Appl. No. 12/487,868.
Restriction Requirement dated Dec. 10, 2009 for U.S. Appl. No. 11/533,818.
Restriction Requirement dated Apr. 23, 2003 for U.S. Appl. No. 09/990,909.
Restriction Requirement dated May 22, 2002 for U.S. Appl. No. 09/990,909.
Restriction Requirement dated May 9, 2007 for U.S. Appl. No. 11/213,382.
Restriction Requirement dated Jun. 22, 2007 for U.S. Appl. No. 11/213,255.
Restriction Requirement dated Sep. 12, 2006 for U.S. Appl. No. 10/681,018.
Revolution health. Enzyme therapy, revolutionhealth.com/drugs-treatments/enzyme-therapy. Sep. 2, 2008.
Richards, et al. Diagnosis, management, and treatment of Alzheimer disease: a guide for the internist. Arch Intern Med. Apr. 26, 1999;159(8):789-98.
Rider, et al. Perspective of biochemical research in the neuronal ceroid-lipofuscinosis. Am J Med Genet. Feb. 15, 1992;42(4):519-24.
Riedel, L et al. Limitations of faecal chymotrypsin as a screening test for chronic pancreatitis. Gut, 32:321-324 (1991).
Rogers. No more heartburn: Stop the pain in 30 days—naturally. 2000; 172.
Rottier, et al. Lack of PPCA expression only partially coincides with lysosomal storage in galactosialidosis mice: indirect evidence for spatial requirement of the catalytic rather than the protective function of PPCA. Hum Mol Genet. Oct. 1998;7(11):1787-94.
Roxas, et al. Colds and influenza: a review of diagnosis and conventional, botanical, and nutritional considerations. Alternative Medicine Review. 2007; 12(1):25-48.
Rubenstein, et al. Model of autism: increased ratio of excitation/inhibition in key neural systems. Genes Brain Behav. Oct. 2003;2(5):255-67.
Sahelian. Enzymes, raysahelian.com/enzymes.html. Sep. 2, 2008.
Sandler, et al. Lack of benefit of a single dose of synthetic human secretin in the treatment of autism and pervasive developmental disorder. N Engl J Med. Dec. 9, 1999;341(24):1801-6.
Sandler et al. Short term benefit from oral vancomycin treatment of regressive-onset autism. J of Child Neuro. 2000; 15(7):42-435.
Schafer, et al. Stress kinases and heat shock proteins in the pancreas: possible roles in normal function and disease. J Gastroenterol. 2000;35(1):1-9.
Schiller. Review article: the therapy of constipation. Aliment Pharmacol Ther. 2001; 15:749-763.
Schizophreniform disorder. Merck Manuals Online Medical Library. Nov. 2005. (in Japanese with English translation).
Schneider, et al. Oral human immunoglobulin for children with autism and gastrointestinal dysfunction: a prospective, open-label study. J Autism Dev Disord. Nov. 2006;36(8):1053-64.
Schreck et al. Food preferences and factors influecing food selectivity for children with autism spectrum disorders. Res Develop Disabil. 2006; 27:353-363.
Schumann. Medical, nutritional and technological properties of lactulose. An update. Eur J Nutr. Nov. 2002;41 Suppl 1:I17-25.
Seltzer, et al. The Symptoms of Autism Spectrum Disorders in Adolescence and Adulthood. Journal of Autism and Developmental Disorders. 2003; 33(6):565-581.
Seneca et al. Enhancement of brain I-dopa concetration with a-chymotrypsm. J American Geriatrics Society. 1973; 256-258. Abstract only.
Serna, et al. Pathogenesis and treatment of Shiga toxin-producing *Escherichia coli* infections. Curr Opin Gastroenterol. Jan. 2008;24(1):38-47.
Settembre, et al. A block of autophagy in lysosomal storage disorders. Hum Mol Genet. Jan. 1, 2008;17(1):119-29.
Shadel. Expression and maintenance of mitochondrial DNA: new insights into human disease pathology. Am J Pathol. Jun. 2008;172(6):1445-56.
Shaul. Report to the Chairman and Ranking Minority Member, Subcommittee on Human Rights and Wellness, Committee on Government Reform, House of Representatives. GEO. Jan. 2005. 1-40.
Shelby, et al. Enzymatic debridement with activated whole pancreas. American Journal of Surgery. Oct. 1958; 96(4):545-549.
Sherwood et al. A new class of high-functionality excipients: silicified microcrystalline cellulose. Pharm Tech. 1998; 22(10):78-88.
Sherwood, et al. Activation of trypsinogen in large endocytic vacuoles of pancreatic acinar cells. Proc Natl Acad Sci U S A. Mar. 27, 2007;104(13):5674-9.
Shimabukuro, et al. Medical expenditures for children with an autism spectrum disorder in a privately insured population. J Autism Dev Disord. 2007;38(3):546-52.
Shpacovitch, et al. Protease-activated receptors: novel PARtners in innate immunity. Trends Immunol. Dec. 2007;28(12):541-50.
Shpacovitch, et al. Role of protease-activated receptors in inflammatory responses, innate and adaptive immunity. J Leukoc Biol. Jun. 2008;83(6):1309-22.
Sienaert, et al. Evidence-based treatment strategies for treatment-resistant bipolar depression: a systematic review. Bipolar Disord. Feb. 2013;15(1):61-9. doi: 10.1111/bdi.12026. Epub Nov. 27, 2012.
Sillanaukee, et al. Improved diagnostic classification of alcohol abusers by combining carbohydrate-deficient transferrin and gamma-glutamyltransferase. Clin Chem. Apr. 2001;47(4):681-5.
Simonoff, et al. Psychiatric disorders in children with autism spectrum disorders: prevalence, comorbidity, and associated factors in a population-derived sample. J Am Acad Child Adolesc Psychiatry. Aug. 2008;47(8):921-9.
Singh, et al. Plasma increase of interleukin-12 and interferon-gamma. Pathological significance in autism. J Neuroimmunol. May 1996;66(1-2):143-5.
Skeels et al. Crytosporidium infection in Oregon public health clinic patients 1985-1988: the value of statewide laboratory surveillance. AJPH. 1990; 80(3):305-308.
Skinner, et al. Treatment of Prion Disease with Heterologous Prion Proteins. PLoS One. Jul. 2, 2015;10(7):e0131993. doi: 10.1371/journal.pone.0131993. eCollection 2015.

(56) References Cited

OTHER PUBLICATIONS

Smith, et al. Fecal chymotrypsin and trypsin determinations. Canadian Medical Association Journal. 1971; 104(8):691-4 and 697.
Statemaster. Number of Children with Autism (most recent) by state. Statemaster.com Jul. 14, 2008.
Statemaster. Number of Children with Autism (most recent w/graph) by state. Statemaster.com Jul. 14, 2003.
Statemaster. Number of Children with Autism (per capita)(most recent) by state. Statemaster.com Jul. 14, 2003.
Stein, et al. Nitrogen metabolism in normal and hyperkinetic boys. Am J Clin Nutr. Apr. 1984;39(4):520-4.
Steinherz, et al. Patterns of amino acid efflux from isolated normal and cystinotic human leucocyte lysosomes. J Biol Chem. Jun. 10, 1982;257(11):6041-9.
Sternby, et al. Carboxyl Ester Lipase (Bile Salt-Stimulated Lipase), Colipase, Lipase, and Phospholipase A2 Levels in Pancreatic Enzyme Supplements, 1997, Scandinavian Journal of Gastroenterology 32(3): 261-267.
Stoll, et al. Enteral nutrient intake level determines intestinal protein synthesis and accretion rates in neonatal pigs. Am J Physiol Gastrointest Liver Physiol. Aug. 2000;279(2):G288-94.
Stott, et al. MMR and Autism in Perspective: the Denmark Story. J. Am Phys Surg. 2004; 9(3):89-91.
Strader, et al. Structural basis of β-adrenergic receptor function. FASEB J. May 1989;3(7):1825-32.
Sturmey. Secretin is an ineffective treatment for pervasive developmental disabilities: a review of 15 double-blind randomized controlled trials. Res Dev Disabil. Jan.-Feb. 2005;26(1):87-97.
Sundstrom, et al. A deadly prion disease: fatal familial insomnia. J Neurosci Nurs. Dec. 2003;35(6):300-5. Abstract only.
Supplemental Amendment and Response dated Jun. 8, 2010 to Restriction Requirement dated Oct. 7, 2009 for U.S. Appl. No. 12/283,090.
Swayne, et al. Pathobiology of H5N2 Mexican avian influenza virus infections of chickens. Vet Pathol. Nov. 1997;34(6):557-67.
Tager-Flusberg, et al. Language disorders: autism and other pervasive developmental disorders. Pediatr Clin North Am. Jun. 2007;54(3):469-81, vi.
Tamaro. Vitamin K deficiency as a cause of autistic symptoms. Http://web.archive.org/web/20090612022246/http://www.gutresearch.com/VitaminK.pdf. Published Jun. 12, 2009 as per Wayback Engine.
Terrie, et al. Understanding Pancreatic Enzyme Products. Dec. 15, 2008.
The Alzheimer's Association. Basics of Alzheimer's Disease. 2005, 32 pages. http://www.alz.org/national/documents/brochure_Basicsofalz_low/pdf.
THEFREEDICTIONARY. Term Sprinkles. Www.thefreedictionary.com. Accessed Nov. 2, 2011. 1 page.
Thomas, et al. Defective protein folding as a basis of human disease. Trends Biochem Sci. Nov. 1995;20(11):456-9.
Tiedermann, et al. Identification of a potent natural triterpenoid inhibitor of proteosome chymotrypsin-like activity and NF-kappaB with antimyeloma activity in vitro and in vivo. Blood. Apr. 23, 2009;113(17):4027-37.
Torrente, et al. Focal-enhanced gastritis in regressive autism with features distinct from Crohn's and Helicobacter pylori gastritis. Am J Gastroenterol. Apr. 2004;99(4):598-605.
Torrente, et al. Small intestinal enteropathy with epithelial IgG and complement deposition in children with regressive autism. Mol Psychiatry. 2002;7(4):375-82, 334.
Tran, et al. Treatment of complex regional pain syndrome: a review of the evidence. Can J Anaesth. Feb. 2010;57(2):149-66.
Trauner, et al. Specific cognitive deficits in young children with cystinosis: evidence for an early effect of the cystinosin gene on neural function. J Pediatr. Aug. 2007;151(2):192-6.
Troy. Pancreatic Enzymes. Remington: The Science and Practice of Pharmacy, 21st edition. Lippincot Williams & Wilkins, 2006. p. 1304.
Tsan, et al. Heat shock proteins and immune system. J Leukoc Biol. Jun. 2009;85(6):905-10.
Tsang et al. Extragastroduodenal conditions associated with Heliobacter pylori infection. Hong Kong Medical Journal. 1999; 5(2):169-174.
Uhlmann, et al. Potential viral pathogenic mechanism for new variant inflammatory bowel disease. Mol Pathol. Apr. 2002;55(2):84-90.
UK search and examination report dated Mar. 26, 2013 for GB 1111565.6.
UK search and examination report dated Mar. 27, 2013 for GB 1111566.4.
UK search and examination report dated Apr. 18, 2013 for GB 1117669.0.
ULTRESA—FDA Prescribing Information Side Effects and Uses. Revised Sep. 2014.
ULTRESA. Highlights of prescribing information. Aptalis Pharma US Inc. Revised Mar. 2012.
Unis, et al. A randomized, double-blind, placebo-controlled trial of porcine versus synthetic secretin for reducing symptoms of autism. J Am Acad Child Adolesc Psychiatry. Nov. 2002;41(11):1315-21.
UPI. Number of autistic Calif, students triples. United Press International. Jul. 12, 2008.
"U.S. Appl. No. 11/533,818 Final Office Action dated Jun. 7, 2016".
"U.S. Appl. No. 12/054,343 Final Office Action dated May 10, 2017".
"U.S. Appl. No. 12/054,343 Office Action dated Aug. 19, 2016".
"U.S. Appl. No. 12/535,676 Non-Final Office Action dated Apr. 21, 2017".
U.S. Appl. No. 12/535,676 Office Action dated Sep. 13, 2016.
U.S. Appl. No. 12/786,739 Final Office Action dated Jun. 23, 2017.
U.S. Appl. No. 12/786,739 Office Action dated Sep. 20, 2016.
U.S. Appl. No. 13/002,136 Final Office Action dated Jun. 24, 2016.
U.S. Appl. No. 13/002,136 Non-Final Office Action dated Feb. 27, 2017.
U.S. Appl. No. 13/193,346 Notice of Allowability dated Jul. 14, 2016.
U.S. Appl. No. 13/193,346 Notice of Allowability dated Jun. 2, 2016.
U.S. Appl. No. 13/313,629 Notice of Allowance dated Dec. 22, 2016.
U.S. Appl. No. 13/313,708 Notice of Allowance dated Dec. 15, 2016.
U.S. Appl. No. 13/502,989 Notice of Allowance dated Aug. 10, 2016.
U.S. Appl. No. 13/503,844 Office Action dated Aug. 25, 2016.
U.S. Appl. No. 13/503,844 Office Action dated Mar. 27, 2017.
"U.S. Appl. No. 13/705,763 Final Office Action dated May 24, 2016".
U.S. Appl. No. 13/733,873 Non-Final Office Action dated May 25, 2017.
U.S. Appl. No. 13/757,412 Final Office Action dated Jun. 30, 2016.
U.S. Appl. No. 13/757,412 Office Action dated Feb. 10, 2017.
U.S. Appl. No. 13/836,135 Final Office Action dated May 15, 2017.
U.S. Appl. No. 13/836,135 Office Action dated Jul. 22, 2016.
U.S. Appl. No. 14/296,091 Final Office Action dated Aug. 23, 2017.
U.S. Appl. No. 14/296,091 Final Office Action dated Jan. 3, 2017.
U.S. Appl. No. 14/612,580 Final Office Action dated Aug. 10, 2017.
U.S. Appl. No. 14/612,580 Office Action dated Sep. 21, 2016.
U.S. Appl. No. 14/612,604 Notice of Allowance dated Jul. 20, 2016.
U.S. Appl. No. 14/639,425 Notice of Allowance dated Mar. 10, 2017.
U.S. Appl. No. 14/639,425 Office Action dated Jul. 14, 2016.
"U.S. Appl. No. 14/640,385 Supplemental Notice of Allowability dated May 26, 2016".
U.S. Appl. No. 14/693,711 Final Office Action dated Dec. 15, 2016.
U.S. Appl. No. 14/693,711 Notice of Allowability dated May 26, 2017.
U.S. Appl. No. 14/693,711 Notice of Allowance dated Apr. 21, 2017.
U.S. Appl. No. 14/713,178 Advisory Office Action dated Jan. 19, 2017.
U.S. Appl. No. 14/713,178 Final Office Action dated Oct. 14, 2016.
U.S. Appl. No. 14/713,178 Notice of Allowance dated Apr. 12, 2017.
U.S. Appl. No. 14/713,221 Final Office Action dated Jun. 16, 2016.

(56) References Cited

OTHER PUBLICATIONS

U.S. Appl. No. 14/713,221 Non-Final Office Action dated Dec. 30, 2016.
"U.S. Appl. No. 14/713,221 Notice of Allowance dated Oct. 19, 2017".
U.S. Appl. No. 14/713,242 Final Office Action dated Jul. 21, 2017.
U.S. Appl. No. 14/713,242 Office Action dated Dec. 7, 2016.
U.S. Appl. No. 14/921,896 Office Action dated Apr. 26, 2017.
U.S. Appl. No. 15/074,115, filed Mar. 18, 2016.
U.S. Appl. No. 15/089,842, filed Apr. 4, 2016.
U.S. Appn. No. U.S. Appl. No. 14/639,425, filed Mar. 5, 2015.
U.S. Appn. No. U.S. Appl. No. 14/640,385, filed Mar. 6, 2015.
U.S. Appn. No. U.S. Appl. No. 14/693,711 , filed Apr. 22, 2015.
U.S. Appn. No. U.S. Appl. No. 14/713,178, filed May 15, 2015.
U.S. Appn. No. U.S. Appl. No. 14/713,221, filed May 15, 2015.
U.S. Appn. No. U.S. Appl. No. 14/713,242, filed May 15, 2015.
U.S. Appl. No. 14/612,580 Office Action dated Dec. 24, 2015.
USDA. FDA Drug Safety Communication: Clostridium difficile-associated diarrhea can be associated with stomach acid drugs known as proton pump inhibitors (PPIs). Safety announcement. Feb. 8, 2012. Accessed Apr. 1, 2013. http://www.fda.gov/drugs/drugsafety/ucm290510.htm.
USP (32)-NF(27) 2009, Pancreatin, V.3, pp. 3194-3195.
Valicenti-McDermott, et al. Frequency of gastrointestinal symptoms in children with autistic spectrum disorders and association with family history of autoimmune disease. J Dev Behav Pediatr. Apr. 2006;27(2 Suppl):S128-36.
Vargas, et al. Neuroglial activation and neuroinflammation in the brain of patients with autism. Ann Neurol. Jan. 2005;57(1):67-81.
Vellard. The enzyme as drug: application of enzymes as pharmaceuticals. Curr Opin Biotechnol. Aug. 2003;14(4):444-50.
Vilanova, et al. Preparative isolation of the two forms of pig pancreatic pro-(carboxypeptidase A) and their monomeric carboxypeptidases A. Biochem J. Aug. 1, 1985;229(3):605-9.
Viokace—FDA Prescribing Information, Side Effects and Uses. Revised Mar. 2012.
Viokace. Highlights of prescribing information. Aptalis Pharma US Inc. Revised Mar. 2012.
Vojdani, et al. Antibodies against CNS antigens in autism: Possible cross-reaction with dietary proteins and infectious agent antigens. Neuropsychiatric Disorders and Infection. 2004; 19:171-186.
Vojdani, et al. Heat shock protein and gliadin peptide promote development of peptidase antibodies in children with autism and patients with autoimmune disease. Clin Diagn Lab Immunol. May 2004;11 (3):515-24.
Vojdani, et al. Immune response to dietary proteins, gliadin and cerebellar peptides in children with autism. Nutr Neurosci. Jun. 2004;7(3):151-61.
Volkmar, et al. Practice Parameters for the Assessment and Treatment of Children, Adolescents, and Adults with Autism and other Pervasive Developmental Disorders. American Academy of Child and Adolescent Psychiatry. J Am Acad Child Adolesc Psychiatry. (Part 2) Dec. 1999;38(12):1611-6.
Volkmar, et al. Practice parameters for the assessment and treatment of children, adolescents, and adults with autism and other pervasive developmental disorders. American Academy of Child and Adolescent Psychiatry Working Group on Quality Issues. J Am Acad Child Adolesc Psychiatry. (Part 1) Dec. 1999;38(12 Suppl):32S-54S.
Wakefield. Autistic enterocolitis: is it a histopathological entity? Histopathology. 2006; 1-5.
Wakefield. Enterocolitis, Autism, and Measles Virus. Consensus in Child Neurology: Biological Bases and Climical Perspectives in Autism. 2002; 74-81.
Wakefield, et al. Enterocolitis in children with developmental disorders. Am J Gastroenterol. Sep. 2000;95(9):2285-95.
Wakefield, et al. Ileal-lymphoid-nodular hyperplasia, non-specific colitis, and pervasive developmental disorder in children. Lancet. Feb. 28, 1998;351(9103):637-41.
Wakefield, et al. Review article: the concept of entero-colonic encephalopathy, autism and opioid receptor ligands. Aliment Pharmacol Ther. Apr. 2002;16(4):663-74.
Wakefield, et al. The significance of ileo-colonic lymphoid nodular hyperplasia in children with autistic spectrum disorder. Eur J Gastroenterol Hepatol. Aug. 2005;17(8):827-36.
Wakefield. The gut-brain axis in childhood developmental disorders. J Pediatr Gastroenterol Nutr. May-Jun. 2002;34 Suppl 1 :S14-7.
Walsh, et al. Heat shock and the role of the HSPs during neural plate induction in early mammalian CNS and brain development. Cell Mol Life Sci. Feb. 1997;53(2):198-211.
Walsh, et al. Reduced violent behavior following chemical therapy. Physiology and behavior. 2004; 82:835-839.
Wang, et al. Activation of Ras/Erk pathway by a novel MET-interacting protein RanBPM. J Biol Chem. Sep. 27, 2002;277(39):36216-22.
WE MOVE, PD Workbook, The WEMOVE Clinician's Guide to Parkinson's Disease, 2006.
Weintraub, et al. Morphometric studies of pancreatic acinar granule formation in NCTR-Balb/c mice. J Cell Sci. May 1992;102 ( Pt 1):141 -7.
Welch, et al. Brain effects of chronic IBD in areas abnormal in autism and treatment by single neuropeptides secretin and oxytocin. J Mol Neurosci. 2004;25(3):259-74.
Wender et al. Prevalence of attention deficit disorder, residual type, and other psychiatric disorders in patients with irritable colon syndrome. Am J Psychiatry. 1983; 140(12):1579-82 Abstract only.
Whitehouse. Fact Sheet: Combating Autism Act of 2006. www.whitehouse.gov. Dec. 19, 2006.
Williams, et al. Eating habits of children with autism. Pediatr Nurs. May-Jun. 2000;26(3):259-64.
Williams, et al. Intravenous secretin for autism spectrum disorders (ASD). Cochrane Database Syst Rev. Apr. 18, 2012;4:CD003495. doi: 10.1002/14651858.CD003495.pub3.
Wisniewski, et al. Therapeutic approaches for prion and Alzheimer's diseases. Febs J. Aug. 2007;274(15):3784-98. Epub Jul. 6, 2007.
Witmer. ADD and ADHD Statistics—CDC Report Looks at Attention-Deficit/Hyperactivity Disorder. About.com—Parenting of Adolescents. Jul. 15, 2008.
Wohlman et al. Enhancement of drug activity by chymotrypsin, penicillin penetration into granulomatous sesions and inflammatory fluids. Cellular and Molecular Life Sciences. 1969; 25(9):953-954.
"Wolfson, D., Making sense of digestive enzymes, Klaire Labs, Mar. 13, 2006".
Woodward et al. Ischaemic enterocolitis complicating aidiopathic dysatuonomia. Gut. 1998; 43:285-287.
Xu. Pancreatin therapy in chronic pancreatitis. Clin J Dig, May 2005; 25(5):313-315. (in Chinese with English translation).
YAHOO!.com. Who is affected by Parkinson's disease. Yahoo! Health. Jul. 14, 2008.
Yazbak. Autism in the United States: a perspective. Journal of American Physicians and Surgeons. 2003;8:103-107.
Youngberg, et al. Comparison of gastrointestinal pH in cystic fibrosis and healthy subjects. Dig Dis Sci. May 1987;32(5):472-80.
Yuan, et al.. Freeze-Thaw Stability of Three Waxy Maize Starch Pastes Measured by Centrifugation and Calorimetry. Cereal Chem. 1998; 75(4):571-573.
Zeiner, et al. Mammalian protein RAP46: an interaction partner and modulator of 70 kDa heat shock proteins. EMBO J. Sep. 15, 1997;16(18):5483-90.
ZENPEP—FDA Prescribing Information, Side Effects and Uses. Revised Sep. 2014.
ZENPEP. Highlights of prescribing information. Eurand Pharmaceuticals Inc. Revised Jul. 2011.
Zhang et al. Lactulose-mannitol intestinal permeability test in children with diarrhea caused by rotavirus abd cryptosporidium. J of Pediatric Gastro & Nutrition. 2000; 31(1):16-21.
Bouhnik, et al. Lactulose ingestion increases faecal bifidobacterial counts: A randomized double-blind study in healthy humans. European Journal of Clinical Nutrition 58:462-466 (2004).

(56) References Cited

OTHER PUBLICATIONS

P.Ya. Grigoryev et al., Reference Guide on Gastroenterology, Moscow, MIA-2003, pp. 454,460,465.
Tuohy, K.M. et al. Using probiotics and prebiotics to improve gut health. Reviews, Therapeutic Focus, DDT 8(15) Aug. 2003.
U.S. Appl. No. 13/503,844 Final Office Action dated Nov. 30, 2017.
U.S. Appl. No. 15/089,842 Office Action dated Dec. 8, 2017.
U.S. Appl. No. 15/185,511 Notice of Allowance dated Nov. 16, 2017.
National Institutes of Health. Thin Bones Seen in Boys with Autism and Autism Spectrum Disorder. 3 pages (2008).
U.S. Appl. No. 13/733,873 Final Office Action dated Feb. 6, 2020.
U.S. Appl. No. 15/889,917 Final Office Action dated Feb. 13, 2020.
U.S. Appl. No. 15/074,115 Notice of Allowance dated Feb. 11, 2020.
U.S. Appl. No. 16/296,546 Non-Final Office Action dated Feb. 14, 2020.
Wang et al., Extraction of Pancreatin from Pig Pancreas and Isolation and Purification of Kallikrein. Academic Journal of Kunming Medical College 1: 107-108 (2002).
Capua et al., Influenza A viruses grow in human pancreatic cells and cause pancreatitis and diabetes in an animal model. Journal of Virology 87(1): 597-610 (2013).
DeFelice, Viruses Part 2—results of two informal studies, Chapter 14. In: Enzymes: Go with your Gut—more practical guidelines for digestive enzymes. Published by ThunderSnow. pp. 195-218 (2006).
Diagnostic and Statistical Manual of Mental Disorders, Fourth Edition, Text Revision, DSM-IV-TR, American Psychiatric Association (2000).
International Preliminary Reporton Patentability dated Oct. 15, 2019 for PCT/US2018/026841.
Keeley et al., Gradual vs. abrupt withdrawal of methylphenidate in two older dependent males. Journal of Substance Abuse Treatment. 2(2):123-125 (1985).
Lockner et al. Dietary intake and parents' perception of mealtime behaviors in preschool-age children with autism spectrum disorder and in typically developing children. J Am Diet Assoc 108(8):1360-1363 (2008).
Naver.com entry for Rare Disease Information: Osteopenia—Osteopsathyrosis, Fragilitasossium, Fragilitasossium (accessed Sep. 25, 2019).
Pending U.S. Appl. No. 16/499,988, filed Oct. 1, 2019.
Singh et al. Past, Present, and Future Technologies for Oral Delivery of Therapeutic Proteins. J Pham Sci 97(7):2497-2523 (2008).
U.S. Appl. No. 13/757,412 Final Office Action dated Sep. 12, 2017.
U.S. Appl. No. 16/103,192 Office Action dated Nov. 4, 2019.
U.S. Appl. No. 15/354,940 Final Office Action date Aug. 21, 2019.
U.S. Appl. No. 15/074,115 Notice of Allowance dated Dec. 11, 2019.
U.S. Appl. No. 15/265,620 Non-Final Office Action dated Jan. 30, 2020.
U.S. Appl. No. 15/889,917 Office Action dated May 24, 2019.
Amsterdam, D. Susceptibility testing of antimicrobials in liquid media. Antibiotics in Laboratory Medicine. 52-111 (1996).
Barboza et al., Measurement of intestinal permeability using mannitol and lactulose in children with diarrheal diseases. Brazilian Journal of Medical and Biological Research 32: 1499-1504 (1999).
Barry, J. Mode of action of penetration enhancers in human skin. Controlled Release 6: 85-97 (1987).
D'Eufemia et al., Abnormal intestinal permeability in children with autism. Acta Paediatr 85: 1076-1079(1996).
Fan et al., Guidelines for Standard Operation of Toxicological Safety Assessment (vol. 1). University of Electronic Science and Technology Press (2009).
Harrison, Bipolar Disorder. Healing Depression Naturally, Twin Streams. Kensington Publishing Corp: 31-32. (2004).
Horsmans et al., Lactulose improves psychometric testing in cirrhotic patients with subclinical encephalopathy. Aliment Pharmacol Ther 11:165-170 (1997).
Schlessingerman, Mass of an Adult. The Physics Factbook (2003).
Thomas, Bipolar Disorder-Balancing Moods by Balancing Nutrients; What Doctors Don't Tell You. 14)7): 1-13 (2003).
U.S. Appl. No. 13/002,136 Final Office Action dated Sep. 11, 2020.
U.S. Appl. No. 15/889,917 Non-Final Office Action dated Sep. 3, 2020.
U.S. Appl. No. 16/281,908 Notice of Allowance dated Nov. 3, 2020.
U.S. Appl. No. 16/422,079 Final Office Action dated Sep. 16, 2020.
U.S. Appl. No. 12/535,676 Notice of Allowance dated Apr. 1, 2020.
U.S. Appl. No. 13/002,136 Non-Final Office Action dated May 26, 2020.
U.S. Appl. No. 13/757,412 Non-Final Office Action dated Mar. 18, 2020.
U.S. Appl. No. 14/713,242 Notice of Allowance dated Apr. 2, 2020.
U.S. Appl. No. 15/265,620 Notice of Allowance dated Apr. 29, 2020.
U.S. Appl. No. 15/354,940 Final Office Action dated Jul. 2, 2020.
U.S. Appl. No. 16/281,908 Non-Final Office Action dated May 1, 2020.
U.S. Appl. No. 16/422,079 Non-Final Office Action dated Apr. 20, 2020.
Xie, Development and Application of New Traditional Chinese Medicine 2nd Edition. People's Medical Publishing House (2000).
Merriam Webster Dictionary: definition of prevent.
Molinari et al., Fecal chymotrypsin and alastase-1 determination on one single stool collected at random: diagnostic value for exocrine pancreatic status. Clinical Biochemistry 37: 758-763 (2004).
Nater et al., Determinants of the diurnal course of salivary alpha-amylase. Psychoneuroendocrinology 32: 392-401 (2007).
The Diagnostic and Statistical Manual of Mental Disorders (DSM IV), published by the American Psychiatric Association, Fourth Edition, Primary CareVersion, Washington, DC, American Psychiatric Association, (2000).
Types of Fats, Healthwise-Mich Med, pp. 1-2, downloaded from https://www/uofmhealth.org/health-library/aa160619 on Feb. 3, 2021.
U.S. Appl. No. 13/002,136 Notice of Allowance dated Feb. 24, 2021.
U.S. Appl. No. 13/757,412 Final Office Action dated Dec. 22, 2020.
U.S. Appl. No. 15/889,917 Notice of Allowance dated Mar. 29, 2021.
U.S. Appl. No. 16/103,192 Non-Final Office Action dated Feb. 10, 2021.
U.S. Appl. No. 16/281,937 Non-Final Office Action dated Mar. 17, 2021.
U.S. Appl. No. 16/422,079 Notice of Allowance dated Mar. 3, 2021.
U.S. Appl. No. 16/422,462 Non-Final Office Action dated Jul. 22, 2021.
U.S. Appl. No. 16/884,701 Non-Final Office Action dated Jun. 10, 2021.

\* cited by examiner

COMPOSITIONS AND METHODS FOR THE TREATMENT OR THE PREVENTION OF *E. COLI* INFECTIONS AND FOR THE ERADICATION OR REDUCTION OF *E. COLI* SURFACES

CROSS-REFERENCE TO RELATED APPLICATIONS

This application is a continuation of U.S. application Ser. No. 14/713,221, filed May 15, 2015, now U.S. Pat. No. 9,895,427, which is a continuation application of U.S. application Ser. No. 13/144,290, filed Jul. 12, 2011, now U.S. Pat. No. 9,084,784, which is a U.S. § 371 National Stage Application of PCT/US2010/020259, filed Jan. 6, 2010, which claims the benefit of U.S. Provisional Applications Ser. No. 61/142,718, filed Jan. 6, 2009; 61/153,279, filed Feb. 17, 2009; and 61/170,856, filed Apr. 20, 2009, each of which is hereby incorporated by reference in its entirety.

TECHNICAL FIELD

This disclosure relates to compositions, including pharmaceutical compositions such as antibiotic compositions, and methods of using the same for treating or preventing *E. coli* infections in humans and other animals. This disclosure also relates to compositions, such as disinfectants, sanitizers, antiseptics, and detergents, and methods of using the same for eradicating or reducing the presence of *E. coli*. on surfaces, including inanimate and biological surfaces (e.g., skin, wounds), and/or for attenuating the infectivity of *E. coli* in order to prevent and/or to reduce the spread of *E. coli* infections.

BACKGROUND

*Escherichia coli* (*E. coli*) is a type of bacteria that can cause severe human illness. While there are many types of *E. coli* bacteria, only certain types cause food borne illness. Hundreds of harmless strains of *E. coli* can be found widely in nature, including the intestinal tracts of humans and other warm-blooded animals. Disease-causing strains, however, are a frequent cause of both intestinal and urinary-genital tract infections.

In 1982, scientists identified the first harmful food borne strain of *E. coli* in the United States. The disease-causing food borne *E. coli* most commonly found in this country is called O157:H7. Cattle are the main sources of *E. coli* O157:H7, but these bacteria also can be found in other domestic and wild mammals. *E. coli* serotype O157:H7 is a rare variety of *E. coli* that produces large quantities of one or more related, potent toxins that cause severe damage to the lining of the intestine.

Several different strains of harmful *E. coli* can cause diarrheal disease. Particularly dangerous types of *E. coli*, such as *E. coli* O157:H7, produce one or more kinds of toxins (poisons) called Shiga toxins. Shiga toxins can severely damage the lining of intestines and kidneys. These types of bacteria are called Shiga toxin-producing *E. coli* (STEC). STEC often causes bloody diarrhea and can lead to kidney failure in children or in people with weakened immune systems. STEC is also refered to as verocytotoxic *E. coli* (VTEC) or enterohemorrhagic *E. coli* (EHEC); these all refer generally to the same group of bacteria. The most commonly identified STEC in North America is *E. coli* O157:H7 (often shortened to *E. coli* O157 or even just "O157").

Enterotoxigenic *E. coli* (ETEC), which produce a different toxin, can cause diarrhea. These strains typically cause so-called travelers' diarrhea because they commonly contaminate food and water in developing countries. Enteropathogenic *E. coli* (EPEC) cause persistent diarrhea (lasting 2 weeks or more) and are more common in developing countries where they can be transmitted to humans through contaminated water or contact with infected animals. Other types of *E. coli*, including 026:H11 and 0111:H8, also have been found in the United States and can cause disease in people.

*E. coli* infection is characterized by severe cramping (abdominal pain) and diarrhea that is initially watery but becomes grossly bloody. Occasionally vomiting occurs. Fever is either low-grade or absent. The illness is usually self-limited and lasts for an average of 8 days. Some individuals exhibit watery diarrhea only.

Hemorrhagic colitis is diagnosed by isolation of *E. coli* of serotype O157:H7 or other verotoxin-producing *E. coli* from diarrheal stools. Alternatively, the stools can be tested directly for the presence of verotoxin. Confirmation can be obtained by isolation of *E. coli* of the same serotype from the incriminated food.

In addition to *E. coli* O157, many other kinds (called serogroups) of STEC cause disease. These other kinds are sometimes called "non-O157 STEC." *E. coli* serogroups O26, O111, and O103 are the non-O157 serogroups that most often cause illness in people in the United States.

People of any age can become infected with STEC. Very young children and the elderly are more likely to develop severe illness and hemolytic uremic syndrome (HUS) than others, but even healthy older children and young adults can become seriously ill. The symptoms of STEC infections vary for each person but often include severe stomach cramps, diarrhea (often bloody), and vomiting.

Around 5 to 10% of those who are diagnosed with STEC infection develop a potentially life-threatening complication known as hemolytic uremic syndrome (HUS). Clues that a person is developing HUS include decreased frequency of urination, feeling very tired, and losing pink color in cheeks and inside the lower eyelids. Persons with HUS should be hospitalized because their kidneys may stop working and they may develop other serious problems. Most persons with HUS recover within a few weeks, but some suffer permanent damage or die.

STEC live in the guts of ruminant animals, including cattle, goats, sheep, deer, and elk. The major source for human illnesses is cattle. STEC that cause human illness generally do not make animals sick. Other kinds of animals, including pigs and birds, sometimes acquire STEC from the environment and may carry or spread it.

SUMMARY

This disclosure relates to the prevention and/or treatment of *E. coli* infections, including antibiotic-resistant and virulent *E. coli* infections, such as STEC, ETEC, or EPEC, with the use of a pharmaceutical composition comprising one or more digestive enzymes, such as pancreatic or other digestive-track enzymes (e.g., porcine pancreatic enzymes) or plant-, fungal-, or microorganism-derived enzymes, that break down components of food. As used herein, a pharmaceutical composition can be used for human or veterinary indications. Accordingly, the pharmaceutical compositions can be useful for prophylactic and/or therapeutic treatment of human or other mammalian populations (e.g., pig, horse, cow, sheep, goat, monkey, rat, mouse, cat, dog) or of bird populations (e.g., duck, goose, chicken, turkey).

The pharmaceutical compositions can be used on their own, and/or in combination with other antibacterial or antibiotic (e.g., anti-*E. coli*) regimens, and/or with other therapeutic or antibiotic agents post-infection to treat *E. coli* infections.

Also provided herein are bacteriocidal and/or bacteriostatic compositions comprising one or more digestive enzymes for use as or in disinfectants, sanitizers, detergents, and antiseptics, e.g., in hospitals, nursing homes, nurseries, daycares, schools, work environments, food service settings, public transportation and restroom facilities, to reduce, attenuate, and/or destroy *E. coli* present in such settings. The surfaces treated with the described compositions can be large (e.g., operating room tables, doors, changing tables, ventilation systems) or small (e.g., medical devices, door handles); inanimate or non-living (tables) or living tissue (hands, e.g., detergents for hand-washing; wounds, e.g., surgical wounds or wounds resulting from accidents/trauma). The compositions can thus be useful to treat surfaces to reduce or eradicate *E. coli* thereon, or to attenuate or reduce the infectivity of *E. coli*, and thereby prevent or reduce the spread of *E. coli*.

Accordingly, it is an object of the present disclosure to provide a method for the treatment or prevention of *E. coli* infection in a bird or a mammal, comprising administering to the bird or mammal a therapeutically effective amount of a pharmaceutical composition comprising one or more digestive enzymes. In some embodiments, the one or more digestive enzymes comprise one or more enzymes selected from the group consisting of proteases, amylases, celluloses, sucrases, maltases, papain, and lipases. In some embodiments, the one or more digestive enzymes comprise one or more pancreatic enzymes. The one or more digestive enzymes are, independently, derived from an animal source, a microbial source, a plant source, a fungal source, or are synthetically prepared. In some embodiments, the animal source is a pig pancreas.

In some embodiments, a pharmaceutical composition comprises at least one amylase, a mixture of proteases comprising chymotrypsin and trypsin, and at least one lipase. In some embodiments, a pharmaceutical composition comprises at least one protease and at least one lipase, and wherein the ratio of total proteases to total lipases (in USP units) ranges from about 1:1 to about 20:1.

In some embodiments, the pharmaceutical composition is a dosage formulation selected from the group consisting of: pills, tablets, capsules, caplets, sprinkles, creams, lotions, aerosols, emulsions, powders, liquids, gels, and a combination of any thereof.

In some embodiments, the pharmaceutical composition is formulated for oral administration, or for topical administration, or for intranasal, or for transmucosal administration.

Also provided is a method of treating a mammal or bird exhibiting one or more symptoms of an *E. coli* infection comprising administering to the mammal or bird a therapeutically effective amount of a composition comprising one or more digestive enzymes.

Further provided is a method for treating diarrhea comprising administering a pharmaceutical composition comprising one or more digestive enzymes to an individual. The disclosure also features a method for sanitizing or disinfecting a surface to reduce the amount of *E. coli* thereon or to eradicate the *E. coli* thereon, comprising applying to the surface a composition comprising one or more digestive enzymes. The surface can be a living surface (e.g., skin, wound) or an inanimate or non-living surface (e.g., medical device, food product).

Also provided herein is a method for reducing the amount of *E. coli* present on a skin region, tissue, or wound of a mammal or bird comprising applying to the skin region, tissue, or wound a composition comprising one or more digestive enzymes.

Also featured is a disinfectant comprising one or more digestive enzymes, wherein the disinfectant has a phenol coefficient of >1 to about 20 for *S. aureus* or *E. coli*.

The disclosure also provides an antibiotic comprising one or more digestive enzymes, wherein the antibiotic is bacteriocidal and/or bacteriostatic for *E. coli*.

Similarly, a detergent comprising one or more digestive enzymes is also provided, wherein the detergent is bacteriocidal and/or bacteriostatic for *E. coli*.

Also provided is an antiseptic comprising one or more digestive enzymes, wherein the antiseptic is bacteriocidal and/or bacteriostatic for *E. coli*.

The disclosure also provides a disinfectant comprising one or more digestive enzymes, wherein the disinfectant is bacteriocidal and/or bacteriostatic for *E. coli*.

The details of one or more embodiments of the invention are set forth in the accompanying drawings and the description below. Any reference disclosed herein, such as a patent, patent application, specification, book, article, or scientific publication, is incorporated by reference in its entirety. Other features, objects, and advantages of the invention will be apparent from the description and drawings, and from the claims.

DETAILED DESCRIPTION

The term "administration" or "administering" refers to a method of giving a dosage of a composition or pharmaceutical composition to a vertebrate or invertebrate, including a mammal, a bird, a fish, or an amphibian, where the method is by any route, e.g., intrarespiratory, nasal, topical, oral, intravenous, intraperitoneal, intramuscular, transmucosal, buccal, rectal, vaginal, or sublingual. The preferred method of administration can vary depending on various factors, e.g., the components of the pharmaceutical composition, the site of the disease, the disease involved, and the severity of the disease.

The term "mammal" is used in its usual biological sense. Thus, it specifically includes humans, cattle, horses, dogs, and cats, but also includes many other species.

The term "pharmaceutically acceptable carrier" or "pharmaceutically acceptable excipient" includes any and all solvents, dispersion media, coatings, isotonic and absorption delaying agents and the like. The use of such media and agents for pharmaceutically active substances is well known in the art. Except insofar as any conventional media or agent is incompatible with the active ingredients, its use in the therapeutic compositions is contemplated. Supplementary active ingredients, such as antibiotics, antifungals, antimicrobials, can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (2006); Goodman and Gilman's: The Pharmacological Basis of Therapeutics, 11th Ed., The McGraw-Hill Companies.

"Subject" or "patient" or "individual" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

By "therapeutically effective amount" or "pharmaceutically effective amount" is typically one which is sufficient to achieve the desired effect and may vary according to the nature and severity of the disease condition, the nature of the subject, and the potency of the composition. It will be appreciated that different concentrations may be employed for prophylaxis than for treatment of an active disease. This amount can further depend upon the patient's height, weight, sex, age and medical history.

A therapeutic effect relieves, to some extent, one or more of the symptoms of the disease, and includes curing a disease. "Curing" means that the symptoms of active disease are eliminated. However, certain long-term or permanent effects of the disease may exist even after a cure is obtained (such as tissue damage).

"Treat," "treatment," or "treating," as used herein refers to administering a pharmaceutical composition for therapeutic purposes. The term "therapeutic treatment" refers to administering treatment to a patient already suffering from a disease thus causing a therapeutically beneficial effect, such as ameliorating existing symptoms, preventing additional symptoms, ameliorating or preventing the underlying metabolic causes of symptoms, postponing or preventing the further development of a disorder and/or reducing the severity of symptoms that will or are expected to develop.

The present disclosure provides compositions comprising one or more digestive enzymes and methods of using the same for the treatment and/or prevention of *E. coli* infections, including antibiotic-resistant forms of *E. coli* and virulent forms such as STEC, ETEC, or EPEC. The present disclosure also provides compositions comprising one or more digestive enzymes and methods of using the same as antiseptics, detergents, disinfectants, and sanitizers, e.g., as bacteriocidal and/or bacteriostatic compositions, to eradicate or attenuate the *E. coli* and/or to reduce its infectivity. The compositions described herein include one or more digestive enzymes, which are postulated to assist in the reduction, weakening, or eradication of *E. coli*, and thus to prevent contraction of *E. coli* infections or to treat *E. coli* infections (e.g., improve or ameliorate the symptoms or reduce the time course of the infection).

Compositions

A composition for use as described herein can include one or more digestive enzymes. While not being bound by theory, it is believed that the digestive enzyme(s) in the composition can degrade *E. coli* cell wall, membrane, and/or protein structures, leading to the bacteriostatic and/or bacteriocidal activity. The compositions demonstrate species-specific bacteriocidal/bacteriostatic activity against *S. aureus* and *E. coli*, but not against *S. enterica*, possibly demonstrating that the vulnerability of the two organisms derives from proteolytic degradation of a similar protein sequence present in the two organisms.

A digestive enzyme as described herein is an enzyme that can break down one or more components of food (e.g., proteins, fats, carbohydrates). The digestive enzymes can be animal-derived (e.g., pancreatic or other digestive-track enzymes), or plant-, fungal-, or microorganism-derived enzymes, or can be synthetically prepared. Many digestive enzymes are commercially available or can be isolated and purified from other sources by methods well known to those having ordinary skill in the art. Enzymatic activity of the enzymes can also be evaluated using standard assays.

The digestive enzymes can be used in any combination of type of enzyme and any combination of enzyme sources. In some embodiments, the one or more digestive enzymes comprise one or more enzymes selected from the group consisting of proteases, amylases, celluloses, sucrases, maltases, papain (e.g., from *papaya*), bromelain (e.g., from pineapple), hydrolases, and lipases. In some embodiments, the one or more digestive enzymes comprise one or more pancreatic enzymes. In some embodiments, the composition comprises one or more proteases, one or more lipases, and one or more amylases. In some embodiments, the one or more proteases comprise chymotrypsin and trypsin. In some embodiments, a composition as described herein consists essentially of, or consists of, the one or more digestive enzymes.

In certain embodiments, the composition can comprise at least one amylase, at least two proteases, and at least one lipase. In certain embodiments, the composition can further include one or more hydrolases, papain, bromelain, *papaya*, celluloses, pancreatin, sucrases, and maltases.

As indicated, the one or more digestive enzymes can be derived from an animal source. In some embodiments, the animal source is a pig, e.g., a pig pancreas. Pig pancreatic enzyme extracts and formulations are known to those having ordinary skill in the art and are commercially available or can be prepared using known methods. For example, a pancreatic enzyme composition can be purchased from Scientific Protein Laboratories (designated PEC). A pancreatic enzyme composition, or any composition herein, can be adjusted to modify the amount of one or more digestive enzymes contained therein, e.g., the lipase, amylase, or protease content, such as by production and/or processing methods or by the selective addition of exogenous enzymes, activators, or inhibitors to the composition.

In certain circumstances, it may be desirable to have relatively higher activity of proteases than lipases. Thus, in some embodiments, a composition comprises at least one protease and at least one lipase, wherein the ratio of total proteases to total lipases (in USP units) ranges from about 1:1 to about 20:1 including 1:1, 2:1, 3;1, 4:1, 5;1, 6:1, 7:1, 8:1, 9:1, 10:1, 11;1, 12;1, 13;1, 14:1, 15:1, 16;1, 17:1, 18:1, 19:1 and 20:1, long with all values in-between. In some embodiments, the ratio of proteases to lipases ranges from about 4:1 to about 10:1 including 4:1, 5:1, 6:1, 7:1, 8:1, 9:1, and 10:1, along with all values in-between.

In certain circumstances it may be useful to modify the amount of a particular enzymatic activity in a given composition. The activity of the one or more digestive enzymes can be adjusted in a variety of ways known to the skilled artisan, e.g., by increasing the amount of the particular enzyme, or by adjusting the components of the composition, e.g., via the use of stabilizers, inhibitors, and activators. In some embodiments, a composition described herein includes one or more proteases having an activity of from about 0.05 to about 400 USP Units per mg of the composition, or any value therebetween (e.g., 0.1; 0.2; 0.25; 0.5; 1, 2, 5, 10, 15, 20, 25, 30, 35, 40, 45, 50, 55, 60, 65, 75, 100, 150, 200, 250, 300, 350 USP Units per mg). In some embodiments, a composition described herein includes one or more lipases having an activity of from about 0.005 to about 50 Units per mg of the composition, or any value therebetween (e.g., 0.01, 0.02, 0.025, 0.03, 0.04, 0.05, 0.06, 0.08, 0.1, 0.2, 0.5, 1, 2, 3, 4, 5, 6, 7, 8, 9, 10, 12, 14, 16, 18, 20, 22, 25, 28, 30, 35, 38, 40, 45 USP Units per mg). In some embodiments, a composition described herein includes one or more amylases having an activity of from about 0.05 to about 400 USP Units per mg of the composition, or any value therebetween (e.g., 0.1; 0.2; 0.25; 0.5; 1, 2, 5, 10, 15, 20, 25, 30, 35, 40, 45, 50, 55, 60, 65, 75, 100, 150, 200, 250, 300, 350 USP Units per mg). In some embodiments, a composition described herein includes one or more proteases in the above activity range, one or more lipases in the above activity range, and one or more amylases in the above activity range. One exemplary embodiment includes one or more proteases having an activity in the range of about 150-250 USP units/mg; one or more lipases having an activity in the range of about 20-40 USP units/mg; and one or more amylases having an activity in the range of about 200-300 USP units/mg.

In some embodiments, a composition can be formulated so as to stabilize the one or more digestive enzymes, e.g., to preserve the enzymatic activity of the enzymes. Stabilization techniques can limit or prevent auto-degradation of the one or more enzymes in a composition and help maintain enzymatic activity, increase shelf-life, and aid in the tolerance of the activity of the compositions to changes in temperature, humidity, and storage conditions. For example, in some embodiments, the one or more enzymes in the composition are encapsulated, e.g., lipid-encapsulated. In other applications, variations in excipients, pH, enzyme inhibitors, etc. can be employed to aid in stabilizing the enzymes. Appropriate stabilization techniques will depend on the intended application for the composition (e.g., antibiotic vs. detergent), the route of administration, the form of the composition, the intended site of delivery/activity, and other factors, and can be determined by those having ordinary skill in the art.

Certain useful enzyme activity stabilizers include compounds that provide a source of free calcium in a solution such as for example calcium salts; alkyl or branched alcohols such as for example ethanol and isopropyl alcohol; alkanolamines such as for example triethanolamine; acids, such as organic acids; and mixtures of petroleum distillates.

In certain embodiments, an enzyme activity stabilizer can be a composition selected from (1) compositions known to be effective in stabilizing enzymes in liquid aqueous solutions, including enzyme stabilizing compounds and systems, (2) selected "micelle inhibitors", and mixtures of (1) and (2). In some embodiments, the activity stabilizer is a suitable concentration of boron anions. In some cases, the activity stabilizer is solvated in a polyol and may be combined with enzyme stabilizing synergists or adjuvants forming an enzyme stabilizing system. Preferred "micelle inhibitors" include species known to modify as well as to inhibit micelle formation and may be selected from water miscible solvents such as C1-C6 alkanols, C1-C6 diols, C2-C24 alkylene glycol ethers, alkylene glycol alkyl ethers, and mixtures thereof. A highly preferred micelle inhibitor is di-(propylene glycol) methyl ether ("DPM") and analogues thereof which modify micelle formation.

One example of an "enzyme stabilizing system" is a boron compound (e.g. boric acid) which in the past has been used alone or with selected other adjuvants and or synergists (e.g. polyfunctional amino compounds, antioxidants, etc) to protect proteolytic and other enzymes in storage and in various products.

An activity stabilizer may be chosen to substantially minimize the Minimum Inhibitory Concentration ("MIC") of digestive enzyme in the formulation. MIC is a measure of the minimum concentration of the biocide which succeeds in preventing bacterial growth in a culture during a specified time period, for example 24 hrs. Details of the MIC test are shown in "Bailey & Scott 'Diagnostic Microbiology', 8th edition, 1990 at page 177.

In some embodiments, a composition described herein can be coated with a variety or natural or synthetic coatings, e.g., to provide timed release of the enzymes, to provide flavor or odor masking, or to stabilize the enzymes. Coated enzyme preparations, including lipid-coated or lipid-encapsulated enzyme compositions, comprising one or more digestive enzymes useful for the methods and compositions described herein are disclosed in U.S. Ser. No. 12/386,051, filed Apr. 13, 2009, incorporated herein by reference in its entirety. Such coated preparations can provide desired features, including increased shelf stability, reduced aerosolization of powder or solid formulations, odor and taste-masking, enzyme stabilization, and delayed or timed release of the enzymes.

Other additives for inclusion in the compositions described herein can be determined by those having ordinary skill in the art, and will be based on a number of features, including intended application, e.g., human vs. veterinary applications; desired release profile; desired pharmacokinetics; safety; stability; and physical characteristics (smell, color, taste, pour, aerosilization). Suitable formulation ingredients, excipients, binders, bulking agents, flavorants, colorants, etc. can be determined and evaluated by methods known to those having ordinary skill.

Pharmaceutical Compositions and Antibiotics for Human or Veterinary Use

Compositions described herein can be formulated as pharmaceutical compositions, e.g., can include a composition as described previously formulated with one or more pharmaceutically acceptable carriers or excipients. The pharmaceutical compositions are useful for treating or preventing *E. coli* infections in humans and other animals, such as mammals (e.g., cows, horses, pigs, sheep, goat, monkey, cats, dogs, mice, rats) and birds (chickens, turkeys, ducks, geese). A pharmaceutical composition for treating *E. coli* infections can also be referred to as an antibiotic or antibiotic composition herein.

The susceptibility of *E. coli*, including virulent and resistant forms, to an antibiotic composition described herein can be determined by methods known to those having ordinary skill in the art. One rapid procedure uses commercially filter paper disks that have been impregnated with a specific quantity of the antibiotic composition. These disks are placed on the surface of agar plates that have been streaked with a culture of the *E. coli* being tested, and the plates are observed for zones of growth inhibition. The broth dilution susceptibility test involves preparing test tubes containing serial dilutions of the composition in liquid culture media, then inoculating the organism being tested into the tubes. The lowest concentration of drug that inhibits growth of the bacteria after a suitable period of incubation is reported as the minimum inhibitory concentration (MIC).

The resistance or susceptibility of *E. coli* to an antibiotic described herein can be determined on the basis of clinical outcome, i.e., whether administration of that antibiotic to a subject infected by that organism will successfully cure the subject. Alternatively, to facilitate the identification of antibiotic resistance or susceptibility using in vitro test results, the National Committee for Clinical Laboratory Standards (NCCLS) has formulated standards for antibiotic susceptibility that correlate clinical outcome to in vitro determinations of the minimum inhibitory concentration of antibiotic.

Administration of the pharmaceutical compositions herein can be via any of the accepted modes of administration for agents that serve similar utilities including, but not limited to, orally, subcutaneously, intravenously, intranasally, topically, transdermally, transmucosally, intraperitoneally, intramuscularly, intrapulmonarilly, vaginally, rectally, or intraocularly. Oral, transmucosal, topical, and parenteral administrations, for example, are customary in treating *E. coli* infection indications.

In the pharmaceutical compositions, effective concentrations of one or more digestive enzymes are mixed with a suitable pharmaceutical excipient or carrier. The concentrations of the digestive enzymes in the compositions are effective for delivery of an amount, upon administration, that is useful in the reduction or eradication of *E. coli* bacteria, and/or to treat or ameliorate of one or more of the symptoms associated with *E. coli* infection.

Antibiotic compositions can be formulated for single dosage administration. To formulate a composition, the weight fraction of digestive enzymes is dissolved, suspended, dispersed or otherwise mixed in a selected carrier at an effective concentration such that the bacteria are reduced or eradicated, the treated condition is relieved, or one or more symptoms are ameliorated.

The digestive enzymes are included in the pharmaceutically acceptable carrier in an amount sufficient to exert a therapeutically useful effect in the absence of undesirable side effects on the patient treated. The therapeutically effective concentration may be determined empirically by testing the digestive enzymes in in vitro and in vivo, and then extrapolated therefrom for dosages for humans.

The concentration of digestive enzymes in the pharmaceutical composition will depend on absorption, inactivation and excretion rates of the enzymes, the physicochemical characteristics of the enzymes, the dosage schedule, the dosage form, and amount administered as well as other factors known to those of skill in the art.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Upon mixing or addition of the digestive enzymes, the resulting mixture may be a solution, suspension, gel, powder, emulsion or the like. The form of the resulting mixture depends upon a number of factors, including the intended mode of administration and the solubility of the digestive enzymes in the selected carrier or vehicle.

Compositions intended for pharmaceutical use may be administered as crystalline or amorphous products. Pharmaceutically acceptable compositions include solid, semi-solid, liquid, gel, powder, and aerosol dosage forms, such as, e.g., tablets, capsules, caplets, sprinkles, powders, liquids, suspensions, emulsions, gels, suppositories, aerosols or the like. They may be obtained, for example, as films by methods such as precipitation, crystallization, freeze drying, spray drying, or evaporative drying. Microwave or radio frequency drying may be used for this purpose. The compositions can also be administered in sustained or controlled release dosage forms, including depot injections, osmotic pumps, pills, specialized coatings (e.g., enteric coatings) on oral dosage forms, transdermal (including electrotransport) patches, and the like, for prolonged and/or timed, pulsed administration at a predetermined rate. In some embodiments, the compositions are provided in unit dosage forms suitable for single administration of a precise dose.

The compositions can be administered either alone or more typically in combination with a conventional pharmaceutical carrier, excipient or the like. The term "excipient" is used herein to describe any ingredient other than the compound(s) (enzymes) used in the composition. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, scrum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-b-cyclodextrins, or other solubilized derivatives can also be advantageously used to enhance delivery of compositions described herein. Actual methods of preparing such dosage forms are known, or will be apparent, to those skilled in this art; for example, see *Remington: The Science and Practice of Pharmacy,* 21st Edition (Lippincott Williams & Wilkins. 2005).

In one preferred embodiment, the compositions will take the form of a unit dosage form such as a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, solution or suspension (e.g., in propylene carbonate, vegetable oils or triglycerides) is encapsulated in a gelatin capsule. Unit dosage forms in which two or more ingredients are physically separated are also contemplated; e.g., capsules with granules of enzyme(s) and granules of other ingredients; two-layer tablets; two-compartment gel caps, etc.

Liquid pharmaceutically administrable compositions can, for example, be prepared by dissolving, dispersing, etc. one or more digestive enzymes and optional pharmaceutical adjuvants in a carrier (e.g., water, saline, aqueous dextrose, glycerol, glycols, ethanol or the like) to form a solution or suspension. If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Injectables can be prepared in conventional forms, either as liquid solutions or suspensions, as emulsions, or in solid forms suitable for dissolution or suspension in liquid prior to injection.

Solid compositions can be provided in various different types of dosage forms, depending on the physicochemical properties of the enzymes, the desired dissolution rate, cost considerations, and other criteria. In one of the embodiments, the solid composition is a single unit. This implies that one unit dose of the drug is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In one embodiment, the solid composition is a highly porous lyophilized form. Such lyophilizates, sometimes also called wafers or lyophilized tablets, are particularly useful for their rapid disintegration, which also enables the rapid dissolution of the active compound.

On the other hand, for some applications the solid composition may also be formed as a multiple unit dosage form. Examples of multiple units are powders, sprinkles, granules, microparticles, microcapsules, pellets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution. In another embodiment, the solid composition is a sprinkle formulation.

Another type of multiparticulate system which is also capable of achieving rapid drug dissolution is that of powders, granules, or pellets from water-soluble excipients which are coated with the composition ingredients (e.g., enzymes), so that the enzymes are located at the outer surface of the individual particles. In this type of system, the water-soluble low molecular weight excipient is useful for preparing the cores of such coated particles, which can be subsequently coated with a coating composition comprising the enzyme(s) and, preferably, one or more additional excipients, such as a binder, a pore former, a saccharide, a sugar alcohol, a film-forming polymer, a plasticizer, or other excipients used in pharmaceutical coating compositions.

Appropriate dosages for treating or preventing *E. coli* infections will depend on the patient (species, age, weight, health), the severity of the disease, the strain of the *E. coli* present, the type of formulation (e.g., liquid or ointment) and other factors known to those having ordinary skill in the art. It is to be noted that concentrations and dosage values may vary with the severity of the condition to be alleviated. It is to be further understood that for any particular patient, specific dosage regimens should be adjusted over time according to the individual need and the professional judgment of the person administering or supervising the administration of the compositions.

In some embodiments, the pharmaceutical composition comprises per dose: amylases from about 10,000 to about 60,000 U.S.P, including 10,000, 15,000, 20,000, 25,000, 30,000, 35,000, 40,000, 45,000, 50,000, 55,000, and 60,000 U.S.P, along with all values in-between, proteases from about 10,000 to about 70,000 U.S.P, including 10,000, 15,000, 20,000, 25,000, 30,000, 35,000, 40,000, 45,000, 50,000, 55,000, 60,000, 65,000, and 70,000, along with all values in-between, and lipases from about 4,000 to about 30,000 U.S.P, including, 4,000, 5,000, 10,000, 15,000, 20,000, 25,000, and 30,000, along with all values in-between. A pharmaceutical composition can include one or more of: chymotrypsin from about 2 to about 5 mg including 2.0, 2.5, 3.0, 3.5, 4.0, 4.5, and 5.0 mg, along with all values in-between; trypsin from about 60 to about 100 mg including 50, 65, 70, 75, 80, 85, 90, 95, and 100 mg, including all values in between; papain from about 3,000 to about 10,000 USP units including 3,000, 4,000, 5,000, 6,000, 7,000, 8,000, 9,000, and 10,000 USP, along with all values in between; and *papaya* from about 30 to about 60 mg, including 30, 35, 40, 45, 50, 55, and 60 mg, along with all values in between.

Additional information on particular dosage forms of the compositions is provided below.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

a. Solid Compositions for Oral Administration

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The digestive enzymes could be provided in a composition that protects it from the acidic environment of the stomach. For example, the composition can be formulated in an enteric coating that maintains its integrity in the stomach and releases the digestive enzymes in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The digestive enzymes can also be administered as a component of an elixir, suspension, syrup, wafer, sprinkle, chewing gum or the like. A syrup may contain, in addition to the active digestive enzymes, sucrose as a sweetening agent and certain preservatives, dyes and colorings and flavors.

The digestive enzymes can also be mixed with other active materials which do not impair the desired action, or with materials that supplement the desired action, such as antacids, $H_2$ blockers, and diuretics. Higher concentrations, up to about 98% by weight of the digestive enzymes may be included.

In all embodiments, tablets and capsules formulations may be coated as known by those of skill in the art in order to modify or sustain dissolution of the digestive enzymes. Thus, for example, they may be coated with a conventional enterically digestible coating, such as phenylsalicylate, waxes and cellulose acetate phthalate.

b. Liquid Compositions for Oral Administration

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is in one embodiment encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the digestive enzymes in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Patent No. RE28,819 and U.S. Pat. No. 4,358,603. Briefly, such formulations include, but are not limited to, those containing digestive enzymes provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

2. Injectables, Solutions and Emulsions

Parenteral administration, in one embodiment characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, digestive enzymes provided herein are dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The digestive enzymes diffuse through the outer polymeric membrane in a release rate controlling step. The percentage of digestive enzymes contained in such parenteral compositions is highly dependent on the specific nature thereof, as well as the activity of the digestive enzyme or mixture thereof and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or non aqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing digestive enzymes is an effective mode of administration. Another embodiment is a sterile aqueous or oily solution or suspension containing digestive enzymes that can be injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the digestive enzymes to the treated tissue(s).

The digestive enzymes may be suspended in micronized or other suitable foiui or may be derivatized to produce a more soluble active product. The form of the resulting mixture depends upon a number of factors, including the intended mode of administration and the solubility of the digestive enzymes in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving digestive enzymes as provided herein in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the digestive enzymes. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected digestive enzymes. Such amount can be empirically determined.

4. Topical Administration

Topical mixtures can be prepared as described for local and systemic administration. The resulting mixture may be a solution, suspension, emulsions or the like and are formulated as creams, gels, ointments, emulsions, powders, solutions, elixirs, lotions, suspensions, tinctures, pastes, foams, aerosols, irrigations, sprays, suppositories, bandages, dermal patches or any other formulations suitable for topical administration.

The digestive enzymes may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in one embodiment, have diameters of less than 50 microns, in one embodiment less than 10 microns.

The digestive enzymes may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the digestive enzymes alone or in combination with other pharmaceutically acceptable excipients can also be administered.

These solutions, particularly those intended for ophthalmic use, may be formulated as 0.01%-10% isotonic solutions, pH about 5-7, with appropriate salts.

Powders can be formed with the aid of any suitable powder base, e.g., talc, lactose, starch, and the like. Solutions can be formulated with an aqueous or non-aqueous base, and can also include one or more dispersing agents, suspending agents, solubilizing agents, and the like. Topical gels are prepared using polymers having a molecular weight and level of concentration effective to form a viscous solution or colloidal gel of an aqueous or non-aqueous solution or suspension of digestive enzymes. Polymers from which topical gels may be prepared include polyphosphoesters, polyethylene glycols, high molecular weight poly (lactic) acids, hydroxypropyl celluloses, chitosan, polystyrene sulfonates, and the like.

Ointments, creams and lotions are formulated, for example, with an aqueous or oily base and addition of a suitable thickening agent, gelling agent, stabilizing agent, emulsifying agent, dispersing agent, suspending agent, or consistency regulating agent, and the like. Bases include water, an alcohol or an oil, such as liquid paraffin, mineral oil, or a vegetable oil, such as peanut or castor oil. Thickening agents that can be used according to the nature of the base include soft paraffin, aluminum stearate, cetostearyl alcohol, propylene glycol, polyethylene glycols, polyphosphoesters, poly(lactic acids), hydroxyethyl celluloses, hydroxypropyl celluloses, cellulose gums, acrylate polymers, hydrophilic gelling agents, chitosan, polystyrene sulfonate, petrolatum, woolfat, hydrogenated lanolin, beeswax, and the like.

The ointments, pastes, creams, gels, and lotions can also contain excipients, such as animal and vegetable fats, oils, waxes, paraffins, starch, tragacanth, cellulose derivatives, polyethylene glycols, silicones, bentonites, silicic acid, talc, zinc oxide, and mixtures thereof. Powders and sprays can also contain excipients such as silicic acid, aluminum hydroxide, calcium silicates and polyamide powder, or mixtures of these substances. Solutions, suspensions or dispersions can be converted into aerosols or sprays by any of the known means routinely used for making aerosols for topical application. In general, such methods comprise pressurizing or providing a means of pressurizing a container of a solution, suspension or dispersion, usually with an inert carrier gas, and passing the pressured gas through a small orifice. Sprays and aerosols can also contain customary propellants, e.g., chlorofluorohydrocarbons or volatile unsubstituted hydrocarbons, such as butane and propane.

Excipients include compounds that promote skin absorption, such as dimethyl sulfoxide (DMSO), partial glycerides of fatty acids, and the like, present at levels up to about 10 wt % of the total formula weight. Examples of partial fatty acid glycerides include, but are not limited to IMWITOR 742 and IMWITOR 308 available from SASOL North America, Inc. of Houston, Tex. The topical formulations may also optionally include inactive ingredients to improve cosmetic acceptability, including but not limited to, humectants, surfactants, fragrances, coloring agents, emollients, fillers, and the like.

The topical compositions may also include other antibiotic agents, examples of which include bacitracin, neomycin, polymixin, beta-lactams, including penicillin, methicillin, moxalactam and cephalosporins, such as cefaclor, cefadroxil, cefamandole nafate, cefazolin, cefixime, cefmetazole, cefonioid, cefoperazone, ceforanide, cefotanme, cefotaxime, cefotetan, cefoxitin, cefpodoxime proxetil, ceftazidime, ceftizoxime, ceftriaxone, cefriaxone, cefuroxime, cephalexin, cephalosporin C, cepahlosporin C sodium salt, cephalothin, cephalothin sodium salt, cephalothin dihydrate, cephapirin, cephradine, cefuroximeaxetil, loracarbef, and the like. Essentially any anti-infective/antibiotic agent that is effective when applied topically can be used. Thus, the methods of the present invention for both treating active infections and decolonizing skin pathogen populations include methods in which digestive enzymes are applied singularly or in combination, either with no other anti-infective agent, or with at least one other anti-infective agent.

The topical compositions can be administered directly by the dusting of a powder, spraying of an aerosol or by spreading a film of an ointment, cream, lotion, solution or gel to the desired area of the skin using the fingertips of the patient or a healthcare provider or other conventional application such as a swab or wipe. The product may be first applied to the skin and spread with the fingertips or an applicator or applied to the fingertips and spread over the skin. The compositions may also optionally first be coated on the surface of a topical applicator, such as a bandage, swab, moist woven or non-woven wipe and the like, which is then applied to the portion of the skin to receive the composition.

The topical compositions of the present invention can be prepared with base formulations that are essentially conventional to one of ordinary skill in the art with respect to the ingredients employed, quantities thereof, and methods of preparation, all of which require no further description. Topical compositions according to the present invention can also be prepared as a cream or lotion based on an emulsion formulation possessing heretofore unrecognized bactericidal activity, in addition to good skin compatibility and wound-healing properties that is particularly well-suited for formulation with digestive enzymes.

As discussed above, the present invention is not limited to topical cream or lotion formulations. Topical formulations based on conventional sprays, mists, aerosols, lotions, creams, aqueous and non-aqueous solutions or liquids, oils, gels, ointments, pastes, unguents, emulsions and suspensions will contain an amount of digestive enzymes, and optionally one or more other anti-infective agents, in a total concentration of between about 0.125 and about 10% by weight or more, recognizing again that optimal dosages may differ only by 0.05% by weight, so that representative cream and lotion embodiments will include every 0.05% by weight concentration increment within this range.

The topical compositions of the present invention are used to treat skin infections and wound infections such as surface wounds and penetrating wounds. Wounds suitable for treatment include wounds in skin abrasions, skin or surface cuts, decubiti, burns and surgical wounds. The topical compositions of the present invention can be used as well to decolonize populations of *E. coli* bacteria to prevent secondary, including the pre-treatment of areas prior to surgery or catheter insertion.

Mucosal delivery formulations can include digestive enzymes as described herein combined or coordinately administered with a suitable carrier or vehicle for mucosal delivery. As used herein, the term "carrier" means a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting agents or other biocompatible materials. A tabulation of ingredients listed by the above categories, can be found in the U.S. Pharmacopeia National Formulary, pp. 1857-1859, 1990. Some examples of the materials which can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen free water; isotonic saline; Ringer's solution, ethyl alcohol and phosphate buffer solutions, as well as other non toxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents, preservatives and antioxidants can also be present in the compositions, according to the desires of the formulator. Examples of pharmaceutically acceptable antioxidants include water soluble antioxidants such as ascorbic acid, cysteine hydrochloride, sodium bisulfate, sodium metabisulfite, sodium sulfite and the like; oil-soluble antioxidants such as ascorbyl palmitate, butylated hydroxyanisole (BHA), butylated hydroxytoluene (BHT), lecithin, propyl gallate, alpha-tocopherol and the like; and metal-chelating agents such as citric acid, ethylenediamine tetraacetic acid (EDTA), sorbitol, tartaric acid, phosphoric acid and the like. The amount of digestive enzymes that can be combined with the carrier materials to produce a single dosage form will vary depending upon the particular mode of administration.

Mucosal formulations are generally sterile, particulate free and stable for pharmaceutical use. As used herein, the term "particulate free" means a formulation that meets the requirements of the USP specification for small volume parenteral solutions. The term "stable" means a formulation that fulfills all chemical and physical specifications with respect to identity, strength, quality, and purity that have been established according to the principles of Good Manufacturing Practice, as set forth by appropriate governmental regulatory bodies.

Within the mucosal delivery compositions, various delivery-enhancing agents can be employed which enhance delivery of digestive enzymes into or across a mucosal surface. As used herein, "mucosal delivery-enhancing agents" include agents which enhance the release or solubility (e.g., from a formulation delivery vehicle), diffusion rate, penetration capacity and timing, uptake, residence time, stability, effective half-life, peak or sustained concentration levels, clearance and other desired mucosal delivery characteristics (e.g., as measured at the site of delivery, or at a selected target site of activity such as the bloodstream or central nervous system) of digestive enzymes or other biologically active compound(s). Enhancement of mucosal delivery can thus occur by any of a variety of mechanisms, for example by increasing the diffusion, transport, persistence or stability of the digestive enzymes, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, and other mechanisms.

While the mechanism of absorption promotion may vary with different intranasal delivery-enhancing agents of the invention, useful reagents in this context will not substantially adversely affect the mucosal tissue and will be selected according to the physicochemical characteristics of the particular digestive enzymes or other active or delivery-enhancing agent. In this context, delivery-enhancing agents that increase penetration or permeability of mucosal tissues will often result in some alteration of the protective permeability barrier of the mucosa. For such delivery-enhancing agents to be of value within the invention, it is generally desired that any significant changes in permeability of the mucosa be reversible within a time frame appropriate to the desired duration of drug delivery. Furthermore, there should be no substantial, cumulative toxicity, nor any permanent deleterious changes induced in the barrier properties of the mucosa with long-term use.

In some embodiments, absorption-promoting agents for coordinate administration or combinatorial formulation with the digestive enzymes as described herein are selected from small hydrophilic molecules, including but not limited to, dimethyl sulfoxide (DMSO), dimethylformamide, ethanol, propylene glycol, and the 2-pyrrolidones. Alternatively, long-chain amphipathic molecules, for example, deacylmethyl sulfoxide, azone, sodium lauryl sulfate, oleic acid, and the bile salts, may be employed to enhance mucosal penetration of the digestive enzymes. In additional aspects, surfactants (e.g., polysorbates) are employed as adjunct compounds, processing agents, or formulation additives to enhance intranasal delivery of the digestive enzymes. These penetration-enhancing agents typically interact at either the polar head groups or the hydrophilic tail regions of molecules that comprise the lipid bilayer of epithelial cells lining the nasal mucosa (Barry, Pharmacology of the Skin, Vol. 1, pp. 121-137, Shroot et al., Eds., Karger, Basel, 1987; and Barry, J. controlled Release 6:85-97, 1987). Interaction at these sites may have the effect of disrupting the packing of the lipid molecules, increasing the fluidity of the bilayer, and facilitating transport of the digestive enzymes across the mucosal barrier. Interaction of these penetration enhancers with the polar head groups may also cause or permit the hydrophilic regions of adjacent bilayers to take up more water and move apart, thus opening the paracellular pathway to transport of the digestive enzymes. In addition to these effects, certain enhancers may have direct effects on the bulk properties of the aqueous regions of the nasal mucosa. Agents such as DMSO, polyethylene glycol, and ethanol can, if present in sufficiently high concentrations in delivery environment (e.g., by pre-administration or incorporation in a therapeutic formulation), enter the aqueous phase of the mucosa and alter its solubilizing properties, thereby enhancing the partitioning of the digestive enzymes from the vehicle into the mucosa.

Additional mucosal delivery-enhancing agents that are useful within the coordinate administration and processing methods and combinatorial formulations of the invention include, but are not limited to, mixed micelles; enamines; nitric oxide donors (e.g., S-nitroso-N-acetyl-DL-penicillamine, NOR1, NOR4, which are preferably co-administered with an NO scavenger such as carboxy-PITO or doclofenac sodium); sodium salicylate; glycerol esters of acetoacetic acid (e.g., glyceryl-1, 3-diacetoacetate or 1,2-isopropylideneglycerine-3-acetoacetate); and other release-diffusion or intra- or trans-epithelial penetration-promoting agents that are physiologically compatible for mucosal delivery. Other absorption-promoting agents are selected from a variety of carriers, bases and excipients that enhance mucosal delivery, stability, activity or trans-epithelial penetration of the digestive enzymes. These include, inter alia, cyclodextrins and β-cyclodextrin derivatives (e.g., 2-hydroxypropyl-β-cyclodextrin and heptakis(2,6-di-O-methyl-β-cyclodextrin). These compounds, optionally conjugated with one or more of the active ingredients and further optionally formulated in an oleaginous base, enhance bioavailability in the mucosal formulations of the invention. Yet additional absorption-enhancing agents adapted for mucosal delivery include medium-chain fatty acids, including mono- and diglycerides (e.g., sodium caprate-extracts of coconut oil, Capmul), and triglycerides (e.g., amylodextrin, Estaram 299, Miglyol 810).

The mucosal therapeutic and prophylactic compositions may be supplemented with any suitable penetration-promoting agent that facilitates absorption, diffusion, or penetration of digestive enzymes across mucosal barriers. The penetration promoter may be any promoter that is pharmaceutically acceptable. Thus, in more detailed aspects of the invention compositions are provided that incorporate one or more penetration-promoting agents selected from sodium salicylate and salicylic acid derivatives (e.g., acetyl salicylate, choline salicylate, salicylamide); amino acids and salts thereof (e.g. monoaminocarboxlic acids such as glycine, alanine, phenylalanine, proline, hydroxyproline; hydroxyamino acids such as serine; acidic amino acids such as aspartic acid, glutamic acid; and basic amino acids such as lysine—inclusive of their alkali metal or alkaline earth metal salts); and N-acetylamino acids (N-acetylalanine, N-acetylphenylalanine, N-acetylserine, N-acetylglycine, N-acetyllysine, N-acetylglutamic acid, N-acetylproline, N-acetylhydroxyproline, etc.) and their salts (alkali metal salts and alkaline earth metal salts). Also provided as penetration-promoting agents within the methods and compositions of the invention are substances which are generally used as emulsifiers (e.g. sodium oleyl phosphate, sodium lauryl phosphate, sodium lauryl sulfate, sodium myristyl sulfate, polyoxyethylene alkyl ethers, polyoxyethylene alkyl esters, etc.), caproic acid, lactic acid, malic acid and citric acid and alkali metal salts thereof, pyrrolidoncecarboxylic acids, alkylpyrrolidonecarboxylic acid esters, N-alkylpyrrolidones, proline acyl esters, and the like.

5. Compositions for Other Routes of Administration

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

6. Sustained Release Formulations

Also provided are sustained release formulations to deliver the digestive enzymes to the desired target. It is understood that the digestive enzymes levels are maintained over a certain period of time as is desired and can be easily determined by one skilled in the art. Such sustained and/or timed release formulations may be made by sustained release means of delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556 and 5,733,566, the disclosures of which are each incorporated herein by reference. These pharmaceutical compositions can be used to provide slow or sustained release of one or more digestive enzymes using, for example, hydroxypropylmethyl cellulose, other polymer matrices, gels, permeable membranes, osmotic systems, multilayer coatings, microparticles, liposomes, microspheres, or the like. Suitable sustained release formulations known to those skilled in the art, including those described herein, may be readily selected for use with the pharmaceutical compositions provided herein. Thus, single unit dosage forms suitable for oral administration, such as, but not limited to, tablets, capsules, gelcaps, caplets, powders and the like, that are adapted for sustained release are contemplated herein.

In one embodiment, the sustained release formulation contains an active compound such as, but not limited to, microcrystalline cellulose, maltodextrin, ethylcellulose, and magnesium stearate. As described above, all known methods for encapsulation which are compatible with properties of the disclosed digestive enzymes are contemplated herein. The sustained release formulation is encapsulated by coating particles or granules of the pharmaceutical compositions provided herein with varying thickness of slowly soluble polymers or by microencapsulation. In one embodiment, the sustained release formulation is encapsulated with a coating material of varying thickness (e.g. about 1 micron to 200 microns) that allow the dissolution of the pharmaceutical composition about 48 hours to about 72 hours after administration to a mammal. In another embodiment, the coating material is a food-approved additive.

In another embodiment, the sustained release formulation is a matrix dissolution device that is prepared by compressing the drug with a slowly soluble polymer carrier into a tablet. In one embodiment, the coated particles have a size range between about 0.1 to about 300 microns, as disclosed in U.S. Pat. Nos. 4,710,384 and 5,354,556, which are incorporated herein by reference in their entireties. Each of the particles is in the form of a micromatrix, with the active ingredient uniformly distributed throughout the polymer.

The digestive enzymes provided herein can be formulated as a sustained and/or timed release formulation. All sustained release pharmaceutical products have a common goal of improving drug therapy over that achieved by their non-sustained counterparts. Ideally, the use of an optimally designed sustained release preparation in medical treatment is characterized by a minimum of digestive enzymes being employed to cure or control the condition. Advantages of sustained release formulations may include: 1) extended activity of the composition, 2) reduced dosage frequency, and 3) increased patient compliance. In addition, sustained release formulations can be used to affect the time of onset of action or other characteristics, such as blood levels of the composition, and thus can affect the occurrence of side effects.

The sustained release formulations provided herein are designed to initially release an amount of the therapeutic composition that promptly produces the desired therapeutic effect, and gradually and continually release of other amounts of compositions to maintain this level of therapeutic effect over an extended period of time. In order to maintain this constant level in the body, the therapeutic composition must be released from the dosage form at a rate that will replace the composition being metabolized and excreted from the body.

The sustained release of an active ingredient may be stimulated by various inducers, for example pH, temperature, enzymes, water, or other physiological conditions or compounds.

Preparations for oral administration may be suitably formulated to give controlled release of the digestive enzymes. In one embodiment, the digestive enzymes are formulated as controlled release powders of discrete microparticles that can be readily formulated in liquid form. The sustained release powder comprises particles containing an active ingredient and optionally, an excipient with at least one non-toxic polymer.

The powder can be dispersed or suspended in a liquid vehicle and will maintain its sustained release characteristics for a useful period of time. These dispersions or suspensions have both chemical stability and stability in terms of dissolution rate. The powder may contain an excipient comprising a polymer, which may be soluble, insoluble, permeable, impermeable, or biodegradable. The polymers may be polymers or copolymers. The polymer may be a natural or synthetic polymer. Natural polymers include polypeptides (e.g., zein), polysaccharides (e.g., cellulose), and alginic acid. Representative synthetic polymers include those described, but not limited to, those described in column 3, lines 33-45 of U.S. Pat. No. 5,354,556, which is incorporated by reference in its entirety. Particularly suitable polymers include those described, but not limited to those described in column 3, line 46-column 4, line 8 of U.S. Pat. No. 5,354,556 which is incorporated by reference in its entirety.

The sustained release compositions provided herein may be formulated for parenteral administration, e.g., by intramuscular injections or implants for subcutaneous tissues and various body cavities and transdermal devices. In one embodiment, intramuscular injections are formulated as aqueous or oil suspensions. In an aqueous suspension, the sustained release effect is due to, in part, a reduction in solubility of the digestive enzymes upon complexation or a decrease in dissolution rate. A similar approach is taken with oil suspensions and solutions, wherein the release rate of digestive enzymes is determined by partitioning of the digestive enzymes out of the oil into the surrounding aqueous medium. Only digestive enzymes which are oil soluble and have the desired partition characteristics are suitable. Oils that may be used for intramuscular injection include, but are not limited to, sesame, olive, *arachis*, maize, almond, soybean, cottonseed and castor oil.

Coadministration with Other Pharmaceutical Compositions

The pharmaceutical compositions can be used on their own, and/or in combination with other therapeutic or antibiotic (e.g., anti-*E. coli*) regimens. For example, a patient can be administered other therapeutic agents, such as anti-inflammatories or anesthetics, to address other aspects of an *E. coli* infection (e.g., pain, tissue damage) or still other illnesses that the patient may be facing. In other embodiments, a patient can be administered a pharmaceutical composition as described herein, and one or more additional antibiotics. The one or more additional antibiotics can be effective against *E. coli* or other bacteria, or both (e.g., if the patient has multiple infections) and can be in the same or a different format from the present pharmaceutical compositions (e.g., one can be a liquid and one can be a topical antibiotic). The major classes of antibiotics are (1) the β-lactams, including the penicillins, cephalosporins and monobactams; (2) the aminoglycosides, e.g., gentamicin, tobramycin, netilmycin, and amikacin; (3) the tetracyclines; (4) the sulfonamides and trimethoprim; (5) the fluoroquinolones, e.g., ciprofloxacin, norfloxacin, and ofloxacin; (6) vancomycin; (7) the macrolides, which include for example, erythromycin, azithromycin, and clarithromycin; and (8) other antibiotics, e.g., the polymyxins, chloramphenicol and the lincosamides.

In some embodiments, the additional antibiotic can be a beta-lactam antibiotic (e.g., a penicillin or penicillin derivatives, a cephalosporin, a monobactam, a penam, a penem, an oxapenam, a carbapenem or a cabapenam, a cephem, a carbacephem, an oxacephem, a monobactam). In some embodiments, the additional antibiotic can be a beta-lactamase inhibitor. In some embodiments, the additional antibiotic can be an aminoglycosidic antibiotic. In some embodiments, the additional antibiotic is selected from penicillin or a penicillin derivative, oxacillin, amoxicillin, nafcillin, cloxacillin, methicillin, temocillin, ampicillin, co-amoxiclav, azlocillin, carbenicillin, ticarcillin, mezlocillin, piperacillin, cephalexin, cephalothin, cefazolin, cefaclor, cefuroxime, cefamandole, cefotetan, cefoxitin, ceftriaxone, cefotaxime, cefpodoxime, ceftazidime, cefepime, cefpirome, vancomycin, teicoplanin, telavancin, bleomycin, ramoplanin, decaplanin, oritavancin, and dalbavancin.

An antibiotic composition described herein and an additional antibiotic can be administered separately or in a single dosage form. If separately, they can be administered in any order and relative frequency.

Disinfectants and Sanitizers

Compositions comprising one or more digestive enzymes as described herein can also be used as disinfectants and sanitizers, e.g., to disinfect inanimate objects and surfaces in, without limitation, hospital, health care, home, and community settings by eradicating, attenuating or reducing E. coli in such locations. Disinfectants are antimicrobial agents that are applied to non-living objects to destroy microorganisms. Disinfectants should generally be distinguished from antibiotics that destroy microorganisms within the body, and from antiseptics, which destroy microorganisms on living tissue. Sanitizers are disinfectants that reduce the number of microorganisms to a safe level. One definition of a sanitizer states that a sanitizer must be capable of killing 99.999%, known as a 5 log reduction, of a specific bacterial test population, and to do so within 30 seconds. The main difference between a sanitizer and a disinfectant is that at a specified use dilution, the disinfectant must have a higher kill capability for pathogenic bacteria compared to that of a sanitizer.

A disinfectant or sanitizer as described herein can include one or more digestive enzymes, in various embodiments as described previously above, and can optionally include other active and inactive ingredients, including stabilizers (e.g., enzyme stabilizers), other disinfectants known to those having ordinary skill in the art, formulation excipients, colorants, perfumes, etc. One having ordinary skill in the art can select the additional active or inactive ingredients to include in a disinfectant. Examples of additional disinfectants include: sources of active chlorine (i.e., hypochlorites, chloramines, dichloroisocyanurate and trichloroisocyanurate, wet chlorine, chlorine dioxide etc.); sources of active oxygen (peroxides, such as peracetic acid, potassium persulfate, sodium perborate, sodium percarbonate and urea perhydrate); iodine and iodophor solutions (iodpovidone (povidone-iodine, Betadine), Lugol's solution, iodine tincture, iodinated nonionic surfactants); concentrated alcohols (mainly ethanol, 1-propanol, called also n-propanol and 2-propanol, called isopropanol and mixtures thereof; further, 2-phenoxyethanol and 1- and 2-phenoxypropanols); phenolic substances (such as phenol (also called "carbolic acid"), cresols (called "Lysole" in combination with liquid potassium soaps), halogenated (chlorinated, brominated) phenols, such as hexachlorophene, triclosan, trichlorophenol, tribromophenol, pentachlorophenol, Dibromol and salts thereof); cationic surfactants, such as some quaternary ammonium cations (such as benzalkonium chloride, cetyl trimethylammonium bromide or chloride, didecyldimethylammonium chloride, cetylpyridinium chloride, benzethonium chloride) and others; non-quarternary compounds, such as chlorhexidine, glucoprotamine, octenidine dihydrochloride; strong oxidizers, such as ozone and permanganate solutions; heavy metals and their salts, such as colloidal silver, silver nitrate, mercury chloride, phenylmercury salts, copper sulfate, and copper oxide-chloride; concentrated strong acids (phosphoric, nitric, sulfuric, amidosulfuric, toluenesulfonic acids) and alkalis (sodium, potassium, calcium hydroxides), such as of pH<1 or >13, particularly under elevated temperature (above 60° C.). In some cases, a disinfectant as described herein will consist essentially of the one or more digestive enzymes. In some cases, a disinfectant will consist essentially of the one or more digestive enzymes, and will not include additional disinfecting agents.

A disinfectant composition comprising one or more digestive enzymes as described herein can be incorporated with other ingredients to form a variety of disinfectant products including but not limited to hand cleansers, mouthwashes, surgical scrubs, body splashes, hand sanitizer gels and foams, disinfectant wipes, and similar personal care products. Additional types of products include disinfectant foams, creams, mousses, and the like, and compositions containing organic and inorganic filler materials, such as emulsions, lotions, creams, pastes, and the like. The compositions can also be used as an antibacterial cleanser for hard surfaces, for example, sinks and countertops in hospitals, food service areas, and meat processing plants. The disinfectant compositions can also be used as disinfectant fogs and disinfectant mists. The present digestive enzyme compositions can be manufactured as dilute ready-to-use compositions, or as concentrates that are diluted prior to use. The various products in which the disinfectants are used may also include fragrances, depending on the nature of the product. For example, a pine or lemon fragrance may be desirable for use for kitchen cleaning wipes because of their appealing association with cleanliness to many consumers. Further, gels or aerosols may also be fragranced for similar or other reasons.

In one embodiment, the disinfectant compositions can be used to make disinfectant wipes. A disinfectant wipe can be used to clean a variety of hard and other surfaces, including, for example, human hands and skin, medical instruments and devices, countertops, floors, walls, and windows. Wipes can be made of a variety of fabrics. Fabrics are defined to include cloths and papers, as well as woven and non-woven materials. The woven or nonwoven fabrics can be made of suitable materials such as rayon, nylon, or cotton, and combinations thereof. Examples of nonwoven fabrics are described in U.S. Pat. Nos. 3,786,615; 4,395,454; and 4,199,322; which are hereby incorporated by reference. The fabrics or papers can be impregnated with the disinfectant solution by any method known in the art. The wipes can be packaged in any manner known in the art including individual blister-packs or wrapped or stacked multi-packs.

In another embodiment, the disinfectant composition comprising one or more digestive enzymes can be formulated into a gel or gelatinous sanitization composition. In addition to the disinfectant compositions, the gel sanitizers can include a thickening or gelling agent, wherein "thickening agent" and "gelling agent" are used interchangeably. As used herein, the terms "gel" or "gelatinous" sanitization compositions refers to a disinfectant liquid substances that can have a viscosity from about 1,000 centipoise to about 100,000 centipoise, or from 2,000 centipoise to 50,000 centipoise in another embodiment, though these ranges are not intended to be limiting. For example, a hand gel may be considerably less viscous than a gel used for industrial cleaning or disinfectant purposes. Examples of gelling or thickening agents include but are not limited to natural gum such as guar and guar derivatives, a synthetic polymer, a clay, an oil, a wax, aloe vera gel, an acrylate homopolymer, an acrylate copolymer, a carbomer, cellulose, a cellulose derivative, algin, an algin derivative, a water-insoluble C8-C20 alcohol, carrageenan, fumed silica, mixtures thereof, and the like. The gelling agent can be present in the gelatinous sanitation composition in an amount from about 0.1 wt % to 50 wt % of the gelatinous composition. In another embodiment, the gelling agent is present in an amount from 0.25 wt % to 10 wt % of the gelatinous composition. The amount of gelling agent can be dependent on a variety of factors including the type of gelling agent and the desired viscosity of the gel. The gelatinous sanitizers can be used for a variety of applications including sanitization of human skin e.g., gel hand sanitizer, and hard surface sanitation. In one particular embodiment, the disinfectant composition can be mixed with natural aloe gel to form a disinfectant aloe formulation. Such a formulation would be useful for application to burns, skin infections, and other irritations. The aloe may act as a thickening agent, or may also include another thickening or gelling agent as described above, depending on the desired viscosity of the disinfectant gel.

In another embodiment, a disinfectant composition comprising one or more digestive enzymes can be formulated into a disinfectant foam or foaming composition. The disinfectant foams or foaming compositions include the disinfectant composition and foaming agents. Any foaming agent known in the art can be used depending on the desired application and characteristics of the resulting disinfectant foam. As with the disinfectant composition, the disinfectant foams of the present invention can be used in both human (e.g. hand washing) and industrial applications.

In another embodiment, the disinfectant composition comprising one or more digestive enzymes can be in the form of a disinfectant aerosol or fog. Fogging, also referred to as thermal fogging, is the process by which disinfectants are aerosolized. The aerosol particles of the disinfectant are suspended within the air for a period of time in order to disinfect both the air itself and surfaces, including inaccessible parts of a structure such as air vents. The aerosolized particles of disinfectant can have a particle size of from about 5 µm to about 200 µm. In another embodiment, the aerosolized particle can have a particle size of from about 20 µm to about 150 µm.

Methods for evaluating the disinfectant ability of a particular composition are known to those having ordinary skill in the art. Typically, the relative effectiveness of a disinfectant can be measured by comparing how well it disinfects as compared to a known disinfectant. Phenol is one known disinfectant standard, and the corresponding rating system is called the "Phenol coefficient". The disinfectant to be tested is compared with phenol on a standard microbe, e.g., E. coli or S. aureus. Disinfectants that are more effective than phenol have a coefficient >1. Those that are less effective have a coefficient <1. To calculate phenol coefficient, the concentration of the test compound at which the compound kills the test organism in 10 minutes, but not in 5 minutes, is divided by the concentration of phenol that kills the organism under the same conditions. The phenol coefficient may be determined in the presence of a standard amount of added organic matter or in the absence of organic matter. One particular phenol coefficient assay uses the Rideal-Walker method. The U.S. Department of Agriculture also has a method that gives a U.S. Department of Agriculture coefficient. Other methods are known to those having ordinary skill in the art.

A disinfectant as described herein can have a phenol coefficient for S. aureus that is >1, e.g., greater than 1.05, 1.1, 1.2, 1.3, 1.4, 1.5, 1.75, 2, 2.25, 2.5, 2.75, 3, 3.5, 4, 4.5, 5, 6, 7, 8, 9, 10, 12, 14, 16, 18, or higher. In some cases, the phenol coefficient is in the range from about 2 to about 20, e.g., about 4 to about 10, about 2 to about 6, about 6 to about 12, or about 10 to about 15.

A disinfectant as described herein can have a phenol coefficient for E. coli that is >1, e.g., greater than 1.05, 1.1, 1.2, 1.3, 1.4, 1.5, 1.75, 2, 2.25, 2.5, 2.75, 3, 3.5, 4, 4.5, 5, 6, 7, 8, 9, 10, 12, 14, 16, 18. In some cases, the phenol coefficient is in the range from about 2 to about 20, e.g., about 4 to about 10, about 2 to about 6, about 6 to about 12, or about 10 to about 15.

A disinfectant or sanitizer as described herein can be bacteriocidal and/or bacteriostatic to E. coli. In some embodiments, a disinfectant or sanitizer as described herein can be bacteriocidal and/or bacteriostatic against STEC, ETEC, or EPEC, or any 2, or all 3.

Detergents

A disinfectant composition comprising one or more digestive enzymes described herein can also be formulated as a detergent. A detergent is a material intended to assist cleaning. A detergent can contain one or more digestive enzymes, as described previously, in a formulation suitable to maintain its disinfectant ability, and can contain optional active or inactive ingredients, e.g., enzyme stabilizers, additional disinfectants, bleaches, soaps, surfactants, colorants and perfumes, abrasives, pH modifiers, acids, alkalis, or caustic compounds, water softeners, oxidants, suspending agents, fabric softeners, foaming agents or anti-foaming agents, viscosity modifiers, corrosion inhibitors, and optical brighteners. A detergent as described herein can be bacteriostatic and/or bacteriocidal to E. coli, and in some embodiments can be bacteriostatic and/or bacteriocidal against STEC, ETEC, or EPEC, or any 2, or all 3.

A detergent composition comprising one or more digestive enzymes, especially those made for use with water, can include additional components such as surfactants to 'cut' (dissolve) grease and to wet surfaces, abrasives to scour, substances to modify pH or to affect performance or stability, acids for descaling or caustics to break down organic compounds, water softeners to counteract the effect of "hardness" ions, oxidants (oxidizers) for bleaching, disinfection, and breaking down organic compounds, non-surfactant materials that keep dirt in suspension, enzymes to digest proteins, fats, or carbohydrates in stains or to modify fabric feel, ingredients that modify the foaming properties of the cleaning surfactants, to either stabilize or counteract foam, ingredients to increase or decrease the viscosity of the solution, or to keep other ingredients in solution, in a detergent supplied as a water solution or gel, ingredients that affect aesthetic properties of the item to be cleaned, or of the detergent itself before or during use, such as optical brighteners, fabric softeners, colors, and perfumes, ingredients such as corrosion inhibitors to counteract damage to equipment with which the detergent is used, ingredients to reduce harm or produce benefits to skin, when the detergent is used by bare hand on inanimate objects or used to clean skin, and preservatives to prevent spoilage of other ingredients.

The detergent composition may be in any convenient dry form, e.g., a bar, a tablet, a powder, a granule or a paste. It may also be a liquid detergent.

The digestive enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

Antiseptics

Various embodiments of compositions comprising on or more digestive enzymes can also be used as antiseptic agents, e.g., to reduce, eradicate, or attenuate E. coli on skin or other living tissues. Antiseptics are antimicrobial substances that are applied to living tissue/skin to reduce the possibility of infection, sepsis, or putrefaction. They should generally be distinguished from antibiotics that destroy bacteria within the body, and from disinfectants, which destroy microorganisms found on non-living objects. Some antiseptics are true germicides, capable of destroying microbes (bacteriocidal), while others are bacteriostatic and only prevent or inhibit their growth.

The presently described antiseptics can find particular use in hospital or healthcare settings, e.g., in hand, facial or body-wash formulations; as antiseptics for use prior to and post surgical treatment; and as antiseptics for use in cleansing and treating wounds, such as traumatic or surgical wounds. In the community setting, antiseptics are useful in any setting where community-acquired infections are of concern, e.g., daycare settings, large institutions, schools, etc. Antiseptics can also be useful in the home setting in hand, facial or body-wash formulations, or for treating wounds.

An antiseptic can include one or more digestive enzymes, in various embodiments as described previously, and can optionally include one or more active or inactive ingredients, such as other antiseptic agents known to those having ordinary skill in the art, stabilizers (e.g., enzyme stabilizers), colorants, perfumes, and other excipients. Examples of antiseptic agents to include with the one or more digestive enzymes include alcohols (e.g., ethanol, 1- and 2-propanol, or mixtures thereof), quaternary ammonium compounds (benzalkonium chloride, cetyl trimethylammonium bromide, cetylpyridinium chloride, and benzethonium chloride), boric acid, chlorhexidine gluconate, peroxides (e.g., hydrogen peroxide, benzoyl peroxide); iodine and iodophor solutions (e.g., povidone-iodine), octenidine dihydrochloride, Phenolic (carbolic acid) and phenolic derivative compounds, sodium chloride, sodium hypochlorite, and calcium hypochlorite.

An antiseptic as described herein can be bacteriocidal and/or bacteriostatic to *E. coli*, and in some embodiments can be bacteriocidal and/or bacteriostatic to STEC, ETEC, or EPEC, or any 2, or all 3.

In one embodiment, an antiseptic composition comprises one or more digestive enzymes and optionally one or more of an anti-inflammatory agent, an analgesic, or an anaesthetic.

An anti-inflammatory agents can include steroidal and non-steroidal anti-inflammatory compounds. In one embodiment, the antiseptic composition includes one or more steroids. In one embodiment, the antiseptic compositions can comprise an anti-inflammatory agent that is a non-steroidal anti-inflammatory drug. Non-limiting examples of suitable non-steroidal anti-inflammatory drugs include aspirin (Anacin, Ascriptin, Bayer, Bufferin, Ecotrin, Excedrin), choline and magnesium salicylates (CMT, Tricosal, Trilisate), choline salicylate (Artliropan), celecoxib (Celebrex), diclofenac potassium (Cataflam), diclofenac sodium (Voltaren, Voltaren XR), diclofenac sodium with misoprostol (Arthrotec), difiunisal (Dolobid), etodolac (Lodine, Lodine XL), fenoprofen calcium (Nalfon), flurbiprofen (Ansaid), ibuprofen (Advil, Motrin, Motrin IB, Nuprin), indomethacin (Indocin, Indocin SR), ketoprofen (Actron, Orudis, Orudis KT, Oruvail), magnesium salicylate (Arthritab, Bayer Select, Doan's Pills, Magan, Mobidin, Mobogesic), meclofenamate sodium (Meclomen), mefenamic acid (Ponstel), meloxicam (Mobic), nabumetone (Relafen), naproxen (Naprosyn, Naprelan), naproxen sodium (Aleve, Anaprox), oxaprozin (Daypro), piroxicam (Feldene), rofecoxib (Vioxx), salsalate (Amigesic, Anaflex 750, Disalcid, Marthritic, Mono-Gesic, Salflex, Salsitab), sodium salicylate, sulindac (Clinoril), tolmetin sodium (Tolectin), valdecoxib (Bextra), or a combination thereof.

Non-limiting examples of analgesics include acetylsalicylic acid, codeine, ibuprofen, acetaminophen, or tea tree oil. Non-limiting examples of anaesthetics include xylocaine, prilocaine or benzocaine.

Exemplary methods of testing candidate antiseptic compositions are provided below. One skilled in the art will understand that other methods of testing the antiseptic compositions are known in the art and are also suitable for testing candidate antiseptic compositions.

In vitro methods of determining the ability of candidate antiseptic compositions to kill or inhibit the growth of microbial cells such as *E. coli* are well-known in the art. In general, these methods involve contacting a culture of the cells of interest with various concentrations of the candidate antiseptic compositions and monitoring the growth of the cell culture relative to an untreated control culture. A second control culture comprising cells contacted with a known anti-microbial agent may also be included in such tests, if desired.

For example, the ability of a candidate antiseptic composition to inhibit the growth of microbial cells can readily be determined by measurement of the minimum inhibitory concentration (MIC) for the antiseptic composition. The MIC is defined as the lowest concentration that inhibits growth of the organism to a pre-determined extent. For example, a $MIC_{100}$ value is defined as the lowest concentration that completely inhibits growth of the organism, whereas a $MIC_{90}$ value is defined as the lowest concentration that inhibits growth by 90% and a $MIC_{50}$ value is defined as the lowest concentration that inhibits growth by 50%. MIC values are sometimes expressed as ranges, for example, the $MIC_{100}$ for an antiseptic composition may be expressed as the concentration at which no growth is observed or as a range between the concentration at which no growth is observed and the concentration of the dilution which immediately follows.

Anti-bacterial MICs for candidate antiseptic compositions can be measured using a broth macro- or microdilution assay (see Amsterdam, D. (1996) "Susceptibility testing of antimicrobials in liquid media," pp. 52-111. In Loman, V., ed. Antibiotics in Laboratory Medicine, 4th ed. Williams and Wilkins, Baltimore, Md.). A standardised anti-bacterial susceptibility test is provided by the National Committee for Clinical Laboratory Standards (NCCLS) as NCCLS, 2000; document M7-A58.

In the classical broth microdilution method, the candidate antiseptic composition is diluted in culture medium in a sterile, covered 96-well microtiter plate. An overnight culture of a single bacterial colony is diluted in sterile medium such that, after inoculation, each well in the microtiter plate contains an appropriate number of colony forming units (CFU)AnI (typically, approximately 5×105 CFU/ml). Culture medium only (containing no bacteria) is also included as a negative control for each plate and known antibiotics are often included as positive controls. The inoculated microtiter plate is subsequently incubated at an appropriate temperature (for example, 35° C.-37° C. for 16-48 hours). The turbidity of each well is then determined by visual inspection and/or by measuring the absorbance, or optical density (OD), at 595 nm or 600 nm using a microplate reader and is used as an indication of the extent of bacterial growth.

Anti-microbial effects may also be expressed as the percentage (%) inhibition of growth of a given microorganism over a pre-determined period of time by treatment with a single concentration of a candidate antiseptic composition. This method provides a rapid method of assessing the ability of an antiseptic composition to inhibit microbial growth, for example, prior to conducting more in-depth tests, such as MIC determinations or in vivo testing.

The ability of any of the present disinfectant, detergent, santitizer, and antiseptic compositions to kill or inhibit the growth of E. coli bacteria can be tested using methods well-known in the art, including the various methods described above. Methods and protocols for testing compositions against specific bacteria can be found, for example, in Official Methods of Analysis of the AOAC, 15th Ed., Arlington Va. 22201, USA (Association of Official Analytical Chemists (AOAC), Inc. 1990), Designation: E 1054-91 "Practices for Evaluation Inactivators of Antimicrobial Agents Used in Disinfectant, Sanitizer, Antiseptic, or Preserved Products" (American Society for Testing and Materials (ASTM), 1991). As is also known in the art, in vitro Time-Kill evaluations can be performed using a modification of the methods described in the Draft European Standard, prEN 12054, "Chemical Disinfectants and Antiseptics—Products for Hygienic and Surgical Handrub and Handwash—Bactericidal Activity—Test Method and Requirements (1995)." Additional methods that may be used include the log reduction test, proliferation testing, the AOAC use dilution test, or the zone of inhibition test. Other methods are described in the Examples below.

Kits

Also provided herein are kits. Typically, a kit includes one or more compositions as described herein. In certain embodiments, a kit can include one or more delivery or administration systems, e.g., for delivering or administering a composition as provided above, and/or directions for use of the kit (e.g., instructions for treating a patient; instructions for disinfecting a surface). In another embodiment, the kit can include a composition as described herein and a label, e.g., a label that indicates that the contents are to be administered to a patient with a E. coli infection, or a label as to how to use the composition as a disinfectant, sanitizer, detergent, or antiseptic.

Methods of Use

Pharmaceutical compositions (e.g., antibiotic compositions) described previously can be used to treat or prevent E. coli infections in animals, e.g., mammals and birds. In particular, the pharmaceutical compositions can be used to ameliorate one or more symptoms and side effects of such infections and/or to reduce or eradicate the E. coli bacterium causing the infection. The pharmaceutical compositions can be in any appropriate dosage form, as described previously. In certain embodiments, the antibiotic compositions described herein are used to treat wounds or lesions that have become infected, e.g., wounds resulting from trauma or surgery. Such use can reduce scarring and promote wound healing in patients having infected wounds. Compositions formulated for pharmaceutical use can also be employed prophylactically, e.g., as antiseptics. Such compositions find particular use in the prophylactic treatment of surgical incisions and other wounds, to prevent E. coli infection.

The digestive enzymes provided herein can be used to treat a variety of diseases and disorders associated with infection by E. coli bacteria or in which E. coli bacteria are implicated. Certain embodiments include infections associated with medical devices or prostheses, e.g. catheter, grafts, prosthetic heart valves, artificial joints, etc. In some embodiments, a composition comprising one or more digestive enzymes can be coated onto the medical device either at manufacture of the device or after manufacture but prior to insertion of the device.

Surgical wounds, especially those associated with foreign material, e.g. sutures may also be treated with the compositions provided herein. As many as 71% of all nosocomial infections occur in surgical patients, 40% of which are infections at the operative site. Despite efforts to prevent infection, it is estimated that between 500,000 and 920,000 surgical wound infections complicate the approximately 23 million surgical procedures performed annually in the United States.

The digestive enzymes alone or with an antibiotic, anesthetic, or anti-inflammatory may be applied as an ointment, cream or liquid to the wound site or as a liquid in the wound prior to and during closure of the wound. Following closure, a composition comprising one or more digestive enzymes could be applied at dressing changes. For wounds that are infected, the composition could be applied topically and/or systemically.

In early acute onset of osteomyelitis the vascular supply to the bone is compromised by infection extending into surrounding tissue. Within this necrotic and ischemic tissue, the bacteria may be difficult to eradicate even after an intense host response, surgery, and/or antibiotic therapy. The main organisms responsible are SA and E. coli.

The digestive enzymes could be administered systemically alone or in combination with other antibiotics. Treatment could be 2-6 weeks in duration. The antibiotic could be given as a continuous infusion or multiple administration during the day. A composition comprising one or more digestive enzymes could be used as an antibiotic-impregnated cement or as antibiotic coated beads for joint replacement procedures.

Treatment or prevention of sepsis in immunocompromised host is also provided. Treatment of infections in patients who are immunocompromised by virtue of chemotherapy-induced granulocytopenia and immunosuppression related to organ or bone marrow transplantation represents a significant challenge. The neutropenic patient is especially susceptible to bacterial infection, so antibiotic therapy should be initiated promptly to cover likely pathogens, if infection is suspected. Organisms likely to cause infections in granulocytopenic patients are: SA and E. coli.

The digestive enzyme composition alone or with an antibiotic is preferably administered orally or systemically for 2-6 weeks in duration. The digestive enzymes could be given as a continuous infusion or via multiple administrations during the day.

Disinfectant, sanitizing, and detergent compositions as described herein can be applied to non-living surfaces in the appropriate amounts and manner to reduce or eradicate E. coli on such surfaces, and thus can reduce or prevent E. coli transmission and/or infectivity. Concentrations, timing, and frequency of treatment are parameters that can be determined by one having ordinary skill in the art.

Any surface can be disinfected with the described compositions, including a variety of medical devices used in the hospital or health-care setting. As used herein, "medical device" refers to any device for use in or on a patient, such as an implant or prosthesis. Such devices include, without limitation, synthetic vascular grafts, blood monitoring devices, artificial heart valves, scalpel, knife, scissors, spatula, expander, clip, tweezer, speculum, retractor, suture, surgical mesh, chisel, drill, level, rasp, saw, splint, caliper, clamp, forceps, hook, lancet, needle, cannula, curette, depressor, dilator, elevator, articulator, extractor, probe, staple, valve, catheter, stent, tubing, bowl, tray, sponge, snare, spoon, syringe, pacemaker, screw, plate, or pin.

Other community and hospital or health-care surfaces suspected of harboring E. coli can be disinfected, including large or small surfaces (floors, tables, changing tables, beds, ventilation systems, tubs, door handles, counters, food service surfaces, etc.). The compositions can also find use in hand or body washes, e.g., at points of entry to community settings, hospital rooms, or bathrooms.

The compositions provided herein may be used in the manner of common disinfectants or in any situation in which microorganisms are undesirable. For example, they may be used as surface disinfectants, in coatings for medical devices, in coatings for clothing, such as to inhibit growth of bacteria or repel mosquitoes, in filters for air purification, such as on an airplane or in community or hospital settings, in water purification system, as constituents of shampoos and soaps, as food preservatives, cosmetic preservatives, media preservatives, in herbicides or insecticides, as constituents of building materials, such as in silicone sealant, and in animal product processing, such as the curing of animal hides or in slaughterhouses.

For these purposes, typically the digestive enzymes alone or in conjunction with other disinfectants or detergents are included in the compositions and applied with an appropriate applicator. They also may be incorporated or impregnated into the material during manufacture, such as for an air filter, or otherwise applied to the material or the object.

For example, in some embodiments, a composition described herein can be mixed in with the material, for example during manufacturing of the material or at a subsequent time. In addition, a composition can be applied to the surface of a material, either during manufacturing or at a subsequent time. As used herein, the term "suitable material" means any material on, to, or in which the digestive enzymes can be applied or incorporated, thereby incorporating an antimicrobial activity in/on the material. For example, a gauze pad on a bandage can be manufactured with a composition comprising one or more digestive enzymes in or on the gauze, and/or an ointment comprising one or more digestive enzymes can be applied to the gauze thereby incorporating antimicrobial activity to the gauze. Examples of suitable materials in which digestive enzymes may be used, include, but are not limited to: foods, liquids, a medical deivce (e.g. surgical instruments), a bead, a film, a monofilament, an unwoven fabric, sponge, cloth, a knitted fabric, a short fiber, a tube, a hollow fiber, an artificial organ, a catheter, a suture, a membrane, a bandage, and gauze. The digestive enzymes may be applied or mixed into numerous other types of materials that are suitable for use in medical, health, food safety, or environmental cleaning activities.

Veterinary Applications

The compositions described herein, in pharmaceutical or disinfectant/sanitizer, detergent or antiseptic formats, can also be used in a variety of veterinary applications. For example, many mammals, including dogs, cats, and cows, can be infected with *E. coli* or act as carriers of the bacteria. Accordingly, the present compositions can be used to treat animals infected with or suspected to carry *E. coli* in order to treat the infection or to prevent transmission to other animals, including humans. Disinfectant and detergent compositions can be used to treat animal living quarters and equipment that comes into contact with the animals, while antiseptics and antibiotic formulations can be used to treat animals to prevent or treat infection.

For example, the digestive enzymes provided herein can be used for the prevention and treatment of mastitis, particularly mastitis in dairy cattle, though any mastitis can be treated using the digestive enzymes provided herein. Mastitis in dairy cattle is an inflammation of the mammary gland in response to intramammary bacterial infection, mechanical trauma, or chemical trauma. It is thought that contagious mastitis is primarily caused by *S. aureus* and *Streptococcal agalactiae*. Environmental mastitis can be caused by a variety of different bacteria, including, but not limited to, *K. pneumoniae, E. coli, Klebsiella oxytoca, Enterobacter aerogenes, Streptococcal uberis, Streptococcal bovis*, and *Streptococcal dysgalactia*.

In some embodiments, prevention of bovine mastitis can include daily teat-dipping with a solution comprising one or more digestive enzymes. In some embodiments, the solution comprising one or more digestive enzymes may further include one or more additional antibiotics. When infection does occur, intramammary infusion of one or more digestive enzymes may be implemented. As above, additional antibiotics may also be administered in conjunction with the digestive enzymes. Typically, the digestive enzymes are administered by intramammary injection; however, effective dosages may be administered parenterally, percutaneously, by implant and also by dipping. In some embodiments, bovine mastitis can be treated by administering an effective amount of one or more digestive enzymes to a cow. The administration may be a prophylactic administration, in that all cattle in the herd are treated with a digestive enzyme composition, or the administration may occur when infection occurs in individual cows.

Introduction of *S. aureus* (also referred to as SA herein) bacteria and *E. coli* bacteria can occur during the preparation of beef, poultry, fish and pork products. Accordingly, in some embodiments, reduction of infection can be provided through administration of one or more digestive enzymes to an animal (e.g., cow, chicken, turkey, fish, or pig) to reduce the presence of *E. coli* or SA bacteria in the intestines of the animal. Administration may occur through any available method including injection and through the introduction of one or more digestive enzymes in feed.

In some embodiments, administration of one or more digestive enzymes to an animal may be used to prevent or reduce transmission of SA bacteria or *E. coli* from the animal to other animals or humans. Administration of the digestive enzymes may be accomplished through any available method known in the art.

Food Applications

Also provided herein is a method of preventing SA or *E. coli* infection of beef, poultry, fish, and pork. Beef processing is a common point of contamination: during the slaughtering process, the contents of intestines or fecal material on the hide could mix with the meat, thus allowing bacteria to flourish in the warm, damp conditions. If the infected parts are then ground, the bacteria go from the surface of the cut to the interior of the ground mass. Additionally, in the production of ground beef, meat from multiple cattle is often ground together, enabling contamination from a single animal to infect an entire lot of ground beef. Accordingly, in some embodiments, reduction of infection can be provided through administration of one or more digestive enzymes to a cow to reduce the presence of bacteria in the intestines of the cow. Administration may occur through any available method including injection and through the introduction of one or more digestive enzymes in feed. In another embodiment, the reduction of contamination of meat during slaughter and grinding can be provided through the use of sprays containing one or more digestive enzymes as provided herein. Such sprays may be used, for example, in the disinfection of slaughter and grinding instruments or in the disinfection of the ground meat itself. The methods described above can further be used during the slaughter and preparation of poultry, fish and pork products (e.g., through administration or one or more digestive enzymes to poultry, fish and/or pigs prior to slaughter).

E. coli and SA bacteria can also be spread through unwashed fruits and vegetables. Accordingly, also provided herein is a method of washing fresh fruits and vegetables using a solution, wash, aerosol, fog, gel, or powder comprising one or more digestive enzymes as provided herein. A produce wash is a solution used to bathe the surface of produce, and typically is in contact with the produce from about 30 sec to about 5 min. A produce soak is a solution in which produce items are immersed for a time from about 30 sec to about 30 min. However, the terms and solutions can be used interchangeably unless otherwise distinguished. It is understood that the temperature at which produce is washed or soaked will influence the length of time necessary to reduce or inactivate bacteria thereon, with warmer temperatures leading to a shorter time necessary for treatment.

The wash or soak solutions described herein can be used to reduce bacterial number, especially bacterial pathogen number, on the surfaces of fruits, vegetables, raw cut meat products, fish, shellfish, at the consumer level (in the household), in commercial food preparation environments, on fruits and/or vegetables prior to juicing, by wholesale or retail operators, and/or at the level of the harvest, meat packing plant or slaughterhouse, fishing boat, and so on, without limitation. The present methods are particularly useful for inactivating E. coli on the surfaces of fresh fruits and vegetables.

Methods for Evaluating Activity

Compositions described herein can be evaluated for a variety of activities by methods known to those having ordinary skill in the art. For example, enzymatic activities can be evaluated using standard enzyme assays. Minimum Inhibitory Concentrations (MIC) of the compositions can also be evaluated by methods known to those having ordinary skill in the art, as described above. Other assays, including the Phenol coefficient, are also well known to the skilled artisan. See also the Examples below.

EXAMPLES

Exemplary Liquid Compositions

A dry pancreatic enzyme composition containing about 200 USP units/mg of protease, about 40 USP units/mg of lipase, and about 250 USP units/mg of amylase can be diluted with various diluents (water, saline, phosphate buffered solutions, pH stabilized solutions) and optionally with other active or inactive additives (enzyme stabilization systems, buffers, colorants, sanitizers, detergents, disinfectants, antiseptics) to form exemplary liquid compositions for the uses described herein. In some embodiments, the dry enzyme composition can be diluted in a ratio of mgs of the dry enzyme composition to mls of the total diluent in the range from 1 mg enzyme composition:1 ml total diluent to 1 mg enzyme composition:10,000 mls total diluent, or any value in-between, e.g., 1:2, 1:3, 1:4, 1:5, 1:6, 1:7, 1:8, 1:9, 1:10, 1:20, 1:50, 1:100, 1:200, 1:500, 1:1000, 1:5000, or 1:10,000.

Exemplary Solid Compositions

A dry pancreatic enzyme composition containing about 200 USP units/mg of protease, about 40 USP units/mg of lipase, and about 250 USP units/mg of amylase can be mixed with various active or inactive dry ingredients and additives (e.g., dry detergents, disinfectants, antiseptics, and sanitizers, such as alkyl ethoxylate sulface, SDS, sodium laureth sulfate, dodecylbenzene, sodium 4-dodecylbenzene-sulfonate, enzyme stabilization systems, excipients, colorants) to form exemplary solid compositions. In some embodiments, the dry enzyme composition can be mixed with total mgs of the additives in the range from 1 mg enzyme composition:1 mg total additives to 1 mg enzyme composition:10,000 mgs total additives, or any value in-between, e.g., 1:2, 1:3, 1:4, 1:5, 1:6, 1:7, 1:8, 1:9, 1:10, 1:20, 1:50, 1:100, 1:200, 1:500, 1:1000, 1:5000, or 1:10,000.

Exemplary Topical Formulations

A dry pancreatic enzyme composition containing about 200 USP units/mg of protease, about 40 USP units/mg of lipase, and about 250 USP units/mg of amylase can be mixed with various carriers appropriate for topical pharmaceutical formulations in ratios ranging from about 1 mg of the enzyme composition to 1 mg of the carrier to about 1 mg of the enzyme composition to about 200 mg of the carrier, or any ratio therebetween (e.g., 1:2, 1:4, 1:5, 1:10, 1:20, 1:30, 1:40, 1:50, 1:75, 1:100, 1:150). For example, in one embodiment a 1:25 ratio is employed, and the carrier is petrolatum.

Bacterial Limit Testing—Evaluation of Bacteriocidal and Bacteriostatic Properties The present inventors have surprisingly found in the course of doing bacterial limit testing on a dry pig pancreatic enzyme composition comprising about 200 USP units/mg protease activity, about 40 USP units/mg of lipase activity, and 250 USP units/mg of amylase activity that E. coli bactera do not grow in the presence of various dilutions of this material. Recovery of E. coli CFUs from positive controls "spiked" with E. coli was consistently low to absent. Dilution bacterial limit testing of the dry composition in both unencapsulated and lipid-encapsulated (20% soy oil by weight of the composition) form demonstrate minimal to no recovery of the bacterium from positive controls to which a known number of CFUs of E. coli had been added. A lack of recovery during such recovery methods suggests a bacteriostatic and/or bacteriocidal nature of the composition.

Methods and Materials

Sample Materials—

Unencapsulated Porcine Pancreatic Enzyme Concentrate (uPEC) isolated from the pig (Sus scrofa) was manufactured by a commercial supplier (Scientific Protein Labs) to contain approximately 200 U/mg protease activity, 40 U lipase activity/mg, and 250 U of amylase activity/mg. A lipid encapsulated version of this material (ePEC) was obtained by using a modified fluidized bed process and a fully hydrogenated highly purified organic oil (fully hydrogenated soy oil) which was then used to coat the enzyme particles at a percentage by weight of about 20% of the final particles.

Methods:

Both the ePEC and uPEC underwent standard microbial analysis for the detection of microbes. Both compositions failed to show any significant contamination using Microbial Limits Testing per USP methods. Additionally, both samples were negative/10 g for Salmonella species and E. coli. Briefly, the procedure for the examination of test compositions for microbiological suitability (i.e., estimation of the total number of viable microorganisms and freedom from specific organism) is outlined in the USP, chapter 61, "Microbial Limit Tests." USP 61 outlines preparatory testing, during which is determined the test parameters wherein the test composition itself no longer inhibits the multiplication of viable organisms. USP 1227 ("Validation") also provides guidance to validate recovery methods. Methods for evaluating Total Aerobic Microbial Count, E. Coli, and Salmonella species were performed.

Total Aerobic Microbial Count:

Preparation of test dilutions—Bulk dilutions of ePEC and uPEC were prepared at 1:10, 1:50, 1;100 and 1:200 in Tryptic Soy broth containing 4% Polysorbate 20 and 0.5% lecithin. The bulk test sample dilution was then split into separate 10 ml aliquots, where were then inoculated with a low number of colony forming units (CFUs<100/mL) of the appropriate microorganisms (*S. aureus, P. aeruginosa, E. coli, S. enterica*). One millimeter of the inoculated aliquots was plated in duplicate using the appropriate solid medium (agar). Positive controls were prepared, inoculated, and plated in a manner similar to the test samples. Negative controls were prepared, inoculated with sterile reagent, and plated in a manner similar to the test samples. The plates were incubated at 30° C. to 35° C. for two days. At the end of the period the recovery was calculated. Recovery of inoculated organisms must be at least 70% of the positive control in order to show no inhibition of growth by the test composition. Triphenyltetrazolium chloride was used to count the plates.

Test for *Salmonella* Species—

Dilutions prepared with Lactose broth containing 4% polysorbate 20 and 0.5% lecithin were inoculated with <=100 CFU of *Salmonella enterica*. The inoculated dilutions were incubated at 30° C. to 35° C. for 24 hours prior to 1 ml being transferred to both Selenite Cystine and Tetrahionate broths. The selective broths were incubated for 18 hours at 30° C. to 35° C. prior to being streaked to brilliant green, bismuth sulfite an xylose lysine deoxycholate agars. The selective agar plates were incubated at 30° C. to 35° C. for 24 hours. The plates were observed for colonies characteristic of *Salmonella* species. Where observed, a representative colony was confirmed to be *Salmonella* species using an API 20e biochemical identification test.

Test for *E. coli*—

Dilutions prepared with Lactose broth containing 4% polysorbate 20 and 0.5% lecithin were inoculated with <=100 CFU of *E. coli*. The inoculated dilutions were incubated at 30° C. to 35° C. for 24 hours prior to being streaked to MacKonkey agar. The plates were observed for colonies characteristic of *E. coli*. Where observed, a representative colony was confirmed to be *E. coli* using an API 20e biochemical identification test.

Results

Total Aerobic Count: Test Results using the uncoated PEC (uPEC) are shown in Table 1, below. As shown, for dilutions of 1:50, 1:100, and 1:200 the percent recovery of *S. aureus* was 0%, demonstrating the bacteriocidal and/or bacteriostatic action of uPEC of *S. aureus*.

TABLE 1

Recovery of Microorganisms following Incubation with uPEC

| Organism | Negative Control | Positive Control | Dilution | Test Average | % Recovery |
|---|---|---|---|---|---|
| S. Aureus | 0 CFU | 57 CFU | 1:50 | 0 CFU | 0% |
| | | | 1:100 | 0 CFU | 0% |
| | | | 1:200 | 0 CFU | 0% |
| E. coli | 0 CFU | 63 CFU | 1:50 | 0 CFU | 0% |
| | | | 1:100 | 1 CFU | 2% |
| | | | 1:200 | 1 CFU | 2% |
| S. enterica | 0 CFU | 66 CFU | 1:50 | 48 CFU | 73% |
| | | | 1:100 | 62 CFU | 94% |
| | | | 1:200 | 56 CFU | 85% |

The uPEC percent recovery for *E. coli* is also given in Table 1. For a dilution of 1:50 the recovery was 0%, for a dilution of 1:100 the recovery was 2%, and for a dilution of 1:200 the recovery was 2%.

The uPEC percent recovery for *S. enterica* is also given in Table 1. For a dilution of 1:50 the recovery was 73%, for a dilution of 1:100 the recovery was 94%, and for a dilution of 1:200 the recovery was 85%.

Test results using the lipid encapsulate PEC (ePEC) are given in Table 2, below. As shown, for dilutions of 1:50 the recovery of *S. aureus* was 29%, for a dilution of 1:100 the recovery was 0%, and for a 1:200 the percent recovery of *S. aureus* was also 0%.

TABLE 2

Recovery of Microorganisms following Incubation with ePEC

| Organism | Negative Control | Positive Control | Dilution | Test Average | % Recovery |
|---|---|---|---|---|---|
| S. aureus | 0 CFU | 34 CFU | 1:50 | 10 CFU | 29% |
| | | | 1:100 | 0 CFU | 0% |
| | | | 1:200 | 0 CFU | 0% |
| E. coli | 0 CFU | 38 CFU | 1:50 | 12 CFU | 32% |
| | | | 1:100 | 9 CFU | 17% |
| | | | 1:200 | 28 CFU | 78% |
| S. enterica | 0 CFU | 61 CFU | 1:50 | 53 CFU | 87% |
| | | | 1:100 | N/P | N/P |
| | | | 1:200 | N/P | N/P |

The ePEC percent recovery for *E. Coli* are also in Table 2. For a dilution of 1:50 the recovery was 32%, for a dilution of 1:100 the recovery was 17%, and for a dilution of 1:200 the recovery was 78%.

The ePEC percent recovery for *S. enterica* are also given in Table 2. For a dilution of 1:50 the recovery was 87%, for a dilution of 1:100 and 1:200 the tests were not performed.

Positive controls as reported in Tables 1 and 2 clearly demonstrate that the growth media for all microbiological cultures were functioning effectively. In Table 1, it can be seen that the uPEC composition was highly effective on both *S. aureus* and *E. coli*. This is substantiated by the fact that recovery of positively spiked controls failed to meet the USP criterion of positive recovery (at least 70% of spiked sample CFUs recovered).

It is also important to note that the bacteriostatic/bactericidal activity showed species specificity. Samples of *S. enterica* showed excellent recovery using both coated and uncoated PEC. Because bacteria share common cell wall and membrane structures such as lipids and peptidoglycans, it is possible that these results point to the sensitivity of a more species specific cellular component such as a protein. If lipase or amylase action alone were sufficient to induce bacterial death or suppression of growth, then it would be unlikely to see the recovery of *S. enterica* at such robust levels. It is possible that species specific protein(s) in *S. aureus* and *E. coli* share similar peptide sequences and the appropriate local tertiary structure to allow for enzymatic attack by one or several of the proteases present in PEC, leading to a subsequent destruction of the bacterium. These results do not however, rule out a multi-staged event where action by lipases and amylases against the bacterial cell wall and membrane first expose extracellular or transmembrane proteins which have the appropriate primary and tertiary structure to lend themselves to enzymatic degradation by one or many of the PEC proteases.

These results demonstrate a clear bacteriostatic effect on *S. aureus* and *E. coli* for both lipid coated and uncoated PEC. Because this experiment relies upon an end point read out of bacterial colony growth while the subject bacteria remain in the presence of PEC, it is not possible on the basis of these results to rule out the possibility of a bacteriostatic effect only. Thus, failure to recover a sufficient number of viable colony forming units could be the result of the continued suppressive presence of the PEC material, as opposed to the induction of bacterial death. Consequently, additional experimental testing was carried out in order to more conclusively evaluate the bactericidal capabilities of PEC.

Materials and Methods:

The uncoated PEC formulation described above previously was used to evaluate bacteriocidal activity of the formulations.

Preparation of Test Dilutions—

Bulk dilutions of uPEC were prepared at 1:100 and 1:200 in Tryptic Soy broth containing 4% Polysorbate 20 and 0.5% lecithin. The bulk dilution was then split into separate 10 ml aliquots, where were then inoculated with a low number of colony forming units (CFUs<100) of the appropriate microorganisms. One millimeter of the inoculated aliquots was plated in duplicate using the appropriate solid medium (agar). Positive controls were prepared, inoculated, and plated in a manner similar to the test samples. Negative controls were prepared, inoculated with sterile reagent, and plated in a manner similar to the test samples. The plates were incubated at 30° C. to 35° C. for two days. Following this initial incubation, cultured material was then collected and washed in Phosphate Buffered Saline (PBS) and filtered in order to remove PEC. The material was resuspended in diluted in Tryptic Soy broth as per above and re-plated onto fresh solid (agar) media and incubated for an additional 2 days. At the end of this period, colonies were enumerated and the percentage recovery calculated. At the end of the period the recovery was calculated. Recovery of inoculated organisms must be at least 70% in order to show no inhibition of growth. Triphenyltetrazolium chloride was used to count the plates.

Tests for E. coli—

Dilutions prepared with Lactose broth containing 4% polysorbate 20 and 0.5% lecithin were inoculated with <=100 CFU of E. coli. The inoculated dilutions were incubated at 30° C. to 35° C. for 24 hours prior to being streaked to MacKonkey agar. The plates were observed for colonies characteristic of E. coli. Where observed, a representative colony was confirmed to be E. coli using an API 20e biochemical identification test.

The tests were also repeated for both S. Aureus and E. Coli at Dilutions of 1:20, 1:40, and 1:80.

Test Results

Test Results using the uncoated uPEC are given in Tables 3 and 4, below, demonstrating recovery of bacteria following replating of bacteria alone, post-incubation with uPEC and washing. As shown in Table 3, for dilutions of 1:100, and 1:200, the percent recovery of S. aureus was 13% and 48%, respectively, clearly demonstrating the bacteriocidal action of uPEC on S. aureus. As shown in Table 4, the percent recovery of S. Aureus at a dilution of 1:20 is 2%, for a dilution of 1:40 it is 4%, and for a dilution of 1:80 it is 23%.

TABLE 3

Bactericidal Action Post Wash/Recovery of Microorganisms

| Organism | Negative Control | Positive Control | Dilution | Test Average | % Recovery |
|---|---|---|---|---|---|
| S. Aureus | 0 CFU | 48 CFU | 1:100 | 6 CFU | 13% |
|  |  |  | 1:200 | 23 CFU | 48% |
| E. coli | 0 CFU | 46 CFU | 1:100 | 1 CFU | 2% |
|  |  |  | 1:200 | 13 CFU | 28% |

TABLE 4

Bactericidal Action Post Wash/Recovery of Microorganisms

| Organism | Negative Control | Positive Control | Dilution | Test Average | % Recovery |
|---|---|---|---|---|---|
| S. Aureus | 0 CFU | 47 CFU | 1:20 | 1 CFU | 2% |
|  |  |  | 1:40 | 2 CFU | 4% |
|  |  |  | 1:80 | 11 CFU | 23% |
| E. coli | 0 CFU | 43 CFU | 1:20 | 0 CFU | 0% |
|  |  |  | 1:40 | 0 CFU | 0% |
|  |  |  | 1:80 | 5 CFU | 12% |

The recovery for E. coli is also given in Tables 3 and 4. As shown in Table 3, for a dilution of 1:100 the recovery was 2%, and for a dilution of 1:200 the recovery was 28%. As shown in Table 4, the percent recovery of E. Coli at dilution of 1:20 is 0%, for a dilution of 1:40 it is 0%, and for a dilution of 1:80 it is 12%

Positive controls demonstrate that the growth media for all microbiological cultures were functioning effectively. This argues for a true bactericidal effect when the selected organisms are exposed to PEC. If the action of the PEC were merely bacteriostatic, removing the PEC from co-culture with the test bacteria would result in a release from any suppressive action by the PEC with a recovery of active growth. However, removal of PEC does not result in any such recovery, even though cultures were left to grow over a full 24 hr period. This strongly supports the notion that the reason the selected organisms fail to show recovery of CFU's upon exposure to PEC is because of a bactericidal action of the PEC. This action could include mechanisms such as physical and irreversible damage to cell surface lipids, membrane proteins or bacterial capsule by enzymatic degradation, leading to extracellular and intercellular ionic electrolyte imbalances, changes in acidity, and damage to genetic material.

A number of embodiments of the invention have been described. Nevertheless, it will be understood that various modifications may be made without departing from the spirit and scope of the invention. Accordingly, other embodiments are within the scope of the following claims.

What is claimed is:

1. A method for the treatment or prevention of Escherichia coli (E. coli) infection in a bird or a mammal, comprising administering to the bird or mammal a therapeutically effective amount of a pharmaceutical composition that consists of digestive enzymes, one or more excipient(s), and a lipid coating; wherein the digestive enzymes comprise a protease, an amylase, and a lipase, wherein the lipid coating coats the digestive enzymes and the one or more excipient(s), and wherein the pharmaceutical composition is bacteriocidal or bacteriostatic for E. coli.

2. The method of claim 1, wherein the digestive enzymes further comprise one or more enzyme(s) selected from the group consisting of a cellulase, a sucrase, a maltase, and papain.

3. The method of claim 1, wherein the digestive enzymes comprise pancreatic enzymes.

4. The method of claim 1, wherein the digestive enzymes comprise pig enzymes.

5. The method of claim 1, wherein the digestive enzymes comprise a mixture of proteases, and wherein the mixture of proteases comprises chymotrypsin and trypsin.

6. The method of claim 1, wherein the digestive enzymes are animal enzymes, microbial enzymes, plant enzymes, or are synthetically prepared.

7. The method of claim 1, wherein the mammal is a pig, a horse, a cow, a dog, a cat, a monkey, a rat, a mouse, a sheep, a goat, or a human; or wherein the bird is a chicken, a duck, a turkey, or a goose.

8. The method of claim 6, wherein the digestive enzymes are derived from an animal source, and wherein the animal source is a pig pancreas.

9. The method of claim 1, wherein the pharmaceutical composition comprises at least one amylase, a mixture of proteases comprising chymotrypsin and trypsin, and at least one lipase.

10. The method of claim 1, wherein a ratio of total protease to total lipase in the pharmaceutical composition in U.S.P. units ranges from about 1:1 to about 20:1.

11. The method of claim 1, wherein the ratio of total protease to total lipase in the pharmaceutical composition in U.S.P. units ranges from about 4:1 to about 10:1.

12. The method of claim 1, wherein the pharmaceutical composition is formulated for oral administration.

13. The method of claim 1, wherein the pharmaceutical composition is formulated for topical administration.

14. The method of claim 1, wherein the pharmaceutical composition is bacteriocidal or bacteriostatic for a Shiga toxin-producing *E. coli* (STEC).

15. The method of claim 1, wherein the pharmaceutical composition is bacteriocidal or bacteriostatic for an Enterotoxigenic *E. coli* (ETEC).

16. A method of treating a mammal or bird exhibiting one or more symptoms of an *Escherichia coli* (*E. coli*) infection, comprising administering to the mammal or bird a therapeutically effective amount of a pharmaceutical composition that consists of digestive enzymes, one or more excipient(s), and a lipid coating; wherein the digestive enzymes comprise a protease, an amylase, and a lipase, wherein the lipid coating coats the digestive enzymes and the one or more excipient(s), and wherein the pharmaceutical composition is bacteriocidal or bacteriostatic for the *E. coli*.

17. The method of claim 1 or 16, further comprising administering a beta-lactam antibiotic to the mammal or bird.

18. The method of claim 1, wherein the pharmaceutical composition is bacteriocidal or bacteriostatic for an Enteropathogenic *E. coli* (EPEC).

19. The method of claim 16, wherein the pharmaceutical composition is bacteriocidal or bacteriostatic for an Enteropathogenic *E. coli* (EPEC).

20. The method of claim 16, wherein the pharmaceutical composition is bacteriocidal or bacteriostatic for a Shiga toxin-producing *E. coli* (STEC).

21. The method of claim 16, wherein the pharmaceutical composition is bacteriocidal or bacteriostatic for an Enterotoxigenic *E. coli* (ETEC).

22. The method of claim 1, wherein the lipid coating comprises a soy oil.

23. The method of claim 16, wherein the lipid coating comprises a soy oil.

\* \* \* \* \*